US011851479B2

(12) United States Patent
Burnham-Marusich

(10) Patent No.: US 11,851,479 B2
(45) Date of Patent: Dec. 26, 2023

(54) METHODS AND COMPOSITIONS FOR PERTUSSIS DIAGNOSIS

(71) Applicant: DX DISCOVERY INC., Reno, NV (US)

(72) Inventor: Amanda Burnham-Marusich, Reno, NV (US)

(73) Assignee: DXDISCOVERY, INC., Reno, NV (US)

( * ) Notice: Subject to any disclaimer, the term of this patent is extended or adjusted under 35 U.S.C. 154(b) by 439 days.

(21) Appl. No.: 17/058,446

(22) PCT Filed: Jun. 18, 2019

(86) PCT No.: PCT/US2019/037618
§ 371 (c)(1),
(2) Date: Nov. 24, 2020

(87) PCT Pub. No.: WO2019/246021
PCT Pub. Date: Dec. 26, 2019

(65) Prior Publication Data
US 2021/0214420 A1   Jul. 15, 2021

Related U.S. Application Data

(60) Provisional application No. 62/829,802, filed on Apr. 5, 2019, provisional application No. 62/686,412, filed on Jun. 18, 2018.

(51) Int. Cl.
*C07K 16/12* (2006.01)
*G01N 33/569* (2006.01)
*G01N 33/543* (2006.01)
*A61K 39/00* (2006.01)

(52) U.S. Cl.
CPC ... *C07K 16/1225* (2013.01); *G01N 33/54388* (2021.08); *G01N 33/56911* (2013.01); *A61K 2039/505* (2013.01); *C07K 2317/565* (2013.01); *G01N 2333/235* (2013.01)

(58) Field of Classification Search
CPC combination set(s) only.
See application file for complete search history.

(56) References Cited

U.S. PATENT DOCUMENTS 8,574,596 B2   11/2013   Castado et al.
2016/0116462 A1   4/2016   Ashworth-Sharpe et al.

FOREIGN PATENT DOCUMENTS

WO   WO-2017196426 A1 * 11/2017 ............. C07K 16/28

OTHER PUBLICATIONS

Kussie PH, Parhami-Seren B, Wysocki LJ, Margolies MN. J Immunol. Jan. 1, 1994;152(1):146-52. PMID: 8254187. (Year: 1994).*
Chen C, Roberts VA, Stevens S, Brown M, Stenzel-Poore MP, Rittenberg MB. EMBO J. Jun. 15, 1995;14(12):2784-94. doi: 10.1002/j.1460-2075.1995.tb07278.x. PMID: 7796805; PMCID: PMC398397. (Year: 1995).*
Burnham-Marusich, A.R., et al., "Tracheal colonization factor A (TcfA) is a biomarker for rapid and specific detection of Bordetella pertussis" Scientific Reports (2020) 10:15002.
Van Gent, M., et al., "Characterization ofBordetella pertussis clinical isolates that do not express the tracheal colonization factor" FEMS Immunol. Med. Microbiol. (2007) 51:149-154.
Weiss, A.A., et al., "Characterization of Human Bactericidal Antibodies to Bordetella pertussis" Infect. Immun. (1999) 67(3):1424-31.
Valentini, D., et al., "Serum reactome induced by Bordetella pertussis infection and Pertussis vaccines: qualitative differences in serum antibody recognition patterns revealed by peptide microarray analysis" BMC Immunol. (2015) 16:40.
Doebel-Hickok, M. "Characterizing the Secretion and Function of TcfA: A Unique Autotransporter and Virulence Factor in Bordetella pertussis" University of British Columbia, Master thesis (2018) pp. 1-91, available at: https://open.library.ubc.ca/clRcle/collections/ubctheses/24/items/1.0362581.
Nguyen, A.W., et al., "A cocktail of humanized anti-pertussis toxin antibodies limits disease in murine and baboon models of whooping cough" Sci. Trans. Med. (2015) 7(316):316ra195.
Packard, E.R., et al., "Sequence variation and conservation in virulence-related genes of Bordetella pertussis solates from the UK" Journal of Medical Microbiology (2004) 53:355-365.
Van Amersfoorth, S.C.M., et al., "Analysis of Bordetella pertussis Populations in European Countries with Different Vaccination Policies" J. Clin. Microbiol. (2005) 43(6):2837-2843.
Van Loo, I.H.M., et al., "Multilocus Sequence Typing of Bordetella pertussis Based on Surface Protein Genes" J. Clin. Microbiol. (2002) 40(6):1994-2001.
Boreland, P.C., et al., "Counterimmunoelectrophoresis in the diagnosis of whooping cough" J. Clin. Pathol. (1984) 37:950-951.

(Continued)

*Primary Examiner* — Adam Weidner
*Assistant Examiner* — Laura Ann Essex
(74) *Attorney, Agent, or Firm* — Robert C. Netter, Jr.; Dann, Dorfman, Herrell & Skillman

(57) ABSTRACT

Compositions and methods for the detection and diagnosis of *Bordetella pertussis* are disclosed. Provided are antibodies, or antigen binding fragment thereof, specific for tracheal colonization factor A (TcfA). Also provided are compositions comprising an anti-TcfA antibody of the instant invention and a carrier; and methods for inhibiting, treating, and/or preventing pertussis and/or a *B. pertussis* infection in a subject in need thereof are provided, comprising administering an anti-TcfA antibody of the instant invention to the subject.

22 Claims, 19 Drawing Sheets
Specification includes a Sequence Listing.

(56) References Cited

OTHER PUBLICATIONS

Boreland, P.C., et al., "Rapid diagnosis of whooping cough using monoclonal antibody" J. Clin. Pathol. (1988) 41:573-575.
Gustafsson, B., et al., "Monoclonal Antibody-Based Sandwich Enzyme-Linked Immunosorbent Assay for Detection of Bordetella pertussis Filamentous Hemagglutinin" J. Clin. Microbiol. (1988) 26(10):2077-2082.
Gustafsson, B., et al., "Rapid Detection of Bordetella pertussis by a Monoclonal Antibody-Based Colony Blot Assay" J. Clin. Microbiol. (1989) 27(4):628-631.

* cited by examiner

Figure 4

| mAb[1] | Isotype | B. pertussis cells (OD600 = 1) | rTcfA-His (1µg/ml) | TcfA:BSA conjugates (0.1µg/ml) | | | BSA (0.1µg/ml) | SS CM[2] | SS Media[3] |
|---|---|---|---|---|---|---|---|---|---|
| | | | | aa140-160 | aa288-304 | aa305-323 | | | |
| 10B1 | IgG1 | 3.27 | 3.32 | 3.34 | 0.11 | 0.07 | 0.07 | 0.45 | 0.05 |
| 7E11 | IgG1 | 3.36 | 3.33 | 3.29 | 0.09 | 0.08 | 0.04 | 0.39 | 0.05 |
| 7A10 | IgG1 | 3.19 | 3.31 | 3.34 | 0.17 | 0.09 | 0.05 | 0.06 | 0.04 |
| 9A3 | IgG1 | 2.57 | 3.31 | 3.28 | 0.12 | 0.07 | 0.04 | 0.05 | 0.04 |
| 7E9 | IgG1 | 3.32 | 3.31 | 3.30 | 0.13 | 0.07 | 0.04 | 0.12 | 0.04 |
| 3E6 | IgG2a | 3.33 | 3.15 | 3.29 | 0.17 | 0.09 | 0.04 | 1.42 | 0.04 |
| 7A3 | IgG2b | 3.35 | 3.36 | 3.35 | 0.15 | 0.08 | 0.07 | 0.21 | 0.04 |
| 15F3 | IgG1 | 0.43 | 2.72 | 3.31 | 0.05 | 0.06 | 0.04 | 0.05 | 0.04 |
| 21D6 | IgG1 | 3.36 | 3.21 | 3.32 | 0.11 | 0.07 | 0.04 | 0.36 | 0.04 |
| 15A9 | IgG1 | 3.34 | 3.36 | 3.31 | 0.13 | 0.07 | 0.04 | 0.59 | 0.05 |
| 14F4 | IgG1 | 3.35 | 3.34 | 3.31 | 0.12 | 0.07 | 0.05 | 0.59 | 0.04 |
| 17H2 | IgG1 | 3.30 | 3.34 | 3.30 | 0.12 | 0.07 | 0.06 | 0.34 | 0.04 |
| 14G6 | IgG1 | 3.35 | 3.22 | 3.32 | 0.48 | 0.44 | 0.12 | 0.66 | 0.04 |
| 15B9 | IgG1 | 3.35 | 3.35 | 3.31 | 0.37 | 0.22 | 0.05 | 0.60 | 0.04 |
| 11B5 | IgG2b | 1.99 | 3.30 | 3.31 | 0.27 | 0.09 | 0.05 | 0.05 | 0.05 |
| 4A6 | IgG1 | 3.25 | 3.31 | 3.31 | 0.21 | 0.29 | 0.05 | 0.20 | 0.04 |
| 13E11 | IgG2b | 3.34 | 3.31 | 0.08 | 1.98 | 3.30 | 0.05 | 0.24 | 0.04 |
| 19D10 | IgG2b | 3.35 | 3.34 | 0.05 | 2.42 | 3.29 | 0.04 | 0.29 | 0.04 |
| 22B7 | IgG1 | 3.33 | 3.31 | 0.10 | 3.33 | 3.32 | 0.04 | 2.70 | 0.04 |
| 14D9 | IgG2b | 3.34 | 3.35 | 0.06 | 3.30 | 3.31 | 0.05 | 0.49 | 0.04 |
| 19F9 | IgG2b | 3.35 | 3.33 | 1.01 | 3.30 | 0.91 | 0.05 | 0.50 | 0.04 |
| 23F8 | IgG1 | 3.35 | 3.34 | 0.05 | 3.31 | 0.54 | 0.04 | 0.09 | 0.05 |
| 14D12 | IgG1 | 3.35 | 3.33 | 0.23 | 3.28 | 0.16 | 0.04 | 1.26 | 0.05 |
| 20F4 | IgG1 | 0.61 | 3.04 | 0.05 | 0.07 | 3.28 | 0.06 | 0.05 | 0.06 |
| 14A8 | IgG1 | 3.11 | 3.32 | 0.13 | 0.05 | 3.30 | 0.10 | 0.05 | 0.04 |
| 14G11 | IgG1 | 1.25 | 3.27 | 0.05 | 0.05 | 3.31 | 0.06 | 0.05 | 0.04 |
| 25E3 | IgG2b | 3.34 | 3.32 | 0.07 | 0.06 | 0.07 | 0.05 | 2.52 | 0.04 |
| 18B2 | IgG2a | 3.11 | 3.32 | 0.05 | 0.05 | 0.04 | 0.05 | 0.23 | 0.04 |
| Blocking Buffer | NA | 0.31 | 0.06 | 0.05 | 0.05 | 0.05 | 0.05 | 0.05 | 0.04 |

```
  1 MHIYGNMNRA TPCRGAVRAL ALALLGAGMW TLSPPSAWAL KLPSLLTDDE LKLVLPTGMS
 61 LEDFKRSLQE SAPSALATPP SSSPPVAKPG PGSVAEAPSG SGHKDNPSPP VVGVGPGMAE
121 SSGGHNPGVG GGTHENGLPG IGKVGGSAPG PDTSTGSGPD AGMASGAGST SPGASGGAGK
181 DAMPPSEGER PDSGMSDSGR GGESSAGGLN PDGAGKPPRE EGEPGSKSPA DGGQDGPPPP
241 RDGGDADPQP PRDDGNGEQQ PPKGGGDEGQ RPPPAAGNGG NGGNGNAQLP ERGDDAGPKP
301 PEGEGGDEGP QPPQGGGEQD APEVPPVAPA PPAGNGVYDP GTHTLTTPAS AAVSLASSSH
361 GVWQAEMNAL SKRMGELRLT PVAGGVWGRA FGRRQDVDNR VSREFRQTIS GFELGADTAL
421 PVADGRWHVG AVAGYTNGRI KFDRGGTGDD DSVHVGAYAT YIEDGGFYMD GIVRVSRIRH
481 AFKVDDAKGR RVRGQYRGNG VGASLELGKR FTWPGAWYVE PQLEVAAFHA QGADYTASNG
541 LRIKDDGTNS MLGRLGLHVG RQFDLGDGRV VQPYMKLSWV QEFDGKGTVR TNDIRHKVRL
601 DGGRTELAVG VASQLGKHGS LFGSYEYAKG SRQTMPWTFH VGYRYAW
```

Figure 6

Heavy chain: DNA sequence (408 bp)

Signal sequence-FR1-CDR1-FR2-CDR2-FR3-CDR3-FR4

ATGAACTTCGGGCTCAGCTTGATTTTCCTTGTCCTTATTTTAAAAGGTGTCCAGTGTGAAGTGATGC
TGGTGGAGTCTGGGGGAGGCTTAGTGAAGCCTGGAGGGTCCCTGAAACTCTCCTGTGCAGCCTCTGG
AATAACTTTCAGTAACTATGCCATGTCTTGGATTCGCCAGACTCCAGAGAAGAGACTGGAGTGGGTC
GCAAGTATTAGTAGTGGTGGTAGTTATATCTACTATTCAGACAGTGTGAAGGGTCGATTCACCATTT
CCAGAGACAATGCCAGGAACACCCTGAACCTGCAAATGAGCAGTCTGAGGTCTGAGGACACGGCCAT
GTATTACTGTGTAAGAGGGGCGCATGGAAATTTTGACTACTGGGGCCAAGGCACCACTCTCACAGTC
TCCTCA

Heavy chain: Amino acid sequence (136 aa)

Signal peptide-FR1-CDR1-FR2-CDR2-FR3-CDR3-FR4

MNFGLSLIFLVLILKGVQCEVMLVESGGALVKPGGSLKLSCAASGITFSNYAMSWIRQTPEKRLEWV
ASISSGGSYIYYSDSVKGRFTISRDNARNTLNLQMSSLRSEDTAMYYCVRGAHGNFDYWGQGTTLTV
SS

Light chain: DNA sequence (393 bp)

Signal sequence-FR1-CDR1-FR2-CDR2-FR3-CDR3-FR4

ATGGAGTCAGACACACTCCTGCTATGGGTGCTGCTGCTCTGGGTTCCAGGCTCCACTGGTGACATTG
TGCTGACCCAATCTCCAGCTTCTTTGGCTGTGTCTCTAGGGCAGAGAGCCACCATCTCCTGCAGAAC
CAGTGAAACTGTTGATTATGATGGCGATAGTTATATGAACTGGTACCAACAGAAATCAGGACAGCCA
CCCAAACTCCTCATATCTGGTGCATCCAACGTAGAGTCTGGGGTCCCTGCCAGGTTCAGTGGCAGTG
GGTCTGGGACAGACTTCAGCCTCAACATCCATCCTGTGGAGGAGGATGATATTACAATGTATTTCTG
TCAGCAAAATAGGAAGCTTCCGTATACGTTCGGATCGGGGACCAAGCTGGAAATGAAA

Light chain: Amino acid sequence (131 aa)

Signal peptide-FR1-CDR1-FR2-CDR2-FR3-CDR3-FR4

MESDTLLLWVLLLWVPGSTGDIVLTQSPASLAVSLGQRATISCRTSETVDYDGDSYMNWYQQKSGQP
PKLLISGASNVESGVPARFSGSGSGTDFSLNIHPVEEDDITMYFCQQNRKLPYTFGSGTKLEMK

Figure 11A

Heavy chain: DNA sequence (417 bp)

Signal sequence-FR1-CDR1-FR2-CDR2-FR3-CDR3-FR4

ATGGACTCCAGGCTCAATTTAGTTTTCCTTGTCCTTTTTTTAAAAGGTGTCCAGTGTGAGGTGCAGC
TGGTGGAGTCTGGGGGAGGCTTAGTGAAGCCTGGAGGGTCCCGGAAACTCTCCTGTGCAGCCTCTGG
ATTCACTTTCAGTGACTATGGAATGCACTGGGTTCGTCAGGCTCCAGAGAAGGGACTGGAGTGGGTT
GCATACATTAGTAGTGGCAGTAGAACCATCTACTATGCAGACACAGTGAAGGGCCGATTCACCATCT
CCAGAGACAATGCCAAGAACACCCTGTTCCTGCAAATGACCAGTCTAAGGTCTGAGGACACGGCCAT
GTATTACTGTGCAAGGCTGGGCTATGGTTACGACTGGTACTTCGATGTCTGGGGCACAGGGACCACG
GTCACCGTCTCCTCA

Heavy chain: Amino acid sequence (139 aa)

Signal peptide-FR1-CDR1-FR2-CDR2-FR3-CDR3-FR4

MDSRLNLVFLVLFLKGVQCEVQLVESGGGLVKPGGSRKLSCAASGFTFSDYGMHWVRQAPEKGLEWV
AYISSGSRTIYYADTVKGRFTISRDNAKNTLFLQMTSLRSEDTAMYYCARLGYGYDWYFDVWGTGTT
VTVSS

Light chain: DNA sequence (393 bp)

Signal sequence-FR1-CDR1-FR2-CDR2-FR3-CDR3-FR4

ATGAGTCCTGCCCAGTTCCTGTTTCTGTTAGTGCTCTGGATGCGGGAAACCAACGGTGATGTTGTGA
TGACCCAGACTCCACTCACTTTGTCGGTTACCATTGGACAACCAGCCTCCATCTCCTGCAAGTCAAG
TCAGAGCCTCTTAGATAGTGATGGAAGGACATATTTGAATTGGTTGTTACAGAGGCCAGGCCAGTCT
CCAAAGCGCCTGATCTATCTGGTGTCTAAACTGGACTCTGGAGTCCCTGACAGGTTCACTGGCAGTG
GATCAGGGACAGATTTCACACTGAAAATCAGCAGAGTGGAGGCTGAGGATTTGGGAATTTATTATTG
CTGGCAAGGTACACATTTTCCTCAGACGTTCGGTGGAGGCACCAAGCTGGAAATCAAA

Light chain: Amino acid sequence (131 aa)

Signal peptide-FR1-CDR1-FR2-CDR2-FR3-CDR3-FR4

MSPAQFLFLLVLWMRETNGDVVMTQTPLTLSVTIGQPASISCKSSQSLLDSDGRTYLNWLLQRPGQS
PKRLIYLVSKLDSGVPDRFTGSGSGTDFTLKISRVEAEDLGIYYCWQGTHFPQTFGGGTKLEIK

Figure 11B

Heavy chain: DNA sequence (420 bp)

Signal sequence-FR1-CDR1-FR2-CDR2-FR3-CDR3-FR4

ATGGAATGGAGCGGGGTCTTTATCTTTCTCCTGTCAGTAACTGCAGGTGTCCACTCCCAGGTCCAGC
TGCAGCAGTCTGGAGCTGAGCTGGTAAGGCCTGGGACTTCAGTGAAGATGTCCTGCAAGGCTGCTGG
ATACACCTTCACTAACTACTGGATAGGTTGGGTAAAGCAGAGGCCTGGACATGGCCTTGAGTGGATT
GGAGATATTTACCCTGGAGGTGTTTATACTAACTACAATGAGAACTTCAAGGGCAAGGCCACACTGA
CGGCAGACACATCCTCCAGCACAGCCCACATGCAGCTCAGCAGCCTGACATCTGAGGACTCTGCCAT
CTATTACTGTGTAAGAGGAGGGAAGTATGGTAACTTTTTCGCTATGGACTACTGGGGTCAAGGAACG
TCAGTCACCGTCTCCTCA

Heavy chain: Amino acid sequence (140 aa)

Signal peptide-FR1-CDR1-FR2-CDR2-FR3-CDR3-FR4

MEWSGVFIFLLSVTAGVHSQVQLQQSGAELVRPGTSVKMSCKAAGYTFTNYWIGWVKQRPGHGLEWI
GDIYPGGVYTNYNENFKGKATLTADTSSSTAHMQLSSLTSEDSAIYYCVRGGKYGNFFAMDYWGQGT
SVTVSS

Light chain: DNA sequence (396 bp)

Signal sequence-FR1-CDR1-FR2-CDR2-FR3-CDR3-FR4

ATGAGGTGCTCTCTTCAGTTCCTGGGGGTGCTTATGTTCTGGATCTCTGGAGTCACTGGGGATATTG
TGATAACCCAGGATGAACTCTCCAATCCTGTCACTTCTGGAGAATCAGTTTCCATCTCCTGCAGGTC
TAGTAAGAGTCTCCTATATAAGGATGGGAAGACATACTTGAATTGGTTTCTGCAGAGACCAGGACAA
TCTCCTCAGCTCCTGATCTATTTGATGTCCACCCGTGCATCAGGAGTCTCAGACCGGTTTAGTGGCA
GTGGGTCAGGAACAGATTTCACCCTGGAAATCAGTAGAGTGAAGGCTGAGGATGTGGGTGTGTATTA
CTGTCAACAACTTGTAGAGTATCCATTCACGTTCGGCTCGGGGACAAAATTGGAAATAAAA

Light chain: Amino acid sequence (132 aa)

Signal peptide-FR1-CDR1-FR2-CDR2-FR3-CDR3-FR4

MRCSLQFLGVLMFWISGVTGDIVITQDELSNPVTSGESVSISCRSSKSLLYKDGKTYLNWFLQRPGQ
SPQLLIYLMSTRASGVSDRFSGSGSGTDFTLEISRVKAEDVGVYYCQQLVEYPFTFGSGTKLEIK

Figure 11C

Heavy chain: DNA sequence (408 bp)

Signal sequence-FR1-CDR1-FR2-CDR2-FR3-CDR3-FR4

ATGGCTTGGGTGTGGACCTTGCTATTCCTGATGGCAGCTGCCCAAAGTGCCCAAGCACAGATCCAGT
TGGTGCAGTCTGGACCTGAGCTGAAGAAGCCTGGAGAGACAGTCAAGATCTCCTGCAAGGCTTCTGG
GTATACCTTCACAAACTATGGAATGAACTGGGTGAAGCAGGCTCCAGGAAAGGGTTTAAAGTGGATG
GGCTGGATAAACACCTACACTGGAGAGCCAACATATGCTGATGACTTCAAGGGACGGTTTGCCTTCT
CTTTGGAAACCTCTGCCACCACTGCCTATTTGCAGATCAACAACCTCAAAAATGAGGACACGGCTAC
ATATTTCTGTGCAAGGGCGGCTACGGGGTACTTTGACTACTGGGGCCAAGGCACCACTCTCACAGTC
TCCTCA

Heavy chain: Amino acid sequence (136 aa)

Signal peptide-FR1-CDR1-FR2-CDR2-FR3-CDR3-FR4

MAWVWTLLFLMAAAQSAQAQIQLVQSGPELKKPGETVKISCKASGYTFTNYGMNWVKQAPGKGLKWM
GWINTYTGEPTYADDFKGRFAFSLETSATTAYLQINNLKNEDTATYFCARAATGYFDYWGQGTTLTV
SS

Light chain: DNA sequence (396 bp)

Signal sequence-FR1-CDR1-FR2-CDR2-FR3-CDR3-FR4

ATGGATTCACAGGCCCAAGTTCTTATGTTGCTGCTGCTATGGGTATCTGGTACCTGTGGGGACATTG
TGATGTCACAGTCTCCATCCTCCCTGGCTGTGTCAGCAGGAGAGAAGGTTACTATGAGCTGCAAGTC
CAGTCAGAGCCTTTTATATAGTAGCAATCAAAAGAACTACTTGGCCTGGTACCAGCAGAAACCAGGG
CAGTCTCCTAAACTGTTGATCTACTGGGCATCCACTAGGGAATCTGGGGTCCCTGACCGCTTCACAG
GCAGTGGATCAGGGACAGATTTCACTCTCACCATCAGCAGTGTGAAGGCTGAAGACCTGGCCGTTTA
TTACTGTCAGCAATATTATAACGAGTACACGTTCGGAGGGGGGACCAAGCTGGAAATAAAA

Light chain: Amino acid sequence (132 aa)

Signal peptide-FR1-CDR1-FR2-CDR2-FR3-CDR3-FR4

MDSQAQVLMLLLWVSGTCGDIVMSQSPSSLAVSAGEKVTMSCKSSQSLLYSSNQKNYLAWYQQKPG
QSPKLLIYWASTRESGVPDRFTGSGSGTDFTLTISSVKAEDLAVYYCQQYYNEYTFGGGTKLEIK

Figure 11D

Heavy chain: DNA sequence (438 bp)

Signal sequence-FR1-CDR1-FR2-CDR2-FR3-CDR3-FR4

ATGAAGTTGTGGCTGAACTGGATTTTCCTTGTAACACTTTTAAATGGTATCCAGTGTGAGGTGAAGC
TGGTGGAGTCTGGAGGAGGCTTGGTACAGCCTGGGGGTTCTCTGAGTCTCTCCTGTGCAGCTTCTGG
ATTCACCTTCACTGATTACTACATGAGCTGGGTCCGCCAGCCTCCAGGGAAGGCACTTGAGTGGTTG
GCTTTTATTAGAAACAAAGCTAATGGTTACACAACAGAGTACAGTGCATCTGTGAAGGCTCGCTTCA
CCATCTCCAGAGATAATTCCCAAAGCATCCTCTATCTTCAAATGAATGCCCTGAGAGCTGAGGACAG
TGCCACTTATTACTGTGCAAGATATAGGCGGGATTACTACGGTAGTCTTAATTACTATACTATGGAC
TACTGGGGTCAAGGAACCTCAGTCACCGTCTCCTCA

Heavy chain: Amino acid sequence (146 aa)

Signal peptide-FR1-CDR1-FR2-CDR2-FR3-CDR3-FR4

MKLWLNWIFLVTLLNGIQCEVKLVESGGGLVQPGGSLSLSCAASGFTFTDYYMSWVRQPPGKALEWL
GFIRNKANGYTTEYSASVKGRFTISRDNSQSILYLQMNALRAEDSATYYCARYRRDYYGSLNYYTMD
YWGQGTSVTVSS

Light chain: DNA sequence (381 bp)

Signal sequence-FR1-CDR1-FR2-CDR2-FR3-CDR3-FR4

ATGAGTGTGCCCACTCAGGTCCTGGGGTTGCTGCTGCTGTGGCTTACAGGTGCCAGATGTGACATCC
AGATGACTCAGTCTCCAGCCTCCCTATCTGCATCTGTGGGAGAAACTGTCACCATCACATGTCGAGC
AAGTGAGAATATTTACAGTTATTTAGCATGGTATCAGCAGAAACAGGGAAAATCTCCTCAGCTCCTG
GTCTATAATGCAAAAACCTTAGCAGAAGGTGTGCCATCAAGGTTCAGTGGCAGTGGATCAGGCACAC
AGTTTTCTCTGAAGATCAACAGCCTGCAGCCTGAAGATTTTGGGAGTTATTACTGTCAAAATCATTA
TGGTATTCCTCTCACGTTCGGTGCTGGGACCAAGCTGGAGCTGAAA

Light chain: Amino acid sequence (127 aa)

Signal peptide-FR1-CDR1-FR2-CDR2-FR3-CDR3-FR4

MSVPTQVLGLLLLWLTGARCDIQMTQSPASLSASVGETVTITCRASENIYSYLAWYQQKQGKSPQLL
VYNAKTLAEGVPSRFSGSGSGTQFSLKINSLQPEDFGSYYCQNHYGIPLTFGAGTKLELK

Figure 11E

Heavy chain: DNA sequence (411 bp)

Leader sequence-FR1-CDR1-FR2-CDR2-FR3-CDR3-FR4

ATGGACTCCAGGCTCAATTTAGTTTTCCTTGTCCTTATTTTAAAAGGTGTCCAGTGTGAGGTGCAGC
TGGTGGAGTCTGGGGGAGGCTTAGTGAAGCCTGGAGGGTCCCGGAAACTCTCCTGTGCAGCCTCTGG
ATTCACTTTCAGTGACTATGGAATGCACTGGGTTCGTCAGGCTCCAGAGAAGGGGCTGGAGTGGGTT
GCATACATTAGTAGTGGCAGTAGTACCATCTACTATGCAGACACAGTGAAGGGCCGATTCACCATCT
CCAGAGACAATGCCAAGAACACCCTGTTCCTGCAAATGACGAGTCTAAGGTCTGAGGACACGGCCAT
GTATTACTGTGCAAGGCCCCGAAGTGGGAGGTACTTTGACTACTGGGGCCAAGGCACCACTCTCACA
GTCTCCTCA

Heavy chain: Amino acids sequence (137 aa)

Leader sequence-FR1-CDR1-FR2-CDR2-FR3-CDR3-FR4

MDSRLNLVFLVLILKGVQCEVQLVESGGGLVKPGGSRKLSCAASGFTFSDYGMHWVRQAPEKGLEWV
AYISSGSSTIYYADTVKGRFTISRDNAKNTLFLQMTSLRSEDTAMYYCARPRSGRYFDYWGQGTTLT
VSS

Light chain: DNA sequence (393 bp)

Leader sequence-FR1-CDR1-FR2-CDR2-FR3-CDR3-FR4

ATGAGTCCTGCCCAGTTCCTGTTTCTGTTAGTGCTCTGGATTCAGGAAACCAACGGTGATGTTATGA
TGACCCAGACTCCACTCACTTTGTCGGTTACCATTGGACAACAGCTTCCATCTCTTGCAAGTCAAG
TCAGAGCCTCTTAGATAGTAACGGAAATACCTATCTGCATTGGTTATTACAGAGGCCAGGCCAGTCT
CCAAAGATCCTAATCTATCTGGTGTCTAAACTGGACTCTGGAGTCCCTGACAGGTTCAGTGGCAGTG
GGTCAGGAACAGATTTCACACTGAAAATCAGCAGAGTGGAGGCTGAGGATTTGGGAGTTTATTACTG
CTTGCAAGGTACACATTTTCCGTACACGTTCGGAGGGGGGACCAAGCTGGAAATAAAA

Light chain: Amino acids sequence (131 aa)

Leader sequence-FR1-CDR1-FR2-CDR2-FR3-CDR3-FR4

MSPAQFLFLLVLWIQETNGDVMMTQTPLTLSVTIGQPASISCKSSQSLLDSNGNTYLHWLLQRPGQS
PKILIYLVSKLDSGVPDRFSGSGSGTDFTLKISRVEAEDLGVYYCLQGTHFPYTFGGGTKLEIK

Figure 11F

Heavy chain: DNA sequence (393 bp)

Leader sequence-FR1-CDR1-FR2-CDR2-FR3-CDR3-FR4

ATGAAATGCAGCTGGGTTATCTTCTTCCTGATGGCAGTGGTTACAGGGGTCAATTCAGAGGTTCAGC
TGCAGCAGTCTGGGGCAGAGCTTGTGAAGCCAGGGGCCTCAGTCAAGTTGTCCTGCACAGCTTCTGG
CTTCAACATTAAAGACACCTATATACACTGGGTGAAACAGAGGCCTGAACAGGGCCTGGAGTGGATT
GGAAGGATTGATCCTGCGAATGGTAATACTATATATGCCTCAAAGTTCCAGGGCAAGGCCCCTATAA
CAGCAGTCACATCATCCAACACAGCCTACATGCAGTTCAGCAGCCTGACATCTGGGGACACTGCCGT
CTATTACTGTACTGCTATGGACTACTGGGGTCAAGGAACCTCAGTCACCGTCTCCTCA

Heavy chain: Amino acids sequence (131 aa)

Leader sequence-FR1-CDR1-FR2-CDR2-FR3-CDR3-FR4

MKCSWVIFFLMAVVTGVNSEVQLQQSGAELVKPGASVKLSCTASGFNIKDTYIHWVKQRPEQGLEWI
GRIDPANGNTIYASKFQGKAPIAVTSSNTAYMQFSSLISGDTAVYYCTAMDYWGQGTSVTVSS

Light chain: DNA sequence (393 bp)

Leader sequence-FR1-CDR1-FR2-CDR2-FR3-CDR3-FR4

ATGAGTCCTGCCCAGTTCCTGTTTCTGCTAGTGCTCGCGATTCAGGAAACCAACGGTGATGTTGTGA
TGACTCAGACCCCACTCACTTTGTCGGTTACCATTGGACAACCAGCCTCCATCTCTTGCAAATCAAG
TCAGAGCCTCTTACATAGTAATGGAAAGACATATTTGAATTGGTTATTACAGAGGCCAGGCCAGTCT
CCAAAGCTCCTAATCTATCTGGTGTCTAAACTGGATTCTGGAGTCCCTGACAGGTTCAGTGGCAGTG
GATCAGGGACAGATTTCACACTGAAAATCAGCAGAGTGGAGGCTGAGGATTTGGGAGTTTATTACTG
CTTGCAAGCTACACATTTTCCTCATACGTTCGGATCGGGACCAAGCTGGAAATAAAA

Light chain: Amino acids sequence (131 aa)

Leader sequence-FR1-CDR1-FR2-CDR2-FR3-CDR3-FR4

MSPAQFLFLLVLAIQETNGDVVMTQTPLTLSVTIGQPASISCKSSQSLLHSNGKTYLNWLLQRPGQS
PKLLIYLVSKLDSGVPDRFSGSGSGTDFTLKISRVEAEDLGVYYCLQATHFPHTFGSGTKLEIK

Figure 11G

Heavy chain: DNA sequence (393 bp)

Leader sequence-FR1-CDR1-FR2-CDR2-FR3-CDR3-FR4

ATGAAATGCAGCTGGGTTATCTTCTTCCTGATGGCAGTGGTTACAGGGGTCAATTCAGAGGTTCAGC
TGCAGCAGTCTGGGGCAGAGCTTGTGAAGCCAGGGGCCTCAGTCAAGTTGTCCTGCACAGCTTCTGG
CTTCAACATTAAAGACACCTATATACACTGGGTGAAGCAGAGGCCTGAACAGGGCCTGGAGTGGATT
GGAAGGATTGATCCTGCGAATGGTAATATTATATATGCCTCAAAGTTCCAGGGCGAGGCCACTATAA
CAGCAGACACATCATCCAACACAGCCTACATGCAGCTCAGCAGCCTGACATCTGGGGACACTGCCGT
CTATTACTGTAGCGCTATGGACTACTGGGGTCAAGGAACCTCAGTCACCGTCTCCTCA

Heavy chain: Amino acids sequence (131 aa)

Leader sequence-FR1-CDR1-FR2-CDR2-FR3-CDR3-FR4

MKCSWVIFFLMAVVTGVNSEVQLQQSGAELVKPGASVKLSCTASGFNIKDTYIHWVKQRPEQGLEWI
GRIDPANGNIIYASKFQGEATITADTSSNTAYMQLSSLTSGDTAVYYCSAMDYWGQGTSVTVSS

Light chain: DNA sequence (393 bp)

Leader sequence-FR1-CDR1-FR2-CDR2-FR3-CDR3-FR4

ATGAGTCCTGCCCAGTTCCTGTTTCTGCTAGTGCTCTCGATTCAGGAAACCAACGGTGATGTTGTGA
TGACTCAGACCCCACTCACTTTGTCGCTTACCATTGGACAACCAGCCTCCATCTCTTGCAAATCAAG
TCAGAGCCTCTTACATAGTAATGGAAAGACATATTTGAATTGGTTATTACAGAGGCCAGGCCAGTCT
CCTAAGCTCCTCATCTATCTGGTGTCTAAACTGGATTCTGGAGTCCCTGACAGGTTCAGTGGCAGTG
GATCAGGGACAGATTTCACACTGAAAATCAGCAGAGTGGAGGCTGAGGATTTGGGAGTTTATTACTG
CTTGCAAGCTACACATTTTCCTCATACGTTCGGATCGGGGACCAAGCTGGAAATAAAA

Light chain: Amino acids sequence (131 aa)

Leader sequence-FR1-CDR1-FR2-CDR2-FR3-CDR3-FR4

MSPAQFLFLLVLSIQETNGDVVMTQTPLTLSLTIGQPASISCKSSQSLLHSNGKTYLNWLLQRPGQS
PKLLIYLVSKLDSGVPDRFSGSGSGTDFTLKISRVEAEDLGVYYCLQATHFPHTPGSGTKLEIK

Figure 11H

Heavy chain: DNA sequence (414 bp)

Leader sequence-FR1-CDR1-FR2-CDR2-FR3-CDR3-FR4

ATGAAGTTGTGGCTGAACTGGATTTTCCTTGTAACACTTTTAAATGGTATCCAGTGTGAGGTGAAGC
TGGTGGAGTCTGGAGGAGGCTTGGTACAGCCTGGGGGTTCTCTGAGACTCTCCTGTGCAACTTCTGG
GTTCACCTTCACTGATTACTACATGAGCTGGGTCCGCCAGCCTCCAGGAAAGGCACTTGAGTGGATG
GGTTTTATTAGAAACAAAGCTAAAGGTTACACAACAGATTACAGTGCGTCTGTGAAGGGTCGGTTCA
CCATCTCCAGAGATGATTCCCAAAGCATCCTCTATCTTCAAATGAACACCCTGAGACCTGAGGACAG
TGCCACTTATTACTGTGCAAGAAACTATGACTATTCTATGGACTACTGGGGTCAAGGAACCTCAGTC
ACCGTCTCCTCA

Heavy chain: Amino acids sequence (138 aa)

Leader sequence-FR1-CDR1-FR2-CDR2-FR3-CDR3-FR4

MKLWLNWIFLVTLLNGIQCEVKLVESGGGLVQPGGSLRLSCATSGFTFTDYYMSWVRQPPGKALEWM
GFIRNKAKGYTTDYSASVKGRFTISRDDSQSILYLQMNTLRPEDSATYYCARNYDYSMDYWGQGTSV
TVSS

Light chain: DNA sequence (381 bp)

Leader sequence-FR1-CDR1-FR2-CDR2-FR3-CDR3-FR4

ATGAGTGTGCTCACTCAGGTCCTGGCGTTGCTGCTGCTGTGGCTTACAGGTGCCAGATGTGACATCC
AGCTGACTCAGTCTCCAGCCTCCCTATCTGCATCTGTGGGAGAAACTGTCACCATCACTTGTCGAGC
AAGTGATAATATTCACAAATATTTAGCATGGTATCAGCAGAAACAGGGAAAGTCTCCTCAGCGCCTG
GTCTATAATGCAAAAACCTTAGCAGATGGTGTGCCATCAAGGTTCAATGGCAGTGGATCAGGAACAC
AATATTCTCTCAAGATCAATAGCCTGCAGCCTGAAGATTTTGGGATTTATTACTGTCAACATTTTTG
GAGTACTCCGCTCACGTTCGGTGCTGGGACCAAGCTGGAGCTGAAA

Light chain: Amino acids sequence (127 aa)

Leader sequence-FR1-CDR1-FR2-CDR2-FR3-CDR3-FR4

MSVLTQVLALLLLWLTGARCDIQLTQSPASLSASVGETVTITCRASDNIHKYLAWYQQKQGKSPQRL
VYNAKTLADGVPSRFNGSGSGTQYSLKINSLQPEDFGIYYCQHFWSTPLTFGAGTKLELK

Figure 11I

METHODS AND COMPOSITIONS FOR PERTUSSIS DIAGNOSIS

This application is a § 371 application of PCT/US2019/037618, filed Jun. 18, 2019, which claims priority under 35 U.S.C. § 119(e) to U.S. Provisional Patent Application No. 62/686,412, filed on Jun. 18, 2018, and U.S. Provisional Patent Application No. 62/829,802, filed on Apr. 5, 2019. The foregoing applications are incorporated by reference herein.

This invention was made with government support under grant numbers R43AI109891 and R44AI109891 awarded by the National Institutes of Health. The government has certain rights in the invention.

Incorporated herein by reference in its entirety is the Sequence Listing being concurrently submitted via EFS-Web as a text file named SeqList.txt, created Nov. 18, 2020, and having a size of 70,928 bytes.

FIELD OF THE INVENTION

This invention relates generally to the field of pertussis. Specifically, the invention provides novel compositions and methods for the early diagnosis of pertussis.

BACKGROUND OF THE INVENTION

Pertussis is a respiratory disease caused by the gram-negative bacterium *Bordetella pertussis*. It is airborne, highly contagious, and responsible for an annual 18.4 million illnesses and 254,000 deaths worldwide (Warfel, et al. (2012) J. Infect. Dis., 206(6):902-6; Mertsola, et al. (1983) J. Pediatr., 103(3):359-63; Wirsing von Konig, et al. (1998) Eur. J. Pediatr., 157(5):391-4). Globally, pertussis is one of the leading causes of death for children under 5 years old (Black, et al. (2010) Lancet 375(9730):1969-87).

Pertussis incidence in the United States has been increasing since the early 1980s (Black, S. (1997) Pediatr. Infect. Dis. J., 16(4 Suppl):S85-9; Crowcroft, et al. (2006) Lancet 367(9526):1926-36). Despite high vaccine coverage, there were still over 48,000 cases reported in the U.S. in 2012, which is the highest number since 1955 (Centers for Disease Control and Prevention (2013) MMWR Morb. Mortal Wkly. Rep., 62(33):669-82; Centers for Disease Control and Prevention (1980) MMWR Morb. Mortal Wkly. Rep., 28(54)). Moreover, reported cases represent a large underestimate of pertussis infections (Cherry, et al. (2005) Pediatr. Infect. Dis. J., 24(5 Suppl):S25-34; van den Brink, et al. (2014) BMC Infect. Dis., 14:526). Unfortunately neither vaccination nor previous infection provide life-long immunity to pertussis (Wendelboe, et al. (2005) Pediatr. Infect. Dis. J., 24(5 Suppl):S58-61). In particular, vaccine-induced immunity wanes after 4-12 years (Wendelboe, et al. (2005) Pediatr. Infect. Dis. J., 24(5 Suppl):S58-61), leaving many children and adults vulnerable to infection as well as household infants who are too young to have yet received the vaccine.

One of the largest obstacles to reducing the burden of pertussis is early diagnosis (Crowcroft, et al. (2006) Lancet 367(9526):1926-36; Cherry, et al. (2005) Pediatr. Infect. Dis. J., 24(5 Suppl):S25-34; Tondella, et al. (2009) Vaccine 27(6):803-14; Centers for Disease Control and Prevention (1997) MMWR Morb. Mortal Wkly. Rep., 46(35):822-6; Forsyth, et al. (2007) Vaccine 25(14):2634-42). Patient treatment and outbreak containment are effective, but only if initiated early (Tiwari, et al. (2005) MMWR Recomm. Rep., 54(RR-14):1-16; von Konig, C. H. (2005) Pediatr. Infect. Dis. J., 24(5 Suppl):S66-8).

However, prompt diagnosis of early pertussis is challenging because its symptoms are non-specific and because there are no assays that can rapidly diagnose pertussis at the point-of-care (POC). For example, bacterial culture, while being suitable for early diagnosis, is a very slow assay that requires 5-7 days at a site not at the point of care. Serological tests, while sensitive, cannot be used to detect early disease because patient antibodies are required. Various PCR or other DNA amplification based assays such as RT-PCR, helicase-dependent amplification (HDA) (e.g., AmpliVue® *Bordetella* Assay (Quidel, San Diego, Calif.)), nested multiplex PCR (e.g., FilmArray® Respiratory Panel (BioFire, Salt Lake City, Utah)), and loop mediated isothermal amplification (LAMP) (e.g., Illumigene® Pertussis DNA Amplification Assay (Meridian Bioscience, London, England)) are available, but have many drawbacks. Indeed, these assays: 1) can be very expensive; 2) are not point of care assays as they are generally performed in a hospital or off-site lab; and 3) do not report on the antibiotic susceptibility of the *B. pertussis*. In view of the foregoing, it is clear that improved methods for early diagnosis of pertussis are needed.

SUMMARY OF THE INVENTION

In accordance with one aspect of the instant invention, antibodies or antigen binding fragment thereof specific for tracheal colonization factor A (TcfA) are provided. In a particular embodiment, the anti-TcfA antibody or fragment thereof specifically binds amino acids 140-160, amino acids 229-240, amino acids 288-304, amino acids 286-321, amino acids 289-324, amino acids 305-323, amino acids 322-330, or amino acids 337-345 of TcfA. In a particular embodiment, the anti-TcfA antibody or fragment thereof specifically binds amino acids 140-150, amino acids 148-159, amino acids 151-156, amino acids 151-159, amino acids 229-240, amino acids 289-300, amino acids 305-312, amino acids 286-321, amino acids 289-324, amino acids 289-294, amino acids 292-300, amino acids 307-315, amino acids 310-315, amino acids 313-321, amino acids 322-330, or amino acids 337-345 of TcfA. The anti-TcfA antibodies of the instant invention may be conjugated to a detectable label such as a gold nanoparticle. Composition comprising an anti-TcfA antibody of the instant invention and a carrier are also provided.

In accordance with another aspect of the instant invention, methods of detecting *Bordetella pertussis* in a sample are provided. The methods comprise contacting the sample with an anti-TcfA antibody. Generally, the sample is a biological sample obtained from a subject. In a particular embodiment, the biological sample is a nasopharyngeal swab, aspirate, or wash.

In accordance with another aspect of the instant invention, methods for inhibiting, treating, and/or preventing pertussis and/or a *B. pertussis* infection in a subject in need thereof are provided. The methods comprise administering an anti-TcfA antibody of the instant invention to the subject. The method may further comprise administering antibiotics to the subject.

In accordance with yet another aspect of the instant invention, immunoassays for detecting *B. pertussis* are provided. The immunoassays comprise at least one anti-TcfA antibody of the instant invention. In a particular embodiment, the immunoassay is a lateral flow immunoassay test strip. In a particular embodiment, the immunoassay comprises a conjugated antibody which specifically binds amino acids 139-150 or amino acids 151-156 of TcfA. In a particular embodiment, the immunoassay comprises a test line antibody which specifically binds amino acids 289-324 of TcfA, amino acids 289-294 of TcfA, amino acids 292-300 of TcfA, and/or amino acids 322-330 of TcfA. In a particular embodiment, the immunoassay comprises a test line antibody which specifically binds amino acids 289-324, 229-240, 289-300, and/or 304-312 of TcfA (e.g., the same epitope as 13E11) and a test line antibody which specifically binds amino acids 288-304 or 292-300 (e.g., the same epitope as 14D12), particularly with a conjugated antibody which specifically binds amino acids 140-160 or 139-150 of TcfA (e.g., the same epitope as 10B1). In accordance with another aspect of the instant invention, methods of detecting Bordetella pertussis in a sample using the immunoassays are provided.

BRIEF DESCRIPTION OF THE DRAWINGS

FIG. 4 shows the reactivity of purified anti-TcfA monoclonal antibodies (mAbs) by ELISA with immobilized antigen. The immobilized antigens were formaldehyde-inactivated B. pertussis cells (Tohama I strain), recombinant TcfA containing a histidine tag, TcfA peptides (amino acids 140-160, 288-304, or 305-323) conjugated to bovine serum albumin (BSA), or control BSA. Data is the average of three independent experiments. [1]SS CM=1:128 dilution in phosphate buffered saline (PBS) pH 7.4 of clarified, 0.2 μm-filtered supernatant of B. pertussis (165 strain) Stainer-Scholte liquid cultures. [2]SS Media=1:128 dilution in PBS pH 7.4 of Stainer-Scholte uninocculated medium. Shading from dark to light indicates high to low signal.

FIG. 6 provides the amino acid sequence (SEQ ID NO: 1) of TcfA from B. pertussis. Underlined sequences are antibody epitopes.

FIGS. 11A-11I provide amino acid and nucleotide sequences of anti-TcfA antibodies. CDRs were determined by Kabat. Framework regions are underlined. FIG. 11A provides the nucleotide (SEQ ID NO: 18) and amino acid (SEQ ID NO: 19) sequences of the heavy chain and the nucleotide (SEQ ID NO: 20) and amino acid (SEQ ID NO: 21) sequences of the light chain of the 14D12 antibody. FIG. 11B provides the nucleotide (SEQ ID NO: 30) and amino acid (SEQ ID NO: 31) sequences of the heavy chain and the nucleotide (SEQ ID NO: 32) and amino acid (SEQ ID NO: 33) sequences of the light chain of the 23F8 antibody. FIG. 11C provides the nucleotide (SEQ ID NO: 42) and amino acid (SEQ ID NO: 43) sequences of the heavy chain and the nucleotide (SEQ ID NO: 44) and amino acid (SEQ ID NO: 45) sequences of the light chain of the 18B2 antibody. FIG. 11D provides the nucleotide (SEQ ID NO: 54) and amino acid (SEQ ID NO: 55) sequences of the heavy chain and the nucleotide (SEQ ID NO: 56) and amino acid (SEQ ID NO: 57) sequences of the light chain of the 20F4 antibody. FIG. 11E provides the nucleotide (SEQ ID NO: 66) and amino acid (SEQ ID NO: 67) sequences of the heavy chain and the nucleotide (SEQ ID NO: 68) and amino acid (SEQ ID NO: 69) sequences of the light chain of the 14G11 antibody. FIG. 11F provides the nucleotide (SEQ ID NO: 78) and amino acid (SEQ ID NO: 79) sequences of the heavy chain and the nucleotide (SEQ ID NO: 80) and amino acid (SEQ ID NO: 81) sequences of the light chain of the 13E11 antibody. FIG. 11G provides the nucleotide (SEQ ID NO: 90) and amino acid (SEQ ID NO: 91) sequences of the heavy chain and the nucleotide (SEQ ID NO: 92) and amino acid (SEQ ID NO: 93) sequences of the light chain of the 10B1 antibody. FIG. 11H provides the nucleotide (SEQ ID NO: 102) and amino acid (SEQ ID NO: 103) sequences of the heavy chain and the nucleotide (SEQ ID NO: 104) and amino acid (SEQ ID NO: 105) sequences of the light chain of the 7E11 antibody. FIG. 11I provides the nucleotide (SEQ ID NO: 114) and amino acid (SEQ ID NO: 115) sequences of the heavy chain and the nucleotide (SEQ ID NO: 116) and amino acid (SEQ ID NO: 117) sequences of the light chain of the 3E6 antibody.

DETAILED DESCRIPTION OF THE INVENTION

Figure 1:
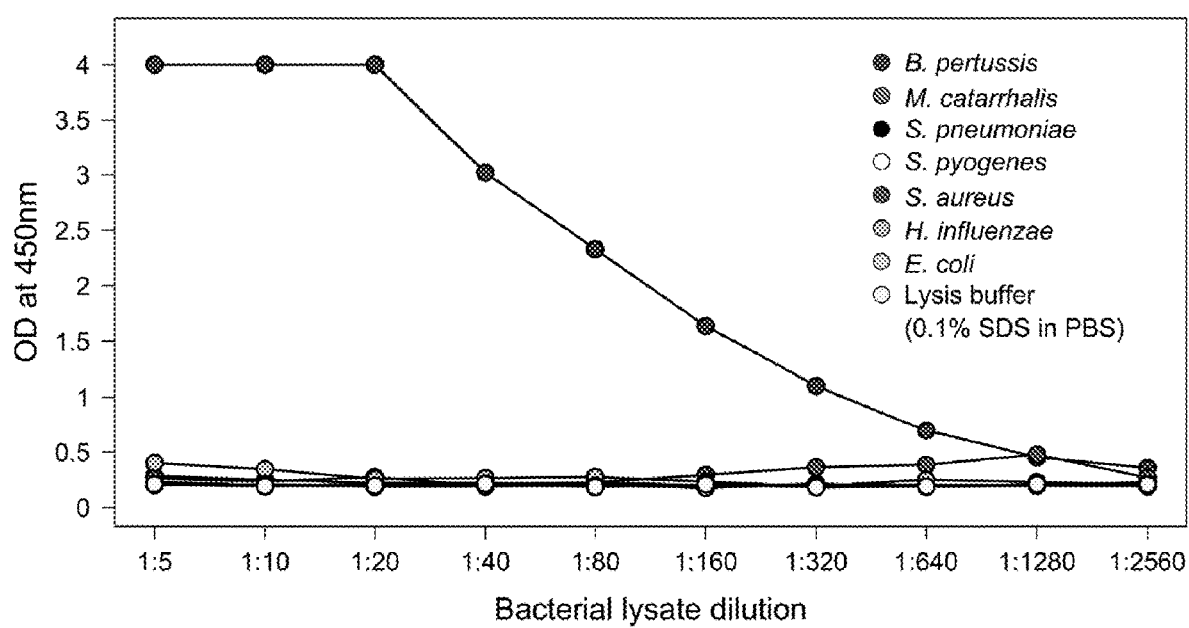
FIG. 1 provides a graph of an enzyme-linked immunosorbent assay (ELISA) using anti-tracheal colonization factor A (TcfA) antibodies against lysates of Bordetella pertussis, Moraxella catarrhalis, Streptococcus pneumoniae, Streptococcus pyogenes, Staphylococcus aureus, Haemophilus influenza, Escherichia coli, or a negative control (lysis buffer) at the indicated dilutions.
Figure 2:
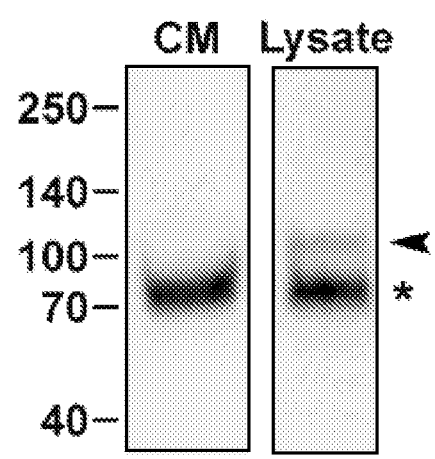
FIG. 2 provides images of a Western blot analysis using anti-TcfA antibodies on B. pertussis conditioned media (CM) and B. pertussis lysates. * indicates secreted TcfA isoform and arrowhead indicates cell-associated TcfA isoform.
Figure 3A:
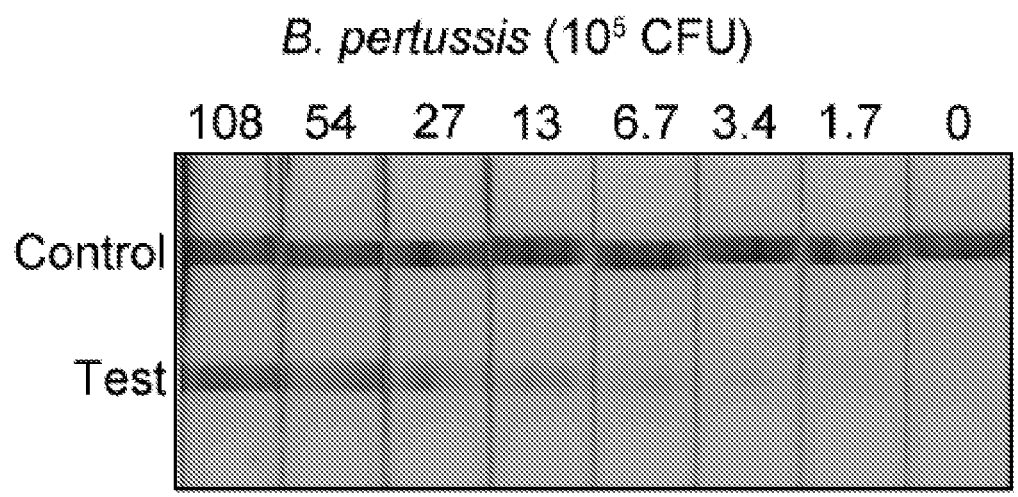
FIG. 3A provides an image of a lateral flow immunoassay (LFI) using polyclonal anti-TcfA antibodies. The amount of B. pertussis colony forming units (CFUs) is indicated.
Figure 3B:
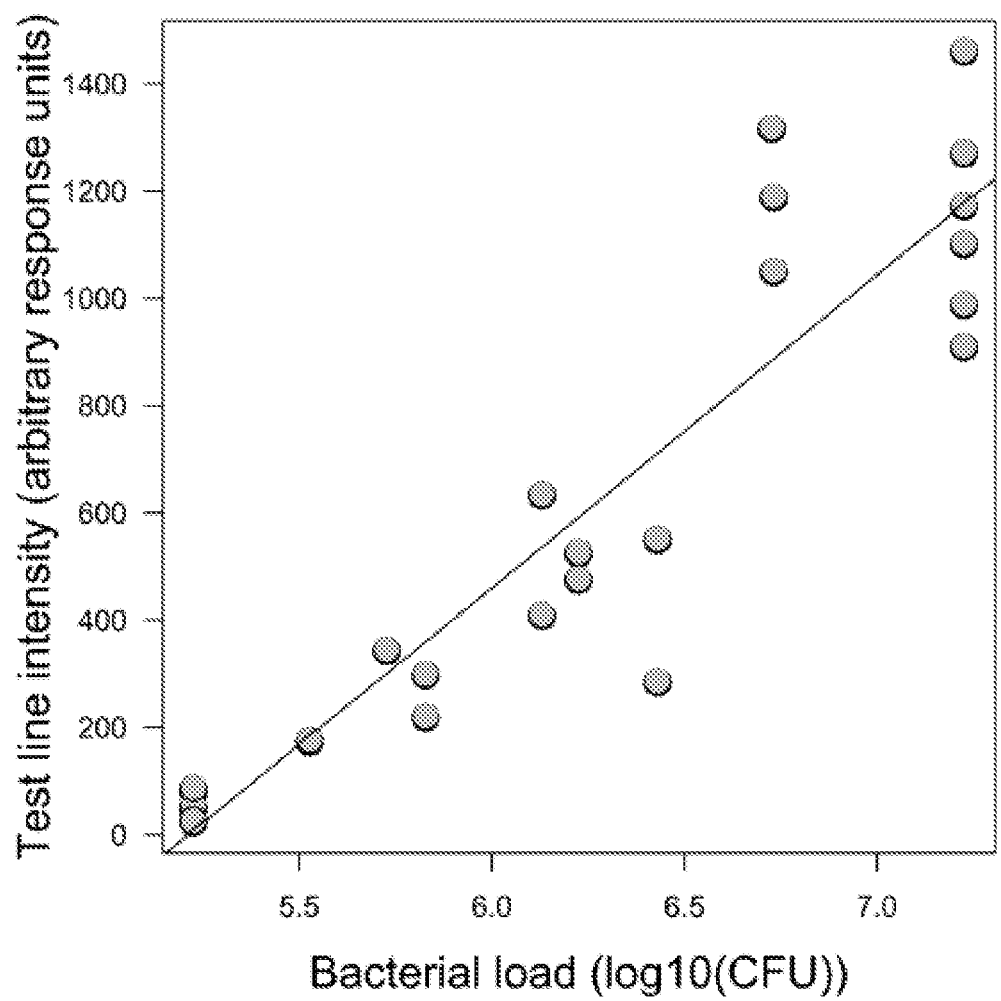
FIG. 3B provides a graph of a quantitative limit of detection analysis of the lateral flow immunoassay (LFI) using anti-TcfA antibodies. The amount of B. pertussis colony forming units (CFUs) is indicated versus the band intensity.

Herein, a point-of-care, lateral flow immunoassay (LFI) diagnostic for early pertussis that enables immediate treatment initiation (e.g., during the patient's initial clinic visit) is provided. This point-of-care assay for detection of early pertussis will improve patient care and public health. It is well established that disease severity and duration can be reduced with pertussis if patients receive antibiotic treatment early (Tiwari, et al. (2005) MMWR Recomm. Rep., 54(RR-14):1-16; von Konig, C. H. (2005) Pediatr. Infect. Dis. J., 24(5 Suppl):S66-8; Mattoo, et al. (2005) Clin. Microbiol. Rev., 18(2):326-82; Hewlet, et al. (2005) N. Engl. J. Med., 352(12):1215-22). For infants, early diagnosis would also save lives. Currently, infants require more doctor visits to reach a pertussis diagnosis than do older patients (Lee, et al. (2000) Arch. Fam. Med., 9(10):989-96). Infants also have the highest risk of mortality and severe neurological complications (Tanaka, et al. (2003) JAMA 290(22):2968-75). For infants, early diagnosis would enable not only earlier treatment with antibiotics, but also key supportive care for dehydration and malnutrition (Crowcroft, et al. (2006) Lancet 367(9526):1926-36; Hewlet, et al. (2005) N. Engl. J. Med., 352(12):1215-22).

Early diagnosis can change the course of an outbreak because patients are most infectious from the start of non-specific symptoms until three weeks after paroxysmal cough onset (Tiwari, et al. (2005) MMWR Recomm. Rep., 54(RR-14):1-16). Antibiotic treatment eliminates culturable bacteria from the nasopharynx (Bergquist, et al. (1987) Pediatr. Infect. Dis. J., 6(5):458-61), which decreases the patients' infectious period and limits transmission (Wirsing von Konig, et al. (1998) Eur. J. Pediatr., 157(5):391-4). Moreover, once patients are diagnosed, their close contacts can receive prophylactic antibiotics (Tiwari, et al. (2005) MMWR Recomm. Rep., 54(RR-14):1-16; von Konig, C. H. (2005) Pediatr. Infect. Dis. J., 24(5 Suppl):S66-8). Thus, early diagnosis would reduce the size of pertussis outbreaks.

Minimizing outbreak size through early diagnosis would also reduce the economic burden of pertussis. More than $17 billion were spent on pertussis costs (direct and indirect) from 2001-2010 in the U.S. (Purdy, et al. (2004) Clin. Infect. Dis., 39(1):20-8). Preventing infant cases is particularly important because 70% of infants with pertussis become hospitalized (Tanaka, et al. (2003) JAMA 290(22):2968-75) and each infant hospital stay costs an average of $10,000, excluding outpatient direct and societal indirect costs (O'Brien, et al. (2005) BMC Infect. Dis., 5:57).

In accordance with one aspect of the instant invention, anti-tracheal colonization factor A (TcfA) antibodies and fragments thereof are provided. The anti-TcfA antibodies may be monoclonal or polyclonal. In a particular embodiment, the antibody or fragment thereof is immunologically specific for TcfA of *Bordetella pertussis* (e.g., Tohama I strain). Amino acid and nucleotide sequences of TcfA are provided in GenBank Accession No. NP_879974 and Gene ID: 2666888. FIG. 6 provides an amino acid sequence for TcfA (SEQ ID NO: 1) and certain anti-TcfA antibody epitopes. The anti-TcfA antibodies or fragments thereof may recognize a linear epitope or a conformational epitope, particularly a linear epitope. In a particular embodiment, the anti-TcfA antibody or fragment thereof recognizes a linear epitope. In a particular embodiment, the anti-TcfA antibody or fragment thereof is immunologically specific for a polypeptide comprising amino acids 140-160, amino acids 288-304, amino acids 305-323, amino acids 322-330, or amino acids 337-345 of TcfA. In a particular embodiment, the anti-TcfA antibody or fragment thereof is immunologically specific for a polypeptide comprising amino acids 139-150, amino acids 148-159, amino acids 151-156, amino acids 151-159, amino acids 229-240, amino acids 289-300, amino acids 304-312, amino acids 286-321, amino acids 289-324, amino acids 289-294, amino acids 292-300, amino acids 307-315, amino acids 310-315, amino acids 313-321, amino acids 322-330, or amino acids 337-345 of TcfA. The above epitopes may be longer or shorter than the above identified sequences by 0, 1, 2, 3, 4, 5, 6, 7, 8, 9, 10, or more amino acids, particularly 1, 2, 3, 4, or 5 amino acids, at the N-terminus and/or C-terminus of the sequence. In another embodiment, the above epitopes have at least 90%, 95%, 97%, 99%, or 100% homology or identity with the sequence provided in FIG. 6 (SEQ ID NO: 1). Antibodies which bind the same epitope as an antibody provided herein are also encompassed by the instant invention.

In a particular embodiment, the anti-TcfA antibody or fragment thereof is immunologically specific for amino acids 288-304 or 292-300 of TcfA. In a particular embodiment, the anti-TcfA antibody is 14D12 (as depicted in FIG. 11A), optionally wherein the signal peptides removed, or a fragment thereof. In a particular embodiment, the anti-TcfA antibody comprises a heavy chain comprising SEQ ID NO: 19 and/or a light chain comprising SEQ ID NO: 21. In a particular embodiment, the anti-TcfA antibody comprises a heavy chain comprising: EVMLVESG-GALVKPGGSLKLSCAASGITFSNYAMSWIRQTPEKR-LEWV ASISSGGSYIYYSDSVKGRFTISRDNARN-TLNLQMSSLRSEDTAMYYCVRGAH GNFDYWGQGTTLTVSS (SEQ ID NO: 22) and/or a light chain comprising: DIVLTQSPASLAVSLGQRATISCRT-SETVDYDGDSYMNWYQQKSGQP PKLLISGASN-VESGVPARFSGSGSGTDFSLNIIIPVEED-DITMYFCQQNRKLPYT FGSGTKLEMK (SEQ ID NO: 23). In a particular embodiment, the anti-TcfA antibody or fragment thereof comprises one, two, three, four, five, or all six complementarity determining regions (CDRs) of 14D12 (e.g., as determined by IMGT, Chothia, Kabat, Martin (e.g., enhanced Chothia) or AHo numbering scheme, particularly Kabat). In a particular embodiment, the anti-TcfA antibody or fragment thereof comprises one, two, three, four, five, or all six CDRs depicted in FIG. 11A. In a particular embodiment, the anti-TcfA antibody or fragment thereof comprises a heavy chain comprising one, two, or all three CDRs depicted in the heavy chain provided in FIG. 11A. In a particular embodiment, the anti-TcfA antibody or fragment thereof comprises a light chain comprising one, two, or all three CDRs depicted in the light chain provided in FIG. 11A. In a particular embodiment, the anti-TcfA antibody or fragment thereof comprises one, two, three, four, five, or all six of: NYAMS (SEQ ID NO: 24), SISSGGSYIYYSDSVKG (SEQ ID NO: 25), GAHGNFDY (SEQ ID NO: 26), RTSETVDYDGDSYMN (SEQ ID NO: 27), GASNVES (SEQ ID NO: 28), and QQNRKLPYT (SEQ ID NO: 29). In a particular embodiment, the anti-TcfA antibody or fragment thereof comprises a heavy chain comprising one, two, or all three of: NYAMS (SEQ ID NO: 24), SISSGGSYIYYSDSVKG (SEQ ID NO: 25), and GAHGNFDY (SEQ ID NO: 26) and/or a light chain comprising one, two, or all three of: RTSETVDYDGDSYMN (SEQ ID NO: 27), GASNVES (SEQ ID NO: 28), and QQNRKLPYT (SEQ ID NO: 29). In another embodiment, the anti-TcfA antibody or fragment thereof comprise an amino acid sequence having at least 90%, 95%, 97%, 99%, or 100% homology or identity with any of the sequences provided above (e.g., any of SEQ ID NOs: 19 and 22-29).

In a particular embodiment, the anti-TcfA antibody or fragment thereof is immunologically specific for amino acids 288-304 or 292-300 of TcfA. In a particular embodiment, the anti-TcfA antibody is 23F8 (as depicted in FIG. 11), optionally wherein the signal peptides removed, or a fragment thereof. In a particular embodiment, the anti-TcfA antibody comprises a heavy chain comprising SEQ ID NO: 31 and/or a light chain comprising SEQ ID NO: 33. In a particular embodiment, the anti-TcfA antibody comprises a heavy chain comprising: EVQLVESGGGLVKPGGSRKLSCAASGFTFSDYGMHWVRQAPEKGLEWV AYISSGSRTIYYADTVKGRFTISRDNAKNTLFLQMTSLRSEDTAMYYCARLGY GYDWYFDVWGTGTTVTVSS (SEQ ID NO: 34) and/or a light chain comprising: DVVMTQTPLTLSVTIGQPASISCKSSQSLLDSDGRTYLNWLLQRPGQS PKRLIYLVSKLDSGVPDRFTGSGSGTDFTLKISRVEAEDLGIYYCWQGTHFPQ TFGGGTKLEIK (SEQ ID NO: 35). In a particular embodiment, the anti-TcfA antibody or fragment thereof comprises one, two, three, four, five, or all six CDRs of 23F8 (e.g., as determined by IMGT, Chothia, Kabat, Martin (e.g., enhanced Chothia) or AHo numbering scheme, particularly Kabat). In a particular embodiment, the anti-TcfA antibody or fragment thereof comprises one, two, three, four, five, or all six CDRs depicted in FIG. 11B. In a particular embodiment, the anti-TcfA antibody or fragment thereof comprises a heavy chain comprising one, two, or all three CDRs depicted in the heavy chain provided in FIG. 11B. In a particular embodiment, the anti-TcfA antibody or fragment thereof comprises a light chain comprising one, two, or all three CDRs depicted in the light chain provided in FIG. 11B. In a particular embodiment, the anti-TcfA antibody or fragment thereof comprises one, two, three, four, five, or all six of: DYGMH (SEQ ID NO: 36), YISSGSRTIYYADTVKG (SEQ ID NO: 37), LGYGYDWYFDV (SEQ ID NO: 38), KSSQSLLDSDGRTYLN (SEQ ID NO: 39), LVSKLDS (SEQ ID NO: 40), and WQGTHFPQT (SEQ ID NO: 41). In a particular embodiment, the anti-TcfA antibody or fragment thereof comprises a heavy chain comprising one, two, or all three of: DYGMH (SEQ ID NO: 36), YISSGSRTIYYADTVKG (SEQ ID NO: 37), and LGYGYDWYFDV (SEQ ID NO: 38) and/or a light chain comprising one, two, or all three of: KSSQSLLDSDGRTYLN (SEQ ID NO: 39), LVSKLDS (SEQ ID NO: 40), and WQGTHFPQT (SEQ ID NO: 41). In another embodiment, the anti-TcfA antibody or fragment thereof comprise an amino acid sequence having at least 90%, 95%, 97%, 99%, or 100% homology or identity with any of the sequences provided above (e.g., any of SEQ ID NOs: 31 and 33-41).

In a particular embodiment, the anti-TcfA antibody or fragment thereof is immunologically specific for amino acids 337-345 of TcfA. In a particular embodiment, the anti-TcfA antibody is 18B2 (as depicted in FIG. 11C), optionally wherein the signal peptides removed, or a fragment thereof. In a particular embodiment, the anti-TcfA antibody comprises a heavy chain comprising SEQ ID NO: 43 and/or a light chain comprising SEQ ID NO: 45. In a particular embodiment, the anti-TcfA antibody comprises a heavy chain comprising: QVQLQQSGAELVRPGTSVKMSCKAAGYTFTNYWIGWVKQRPGHGLEWI GDIYPGGVYTNYNENFKGKATLTADTSSSTAHMQLSSLTSEDSAIYYCVRGG KYGNFFAMDYWGQGTSVTVSS (SEQ ID NO: 46) and/or a light chain comprising: DIVITQDELSNPVTSGESVSISCRSSKSLLYKDGKTYLNWFLQRPGQ SPQLLIYLMSTRASGVSDRFSGSGSGTDFTLEISRVKAEDVGVYYCQQLVEYP FTFGSGTKLEIK (SEQ ID NO: 47). In a particular embodiment, the anti-TcfA antibody or fragment thereof comprises one, two, three, four, five, or all six CDRs of 18B2 (e.g., as determined by IMGT, Chothia, Kabat, Martin (e.g., enhanced Chothia) or AHo numbering scheme, particularly Kabat). In a particular embodiment, the anti-TcfA antibody or fragment thereof comprises one, two, three, four, five, or all six CDRs depicted in FIG. 11C. In a particular embodiment, the anti-TcfA antibody or fragment thereof comprises a heavy chain comprising one, two, or all three CDRs depicted in the heavy chain provided in FIG. 11C. In a particular embodiment, the anti-TcfA antibody or fragment thereof comprises a light chain comprising one, two, or all three CDRs depicted in the light chain provided in FIG. 11C. In a particular embodiment, the anti-TcfA antibody or fragment thereof comprises one, two, three, four, five, or all six of: NYWIG (SEQ ID NO: 48), DIYPGGVYTNYNENFKG (SEQ ID NO: 49), GGKYGNFFAMDY (SEQ ID NO: 50), RSSKSLLYKDGKTYLN (SEQ ID NO: 51), LMSTRAS (SEQ ID NO: 52), and QQLVEYPFT (SEQ ID NO: 53). In a particular embodiment, the anti-TcfA antibody or fragment thereof comprises a heavy chain comprising one, two, or all three of: NYWIG (SEQ ID NO: 48), DIYPGGVYTNYNENFKG (SEQ ID NO: 49), and GGKYGNFFAMDY (SEQ ID NO: 50) and/or a light chain comprising one, two, or all three of: RSSKSLLYKDGKTYLN (SEQ ID NO: 51), LMSTRAS (SEQ ID NO: 52), and QQLVEYPFT (SEQ ID NO: 53). In another embodiment, the anti-TcfA antibody or fragment thereof comprise an amino acid sequence having at least 90%, 95%, 97%, 99%, or 100% homology or identity with any of the sequences provided above (e.g., any of SEQ ID NOs: 43 and 45-53).

In a particular embodiment, the anti-TcfA antibody or fragment thereof is immunologically specific for amino acids 305-323 or 307-315 of TcfA. In a particular embodiment, the anti-TcfA antibody is 20F4 (as depicted in FIG. 11D), optionally wherein the signal peptides removed, or a fragment thereof. In a particular embodiment, the anti-TcfA antibody comprises a heavy chain comprising SEQ ID NO: 55 and/or a light chain comprising SEQ ID NO: 57. In a particular embodiment, the anti-TcfA antibody comprises a heavy chain comprising: QIQLVQSGPELKKPGETVKISCKASGYTFTNYGMNWVKQAPGKGLKWM GWINTYTGEPTYADDFKGRFAFSLETSATTAY- LQINNLKNEDTATYFCARAA TGYFDYWGQGT-TLTVSS (SEQ ID NO: 58) and/or a light chain comprising: DIVMSQSPSSLAVSAGEKVTMSCKSSQSLLYSSNQK-NYLAWYQQKPG QSPKLLIYWAST-RESGVPDRFTGSGSGTDFTLTISSVKAED-LAVYYCQQYYNE YTFGGGTKLEIK (SEQ ID NO: 59). In a particular embodiment, the anti-TcfA antibody or fragment thereof comprises one, two, three, four, five, or all six CDRs of 20F4 (e.g., as determined by IMGT, Chothia, Kabat, Martin (e.g., enhanced Chothia) or AHo numbering scheme, particularly Kabat). In a particular embodiment, the anti-TcfA antibody or fragment thereof comprises one, two, three, four, five, or all six CDRs depicted in FIG. 11D. In a particular embodiment, the anti-TcfA antibody or fragment thereof comprises a heavy chain comprising one, two, or all three CDRs depicted in the heavy chain provided in FIG. 11D. In a particular embodiment, the anti-TcfA antibody or fragment thereof comprises a light chain comprising one, two, or all three CDRs depicted in the light chain provided in FIG. 11D. In a particular embodiment, the anti-TcfA antibody or fragment thereof comprises one, two, three, four, five, or all six of: NYGMN (SEQ ID NO: 60), WINTYT-GEPTYADDFKG (SEQ ID NO: 61), AATGYFDY (SEQ ID NO: 62), KSSQSLLYSSNQKNYLA (SEQ ID NO: 63), WASTRES (SEQ ID NO: 64), and QQYYNEYT (SEQ ID NO: 65). In a particular embodiment, the anti-TcfA antibody or fragment thereof comprises a heavy chain comprising one, two, or all three of: NYGMN (SEQ ID NO: 60), WINTYTGEPTYADDFKG (SEQ ID NO: 61), and AATGYFDY (SEQ ID NO: 62) and/or a light chain comprising one, two, or all three of: KSSQSLLYSSNQKNYLA (SEQ ID NO: 63), WASTRES (SEQ ID NO: 64), and QQYYNEYT (SEQ ID NO: 65). In another embodiment, the anti-TcfA antibody or fragment thereof comprise an amino acid sequence having at least 90%, 95%, 97%, 99%, or 100% homology or identity with any of the sequences provided above (e.g., any of SEQ ID NOs: 55 and 57-65).

In a particular embodiment, the anti-TcfA antibody or fragment thereof is immunologically specific for amino acids 305-323 or 313-321 of TcfA. In a particular embodiment, the anti-TcfA antibody is 14G11 (as depicted in FIG. 11E), optionally wherein the signal peptides removed, or a fragment thereof. In a particular embodiment, the anti-TcfA antibody comprises a heavy chain comprising SEQ ID NO: 67 and/or a light chain comprising SEQ ID NO: 69. In a particular embodiment, the anti-TcfA antibody comprises a heavy chain comprising: EVKLVESGGGLVQPGGSLSLS-CAASGFTFTDYYMSWVRQPPGKALEWL GFIRNK-ANGYTTEYSASVKGRFTISRDNSQSILYLQMNAL-RAEDSATYYCARY RRDYYGSLNYYTMD YWGQGTSVTVSS (SEQ ID NO: 70) and/or a light chain comprising: DIQMTQSPASLSASVGETVTITCRASENIY-SYLAWYQQKQGKSPQLL VYNAKTLAE-GVPSRFSGSGSGTQFSLKINSLQPEDFGSYYCQNHY-GIPLTFGA GTKLELK (SEQ ID NO: 71). In a particular embodiment, the anti-TcfA antibody or fragment thereof comprises one, two, three, four, five, or all six CDRs of 14G11 (e.g., as determined by IMGT, Chothia, Kabat, Martin (e.g., enhanced Chothia) or AHo numbering scheme, particularly Kabat). In a particular embodiment, the anti-TcfA antibody or fragment thereof comprises one, two, three, four, five, or all six CDRs depicted in FIG. 11E. In a particular embodiment, the anti-TcfA antibody or fragment thereof comprises a heavy chain comprising one, two, or all three CDRs depicted in the heavy chain provided in FIG. 11E. In a particular embodiment, the anti-TcfA antibody or fragment thereof comprises a light chain comprising one, two, or all three CDRs depicted in the light chain provided in FIG. 11E. In a particular embodiment, the anti-TcfA antibody or fragment thereof comprises one, two, three, four, five, or all six of: DYYMS (SEQ ID NO: 72), FIRNK-ANGYTTEYSASVKG (SEQ ID NO: 73), YRRDYYGSLNYYTMDY (SEQ ID NO: 74), RASENIY-SYLA (SEQ ID NO: 75), NAKTLAE (SEQ ID NO: 76), and QNHYGIPLT (SEQ ID NO: 77). In a particular embodiment, the anti-TcfA antibody or fragment thereof comprises a heavy chain comprising one, two, or all three of: DYYMS (SEQ ID NO: 72), FIRNKANGYTTEYSASVKG (SEQ ID NO: 73), and YRRDYYGSLNYYTMDY (SEQ ID NO: 74) and/or a light chain comprising one, two, or all three of: RASENIYSYLA (SEQ ID NO: 75), NAKTLAE (SEQ ID NO: 76), and QNHYGIPLT (SEQ ID NO: 77). In another embodiment, the anti-TcfA antibody or fragment thereof comprise an amino acid sequence having at least 90%, 95%, 97%, 99%, or 100% homology or identity with any of the sequences provided above (e.g., any of SEQ ID NOs: 67 and 69-77).

In a particular embodiment, the anti-TcfA antibody or fragment thereof is immunologically specific for amino acids 288-323, 229-240, 289-300, and/or 304-312 of TcfA. In a particular embodiment, the anti-TcfA antibody is 13E11 (as depicted in FIG. 11F), optionally wherein the signal peptides removed, or a fragment thereof. In a particular embodiment, the anti-TcfA antibody comprises a heavy chain comprising SEQ ID NO: 79 and/or a light chain comprising SEQ ID NO: 81. In a particular embodiment, the anti-TcfA antibody comprises a heavy chain comprising: EVQLVESGGGLVKPGGSRKLS-CAASGFTFSDYGMHWVRQAPEKGLEWV AYIS-SGSSTIYYADTVKGRFTISRDNAKNTLFLQMT-SLRSEDTAMYYCARPRS GRYFDYWGQGTTLTVSS (SEQ ID NO: 82) and/or a light chain comprising: DVMMTQTPLTLSVTIGQPASISCKSSQSLLDSNGN-TYLHWLLQRPGQS PKILIYLVSK-LDSGVPDRFSGSGSGTDFTLKISRVEAEDLGVYY-CLQGTHFPYT FGGGTKLEIK (SEQ ID NO: 83). In a particular embodiment, the anti-TcfA antibody or fragment thereof comprises one, two, three, four, five, or all six CDRs of 13E11 (e.g., as determined by IMGT, Chothia, Kabat, Martin (e.g., enhanced Chothia) or AHo numbering scheme, particularly Kabat). In a particular embodiment, the anti-TcfA antibody or fragment thereof comprises one, two, three, four, five, or all six CDRs depicted in FIG. 11F. In a particular embodiment, the anti-TcfA antibody or fragment thereof comprises a heavy chain comprising one, two, or all three CDRs depicted in the heavy chain provided in FIG. 11F. In a particular embodiment, the anti-TcfA antibody or fragment thereof comprises a light chain comprising one, two, or all three CDRs depicted in the light chain provided in FIG. 11F. In a particular embodiment, the anti-TcfA antibody or fragment thereof comprises one, two, three, four, five, or all six of: DYGMH (SEQ ID NO: 84), YIS-SGSSTIYYADTVKG (SEQ ID NO: 85), PRSGRYFDY (SEQ ID NO: 86), KSSQSLLDSNGNTYLH (SEQ ID NO: 87), LVSKLDS (SEQ ID NO: 88), and LQGTHFPYT (SEQ ID NO: 89). In a particular embodiment, the anti-TcfA antibody or fragment thereof comprises a heavy chain comprising one, two, or all three of: DYGMH (SEQ ID NO: 84), YISSGSSTIYYADTVKG (SEQ ID NO: 85), and PRS-GRYFDY (SEQ ID NO: 86) and/or a light chain comprising one, two, or all three of: KSSQSLLDSNGNTYLH (SEQ ID NO: 87), LVSKLDS (SEQ ID NO: 88), and LQGTHFPYT (SEQ ID NO: 89). In another embodiment, the anti-TcfA antibody or fragment thereof comprise an amino acid sequence having at least 90%, 95%, 97%, 99%, or 100% homology or identity with any of the sequences provided above (e.g., any of SEQ ID NOs: 79 and 81-89).

In a particular embodiment, the anti-TcfA antibody or fragment thereof is immunologically specific for amino acids 140-160 or 139-150 of TcfA. In a particular embodiment, the anti-TcfA antibody is 10B1 (as depicted in FIG. 11G), optionally wherein the signal peptides removed, or a fragment thereof. In a particular embodiment, the anti-TcfA antibody comprises a heavy chain comprising SEQ ID NO: 91 and/or a light chain comprising SEQ ID NO: 93. In a particular embodiment, the anti-TcfA antibody comprises a heavy chain comprising: EVQLQQSGAELVKP-GASVKLSCTASGFNIKDTYIHWVKQRPEQGLEWI GRIDPANGNTIYASKFQGKAPITAVTSSN-TAYMQFSSLTSGDTAVYYCTAMD YWGQGTSVTVSS (SEQ ID NO: 94) and/or a light chain comprising: DVVMTQTPLTLSVTIGQPASISCK-SSQSLLHSNGKTYLNWLLQRPGQS PKLLIYLVSK-LDSGVPDRFSGSGSGTDFTLKISRVEAEDLGVYY-CLQATHFPHT FGSGTKLEIK (SEQ ID NO: 95). In a particular embodiment, the anti-TcfA antibody or fragment thereof comprises one, two, three, four, five, or all six CDRs of 10B1 (e.g., as determined by IMGT, Chothia, Kabat, Martin (e.g., enhanced Chothia) or AHo numbering scheme, particularly Kabat). In a particular embodiment, the anti-TcfA antibody or fragment thereof comprises one, two, three, four, five, or all six CDRs depicted in FIG. 11G. In a particular embodiment, the anti-TcfA antibody or fragment thereof comprises a heavy chain comprising one, two, or all three CDRs depicted in the heavy chain provided in FIG. 11G. In a particular embodiment, the anti-TcfA antibody or fragment thereof comprises a light chain comprising one, two, or all three CDRs depicted in the light chain provided in FIG. 11G. In a particular embodiment, the anti-TcfA antibody or fragment thereof comprises one, two, three, four, five, or all six of: DTYIH (SEQ ID NO: 96), RIDPANGN-TIYASKFQG (SEQ ID NO: 97), MDY (SEQ ID NO: 98), KSSQSLLHSNGKTYLN (SEQ ID NO: 99), LVSKLDS (SEQ ID NO: 100), and LQATHFPHT (SEQ ID NO: 101). In a particular embodiment, the anti-TcfA antibody or fragment thereof comprises a heavy chain comprising one, two, or all three of: DTYIH (SEQ ID NO: 96), RIDPANGNTI-YASKFQG (SEQ ID NO: 97), and MDY (SEQ ID NO: 98) and/or a light chain comprising one, two, or all three of: KSSQSLLHSNGKTYLN (SEQ ID NO: 99), LVSKLDS (SEQ ID NO: 100), and LQATHFPHT (SEQ ID NO: 101). In another embodiment, the anti-TcfA antibody or fragment thereof comprise an amino acid sequence having at least 90%, 95%, 97%, 99%, or 100% homology or identity with any of the sequences provided above (e.g., any of SEQ ID NOs: 91 and 93-101).

In a particular embodiment, the anti-TcfA antibody or fragment thereof is immunologically specific for amino acids 140-160 or 139-150 of TcfA. In a particular embodiment, the anti-TcfA antibody is 7E11 (as depicted in FIG. 11H), optionally wherein the signal peptides removed, or a fragment thereof. In a particular embodiment, the anti-TcfA antibody comprises a heavy chain comprising SEQ ID NO: 103 and/or a light chain comprising SEQ ID NO: 105. In a particular embodiment, the anti-TcfA antibody comprises a heavy chain comprising: EVQLQQSGAELVKP-GASVKLSCTASGFNIKDTYIHWVKQRPEQGLEWI GRIDPANGNIIYASKFQGEATITADTSSN-TAYMQLSSLTSGDTAVYYCSAMDY WGQGTSVTVSS (SEQ ID NO: 106) and/or a light chain comprising: DVVMTQTPLTLSLTIGQPASISCK-SSQSLLHSNGKTYLNWLLQRPGQS PKLLIYLVSK-LDSGVPDRFSGSGSGTDFTLKISRVEAEDLGVYY-CLQATHFPHT FGSGTKLEIK (SEQ ID NO: 107). In a particular embodiment, the anti-TcfA antibody or fragment thereof comprises one, two, three, four, five, or all six CDRs of 7E11 (e.g., as determined by IMGT, Chothia, Kabat, Martin (e.g., enhanced Chothia) or AHo numbering scheme, particularly Kabat). In a particular embodiment, the anti-TcfA antibody or fragment thereof comprises one, two, three, four, five, or all six CDRs depicted in FIG. 11H. In a particular embodiment, the anti-TcfA antibody or fragment thereof comprises a heavy chain comprising one, two, or all three CDRs depicted in the heavy chain provided in FIG. 11H. In a particular embodiment, the anti-TcfA antibody or fragment thereof comprises a light chain comprising one, two, or all three CDRs depicted in the light chain provided in FIG. 11H. In a particular embodiment, the anti-TcfA antibody or fragment thereof comprises one, two, three, four, five, or all six of: DTYIH (SEQ ID NO: 108), RIDPANG-NIIYASKFQG (SEQ ID NO: 109), MDY (SEQ ID NO: 110), KSSQSLLHSNGKTYLN (SEQ ID NO: 111), LVSK-LDS (SEQ ID NO: 112), and LQATHFPHT (SEQ ID NO: 113). In a particular embodiment, the anti-TcfA antibody or fragment thereof comprises a heavy chain comprising one, two, or all three of: DTYIH (SEQ ID NO: 108), RIDPANG-NIIYASKFQG (SEQ ID NO: 109), and MDY (SEQ ID NO: 110) and/or a light chain comprising one, two, or all three of: KSSQSLLHSNGKTYLN (SEQ ID NO: 111), LVSKLDS (SEQ ID NO: 112), and LQATHFPHT (SEQ ID NO: 113). In another embodiment, the anti-TcfA antibody or fragment thereof comprise an amino acid sequence having at least 90%, 95%, 97%, 99%, or 100% homology or identity with any of the sequences provided above (e.g., any of SEQ ID NOs: 103 and 105-113).

In a particular embodiment, the anti-TcfA antibody or fragment thereof is immunologically specific for amino acids 140-160 or 151-156 of TcfA. In a particular embodiment, the anti-TcfA antibody is 3E6 (as depicted in FIG. 11I), optionally wherein the signal peptides removed, or a fragment thereof. In a particular embodiment, the anti-TcfA antibody comprises a heavy chain comprising SEQ ID NO: 115 and/or a light chain comprising SEQ ID NO: 117. In a particular embodiment, the anti-TcfA antibody comprises a heavy chain comprising: EVKLVESGGGLVQPGGSLRLS-CATSGFTFTDYYMSWVRQPPGKALEWM GFIRNKAKGYTTDYSASVKGRFTISRDDSQSI-LYLQMNTLRPEDSATYYCARN YDYSMDYWGQGTSVTVSS (SEQ ID NO: 118) and/or a light chain comprising: DIQLTQSPASLSASVGETVTIT-CRASDNIIKYLAWYQQKQGKSPQRL VYNAKT-LADGVPSRFNGSGSGTQYSLKIN-SLQPEDFGIYYCQHFWSTPLTFGA GTKLELK (SEQ ID NO: 119). In a particular embodiment, the anti-TcfA antibody or fragment thereof comprises one, two, three, four, five, or all six CDRs of 3E6 (e.g., as determined by IMGT, Chothia, Kabat, Martin (e.g., enhanced Chothia) or AHo numbering scheme, particularly Kabat). In a particular embodiment, the anti-TcfA antibody or fragment thereof comprises one, two, three, four, five, or all six CDRs depicted in FIG. 11I. In a particular embodiment, the anti-TcfA antibody or fragment thereof comprises a heavy chain comprising one, two, or all three CDRs depicted in the heavy chain provided in FIG. 11I. In a particular embodiment, the anti-TcfA antibody or fragment thereof comprises a light chain comprising one, two, or all three CDRs depicted in the light chain provided in FIG. 11I. In a particular embodiment, the anti-TcfA antibody or fragment thereof comprises one, two, three, four, five, or all six of: DYYMS (SEQ ID NO: 120), FIRNKAKGYTTDYSASVKG (SEQ ID NO: 121), NYDYSMDY (SEQ ID NO: 122), RASDNIHKYLA (SEQ ID NO: 123), NAKTLAD (SEQ ID NO: 124), and QHFWSTPLT (SEQ ID NO: 125). In a particular embodiment, the anti-TcfA antibody or fragment thereof comprises a heavy chain comprising one, two, or all three of: DYYMS (SEQ ID NO: 120), FIRNKAKGYTTDYSASVKG (SEQ ID NO: 121), and NYDYSMDY (SEQ ID NO: 122) and/or a light chain comprising one, two, or all three of: RASDNIHKYLA (SEQ ID NO: 123), NAKTLAD (SEQ ID NO: 124), and QHFWSTPLT (SEQ ID NO: 125).

In another embodiment, the anti-TcfA antibody or fragment thereof comprise an amino acid sequence having at least 90%, 95%, 97%, 99%, or 100% homology or identity with any of the sequences provided above (e.g., any of SEQ ID NOs: 115 and 117-125).

Compositions comprising an anti-TcfA antibody or fragment thereof and a carrier such as a pharmaceutically acceptable carrier are also encompassed by the instant invention. In a particular embodiment, the composition comprises at least one anti-TcfA antibody or antibody fragment and at least one carrier (e.g., a pharmaceutically acceptable carrier).

Nucleic acid molecules encoding an anti-TcfA antibody or fragment thereof are encompassed by the instant invention. Examples of nucleic acid molecules encoding anti-TcfA antibodies are provided in FIG. 11. In a particular embodiment, the nucleic acid molecule encoding the anti-TcfA antibody or fragment thereof comprise a nucleotide sequence having at least 90%, 95%, 97%, 99%, or 100% homology or identity with any of the sequences provided above (e.g., any of SEQ ID NOs: 18, 20, 30, 32, 42, 44, 54, 56, 66, 68, 78, 80, 90, 92, 102, 104, 114, and 116) or a nucleotide sequence encoding any of the amino sequences provided above. In a particular embodiment, the nucleic acid molecules of the instant invention are contained within a vector, particularly an expression vector. The instant invention also encompasses cells comprising and, optionally, expressing a nucleic acid molecule of the instant invention (e.g., hybridomas that secrete monoclonal anti-TcfA antibodies).

The antibody may be a synthetic or modified antibody (e.g., a recombinantly generated antibody; a chimeric antibody; a bispecific antibody; a humanized antibody; a camelid antibody; and the like). In a particular embodiment of the instant invention, the antibody is a monoclonal antibody.

The antibodies of the instant invention may be an antibody fragment. In a particular embodiment, the antibody fragment is an antigen binding fragment of the antibody. Antibody fragments include, without limitation, immunoglobulin fragments including, without limitation: single domain (Dab; e.g., single variable light or heavy chain domain), Fab, Fab', F(ab')$_2$, and F(v); and fusions (e.g., via a linker) of these immunoglobulin fragments including, without limitation: scFv, scFv$_2$, scFv-Fc, minibody, diabody, triabody, and tetrabody. The antibody may also be a protein (e.g., a fusion protein) comprising at least one antibody or antibody fragment.

The antibodies of the instant invention may be further modified. For example, the antibodies may be humanized. In a particular embodiment, the antibodies (or a portion thereof) are inserted into the backbone of an antibody or antibody fragment construct (e.g., an antibody framework), particularly a human construct/framework. For example, the variable light domain and/or variable heavy domain of the antibodies of the instant invention or the CDRs contained therein may be inserted into another antibody construct or framework, particularly human. Methods for recombinantly producing antibodies are well-known in the art. Indeed, commercial vectors for certain antibody and antibody fragment constructs are available.

The antibodies of the instant invention may also be conjugated/linked to other components. For example, the antibodies may be operably linked (e.g., covalently linked, optionally, through a linker) to at least one detectable agent, or imaging agent, contrast agent. Detectable agents include, without limitation, colloidal gold or gold nanoparticles, fluorescent probe, colored latex particles, colored cellulose nanobeads, horseradish peroxidase, and europium (Eu) nanoparticles. The antibodies of the instant invention may also comprise at least one purification tag (e.g., a His-tag). In a particular embodiment, the antibodies of the instant invention are conjugated to biotin or streptavidin (or analog thereof).

The antibody molecules of the invention may be prepared using a variety of methods known in the art. Polyclonal and monoclonal antibodies may be prepared as described in Current Protocols in Molecular Biology, Ausubel et al. eds. Antibodies may be prepared by chemical cross-linking, hybrid hybridoma techniques and by expression of recombinant antibody fragments expressed in host cells, such as bacteria or yeast cells. In one embodiment of the invention, the antibody molecules are produced by expression of recombinant antibody or antibody fragments in host cells. The nucleic acid molecules encoding the antibody may be inserted into expression vectors and introduced into host cells. The resulting antibody molecules are then isolated and purified from the expression system. The antibodies optionally comprise a purification tag by which the antibody can be purified.

The purity of the antibody molecules of the invention may be assessed using standard methods known to those of skill in the art, including, but not limited to, ELISA, immunohistochemistry, ion-exchange chromatography, affinity chromatography, immobilized metal affinity chromatography (IMAC), size exclusion chromatography, polyacrylamide gel electrophoresis (PAGE), western blotting, surface plasmon resonance and mass spectroscopy.

In accordance with another aspect of the instant invention, immunoassays for detecting *B. pertussis* are provided. In a particular embodiment, the immunoassay provides a rapid, point of care assay to detect *B. pertussis* during early disease. The immunoassays use at least one of the anti-TcfA antibodies of the instant invention. In a particular embodiment, the immunoassay can be performed at the point-of-care without the need for expensive equipment or the need for specialized equipment or off-site equipment to analyze the data. In a particular embodiment, the immunoassay is carried out using a sample capture device, such as a lateral flow device, more particularly a lateral flow test strip, that allows detection of the TcfA biomarker. In a particular embodiment, the immunoassay is performed on a lateral flow test strip.

The immunoassay of the instant invention has multiple advantages over existing diagnostics. For example, the immunoassay can be performed at the point of care. Other non-limiting advantages include low cost (e.g., no specialized equipment required), ease of use (e.g., no specialized user expertise required), and rapid results (e.g., less than about 40 minutes, less than about 30 minutes, less than about 20 minutes, or less than about 15 minutes). The immunoassay of the instant invention is also convenient for single samples and there is no need or advantage to batch samples.

Lateral flow immunoassays (LFI or LFIA) are simple tests for rapid detection of the presence or absence of a target analyte in a sample. Generally, lateral flow test strips comprise a matrix or material through which a mobile phase (e.g., a liquid sample) can flow through by capillary action to a test site where a detectable signal is generated to indicate the presence or absence of the target analyte. A lateral flow immunoassay may be used in a vertical or a horizontal orientation or in an orientation between vertical and horizontal.

A test strip is an article of manufacture that includes one or more zones, such as, for example, one or more of the following in any appropriate configurations: sample application area or sample pad, absorbent pad or wicking pad, test site, and conjugation pad. The different zones of the test strip may be made of the same material or different material. In a particular embodiment, the test site comprises nitrocellulose, nylon, polyester or polyester composite, matrix membranes (e.g., FUSION 5 (GE Healthcare Life Sciences, Pittsburgh, Pa.)), glass fiber membranes (e.g., Standard 14 or 17), or PVDF. In a particular embodiment, the test and control lines are on nitrocellulose. In a particular embodiment, the conjugate antibody is on a matrix membrane such as FUSION 5. In a particular embodiment, the sample application area or sample pad is a glass fiber membrane. The different zones may be joined by abutting and/or overlapping. The test strip may further comprise a backing to provide rigidity to the test strip (e.g., a supporting non-interactive material such as polyester).

Generally, the lateral flow immunoassay test strip of the present invention comprises a flow path from an upstream sample application area or sample pad to a test site or capture zone. The test site comprises an area (e.g., a line or stripe) of immobilized anti-TcfA antibodies (e.g., one or more anti-TcfA antibodies (either same or different epitopes)) and, optionally, a control area (e.g., a line or stripe) of immobilized control antibodies (e.g., anti-IgG antibodies, anti-species antibodies (e.g., anti-chicken IgG antibodies (e.g., from donkey or goat)). If the conjugated antibodies are biotin-labeled, then the control area (e.g., a line or stripe) may comprise streptavidin (or analogs thereof) instead of or in conjunction with the control antibodies. Alternatively, if the conjugated antibodies are labeled with streptavidin (or analogs thereof), then the control area (e.g., a line or stripe) may comprise biotin instead of or in conjunction with the control antibodies. When present, the control line is preferably further downstream than the test line. Downstream of the test site is generally an absorbent pad or wicking pad to promote capillary action and movement of the fluid from the sample application area or sample pad. Downstream of the sample application area or sample pad and upstream to the test site is a conjugation pad. The conjugation pad comprises anti-TcfA antibodies (e.g., one or more anti-TcfA antibodies (either same or different epitopes)) conjugated to a detectable agent (e.g., colloidal gold or gold nanoparticles, fluorescent probe, colored latex particles, colored cellulose nanobeads, horseradish peroxidase, and europium (Eu) nanoparticles). In a particular embodiment, the detectable agent generates a direct signal that can be observed by a human (e.g., color from gold colloidal). While other detectable agents require additional steps to produce a signal (e.g., an enzyme to produce detectable product upon reaction with suitable substrate (e.g., horseradish peroxidase); a secondary antibody, etc.), these detectable agents are less preferred.

The assay run length of the lateral flow immunoassay test strip will generally be less than 100 mm in length (e.g., including sample pad, conjugate pad, nitrocellulose, and wicking pad). In a particular embodiment, the assay run length is less than about 80 mm, less than about 70 mm, or less than about 60 mm in length. The test site need only be long enough (e.g., at least about 10 mm) to be able to visualize and differentiate the test line and the control line, when present.

Generally, the anti-TcfA antibody of the conjugation pad binds a different epitope than the anti-TcfA antibody of the test site. In a particular embodiment, the anti-TcfA antibody of the conjugation pad (e.g., the antibody conjugated to a detectable agent such as gold) binds amino acids 140-160 of TcfA. In a particular embodiment, the anti-TcfA antibody of the conjugation pad is 7E11, 10B1, or 3E6 (particularly 10B1) or an anti-TcfA antibody which is a fragment or homolog of 7E11, 10B1, or 3E6 as described hereinabove (e.g., an antibody which binds the same epitope or an antibody comprising all 6 CDRs of 7E11, 10B1, or 3E6). In a particular embodiment, the anti-TcfA antibody of the test site binds amino acids 288-304, amino acids 305-323, and/or amino acids 322-330 of TcfA. In a particular embodiment, the anti-TcfA antibody of the test site is 13E11, 14D12, 23F8, 19F9, 14D9, or 25E3 (particularly 13E11 and/or 14D12) or an anti-TcfA antibody which is a fragment or homolog of 13E11, 14D12, 23F8, 19F9, 14D9, or 25E3 as described hereinabove (e.g., an antibody which binds the same epitope or an antibody comprising all 6 CDRs of 13E11, 14D12, 23F8, 19F9, 14D9, or 25E3). In a particular embodiment, the anti-TcfA antibody of the conjugation pad is 101 or an anti-TcfA antibody which is a fragment or homolog of 10B1 as described hereinabove (e.g., an antibody which binds the same epitope as 101 or an antibody comprising all 6 CDRs of 10B1) and the test site comprises 1) 13E11 or an anti-TcfA antibody which is a fragment or homolog of 13E11 as described hereinabove (e.g., an antibody which binds the same epitope as 13E11 or an antibody comprising all 6 CDRs of 13E11), and 2) 14D12 or an anti-TcfA antibody which is a fragment or homolog of 14D12 as described hereinabove (e.g., an antibody which binds the same epitope as 14D12 or an antibody comprising all 6 CDRs of 14D12).

In general, a fluid sample (e.g., by dipping or spotting) is applied to the sample application area or sample pad. In a particular embodiment, the sample is a biological sample obtained from a subject. Biological samples obtained from the subject to be used in the immunoassay of the instant invention include, without limitation: nasopharyngeal swabs, aspirates, and washes. The cells in the biological sample may be lysed prior to analysis. The obtained biological sample may be diluted, purified, concentrated, filtered, dissolved, suspended or otherwise manipulated prior to assay to optimize the immunoassay results. In a particular embodiment, the biological sample is diluted in a carrier or buffer (e.g., a dilution and/or extraction buffer). In a particular embodiment, biological sample is diluted in phosphate buffered saline (PBS). In a particular embodiment, biological sample is diluted in PBS comprising a surfactant (e.g., 0.05% to 2.0%, particularly, 0.1%, 0.25%, 0.5%, 0.75%, or 1.0%), such as an anionic surfactant. Examples of surfactants include, without limitation, alkyl sulfates, alkyl ether sulfates, alkyl ether phosphates, ammonium lauryl sulfate, sodium dodecyl sulfate (SDS), sodium lauryl ether sulfate, and sodium myreth sulfate.

The biological sample for testing can be from any subject. The immunoassay will be particularly useful for the rapid diagnosis of infants (e.g., in pediatrician offices, urgent care clinics, small hospital emergency departments, or medical clinics) with early pertussis. Infants have higher bacterial loads than children or adults (Eby, et al., Infect. Immun. (2013) 81(5):1390-8; Nakamura et al. (2011) Clin. Microbiol. Infect. (2011) 17(3):365-70; Tenenbaum et al., Eur. J. Clin. Microbiol. Infect. Dis. (2012) 31(11):3173-82). This higher load can facilitate detection of B. pertussis antigens. Nonetheless, the immunoassay of the instant invention can also be used on older patients (e.g., children and adults).

Methods for detecting B. pertussis are provided using an immunoassay are also encompassed by the instant invention. In a particular embodiment, the method comprises obtaining a sample (e.g., a biological sample (e.g., from a subject)), diluting the sample in a carrier or buffer, and applying the diluted sample to the immunoassay (e.g., LFI). In a particular embodiment, the method further comprises diagnosing a subject as having a B. pertussis infection based on the presence of a positive result from the immunoassay.

The immunoassays of the instant invention may further comprise assays, particularly other point of care assays. In a particular embodiment, the pertussis diagnostic technology of the instant invention is combined or multiplexed with other respiratory diseases or disorders. In a particular embodiment, the immunoassays of the instant invention further comprise an assay for respiratory syncytial virus (RSV). Many RSV-positive infants are also pertussis-positive (generally 8-16%) and most infants with pertussis are co-infected with RSV (approximately 67-74%) (Nuolivirta, et al., Pediatr. Infect. Dis. J. (2010) 29(11):1013-5; Cosnes-Lambe, et al., Eur. J. Pediatr. (2008) 167(9):1017-9). There is no difference in cough symptoms at hospital admission between infants infected only with RSV vs. infants coinfected with RSV and pertussis (Nuolivirta, et al., Pediatr. Infect. Dis. J. (2010) 29(11):1013-5; Crowcroft, et al., Arch. Dis. Child. (2003) 88(9):802-6). But importantly, detecting co-infection is clinically relevant as infants with RSV and B. pertussis co-infections need antibiotics whereas infants infected solely with RSV do not antibiotics (Bronchiolitis AaoPSoDaMo, Pediatrics (2006) 118(4):1774-93). Thus, the instant invention also encompasses immunoassays, particularly LFIs, comprising the anti-TcfA antibodies of the instant invention in a first test line and RSV detecting agents in a second test line (e.g., antibodies against RSV viral fusion protein (see, e.g., QuickVue® RSV Test (Quidel, San Diego Calif.)) and/or RSV nucleoprotein (see, e.g., ImmunoCard STAT!® RSV (Meidian Biosciences, Cincinnati, Ohio)). These LFIs allow for rapid diagnosis of B. pertussis and/or RSV infections that could otherwise remain undiagnosed and untreated, particularly in infants.

Generally, the immunoassays of the instant invention will be used as a diagnostic for pertussis. Significantly, the immunoassays of the instant invention can also be used to monitor the therapy of a subject with pertussis. For example, after diagnosis with pertussis and administration of an appropriate therapy (e.g., antibiotics), the immunoassays of the instant invention can be used to monitor the amount of B. pertussis and the clearance of the bacteria.

While the present invention has been described with regard to pertussis diagnosis and detecting B. pertussis, the gene for TcfA is also found in B. parapertussis, B. holmesii, and B. bronchiseptica. Notably, B. parapertussis and B. holmesii infect humans and B. bronchiseptica is the causative agent for kennel cough in animals. Thus, in certain embodiments, the anti-TcfA antibodies can also be used to detect the presence of B. parapertussis, B. holmesii, and B. bronchiseptica. Indeed, as seen in Example 2, B. holmesii was detected with one of the five LFIs tested.

In a particular embodiment, the immunoassay of the instant invention is specific for diagnosis and detecting B. pertussis. For example, the immunoassay may be specific for diagnosis and detecting B. pertussis while not significantly detecting B. parapertussis, B. holmesii, and/or B. bronchiseptica.

In accordance with another aspect of the instant invention, compositions and methods for the inhibition, treatment, and/or prevention of pertussis and/or a B. pertussis infection are provided. The methods comprise administering an anti-TcfA antibody or fragment thereof of the instant invention to a subject in need thereof. The anti-TcfA antibodies may be administered in a composition further comprising a pharmaceutically acceptable carrier. The composition may further comprise at least one other therapeutic agent against B. pertussis (e.g., antibiotics). Alternatively, the other therapeutic agent may be contained within a separate composition(s) with at least one pharmaceutically acceptable carrier. The composition(s) comprising at least one anti-TcfA antibody and/or the composition(s) comprising at least one other therapeutic agent may be contained within a kit.

TcfA has been shown to be required for efficient colonization of the trachea in a mouse model of pertussis (Finn, et al., Mol. Microbiol. (1995) 16(4):625-634). Furthermore, the heterologous expression of TcfA in E. coli enables the engineered E. coli to bind human lung epithelial cells, thereby suggesting a role for TcfA for cellular binding and infection (Gasperini, et al., Mol. Cell Proteomics (2018) 17(2):205-215). Notably, passive immunity has been demonstrated with humanized mouse anti-pertussis toxin mAbs when administered to infected baboons. The anti-pertussis toxin mAbs were capable of blunting the post-infection white blood cell increase and increasing the speed by which B. pertussis bacteria was cleared (Nguyen, et al., Sci. Transl. Med. (2015) 7(316):316ra195). Based on the requirement for TcfA for efficient colonization, blocking TcfA with an antibody of the instant invention will provide therapeutic effects by inhibiting the ability of B. pertussis to bind and infect cells.

The compositions of the present invention can be administered by any suitable route, for example, by injection (e.g., for local or systemic administration), intravenous, oral, pulmonary, nasal or other modes of administration. In a particular embodiment, the compositions are administered orally or by inhalation. The compositions comprising the antibodies of the invention may be conveniently formulated for administration with an acceptable medium such as water, buffered saline, ethanol, polyol (for example, glycerol, propylene glycol, liquid polyethylene glycol and the like), dimethyl sulfoxide (DMSO), oils, detergents, suspending agents or suitable mixtures thereof. Selection of a suitable pharmaceutical preparation depends upon the method of administration chosen. The concentration of the antibodies in the chosen medium may be varied and the medium may be chosen based on the desired route of administration of the pharmaceutical preparation. Except insofar as any conventional media or agent is incompatible with the agents to be administered, its use in the pharmaceutical preparation is contemplated. The pharmaceutical composition of the present invention can be prepared, for example, in liquid form, or can be in dried powder form (e.g., lyophilized).

Pharmaceutical compositions containing agents of the present invention as the active ingredient in intimate admixture with a pharmaceutical carrier can be prepared according to conventional pharmaceutical compounding techniques. The carrier may take a wide variety of forms depending on the form of preparation desired for administration. In preparing the antibody in oral dosage form, any of the usual pharmaceutical media may be employed, such as, for example, water, glycols, oils, alcohols, flavoring agents, preservatives, coloring agents and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets).

A pharmaceutical preparation of the invention may be formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art. Dosage units may be proportionately increased or decreased based on the weight of the patient. Appropriate concentrations for alleviation of a particular pathological condition may be determined by dosage concentration curve calculations, as known in the art.

The dose and dosage regimen of the antibodies according to the invention that is suitable for administration to a particular patient may be determined by a physician considering the patient's age, sex, weight, general medical condition, and the specific condition and severity thereof for which the agent is being administered. The physician may also consider the route of administration of the antibodies, the pharmaceutical carrier with which the antibodies may be combined, and the antibodies' biological activity. The appropriate dosage unit for the administration of the agents of the invention may be determined by evaluating the toxicity of the agents in animal models. Appropriate dosage unit may also be determined by assessing the efficacy of the agents in combination with other standard drugs.

The compositions comprising the agents of the instant invention may be administered at appropriate intervals, for example, at least once a day or more until the pathological symptoms are reduced or alleviated, after which the dosage may be reduced to a maintenance level. The appropriate interval in a particular case would normally depend on the condition of the patient.

Definitions

The following definitions are provided to facilitate an understanding of the present invention:

The singular forms "a," "an," and "the" include plural referents unless the context clearly dictates otherwise.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, excipient, auxiliary agent or vehicle with which an active agent of the present invention is administered. Pharmaceutically acceptable carriers can be sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions are preferably employed as carriers. Suitable pharmaceutical carriers are described, for example, in "Remington's Pharmaceutical Sciences" by E. W. Martin.

An "antibody" or "antibody molecule" is any immunoglobulin, including antibodies and fragments thereof, that binds to a specific antigen. As used herein, antibody or antibody molecule contemplates intact immunoglobulin molecules, immunologically active portions of an immunoglobulin molecule (e.g., antigen-binding fragment), and fusions of immunologically active portions of an immunoglobulin molecule.

As used herein, the term "immunologically specific" refers to proteins/polypeptides, particularly antibodies, that bind to one or more epitopes of a protein or compound of interest, but which do not substantially recognize and bind other molecules in a sample containing a mixed population of antigenic biological molecules.

As used herein, "diagnose" refers to detecting and identifying a disease or disorder in a subject. The term may also encompass assessing or evaluating the disease or disorder status (progression, regression, stabilization, response to treatment, etc.) in a patient known to have the disease or disorder.

As used herein, the term "prognosis" refers to providing information regarding the impact of the presence of a disease or disorder (e.g., as determined by the diagnostic methods of the present invention) on a subject's future health (e.g., expected morbidity or mortality). In other words, the term "prognosis" refers to providing a prediction of the probable course and outcome of a disease/disorder and/or the likelihood of recovery from the disease/disorder.

As used herein, the term "subject" refers to an animal, particularly a mammal, particularly a human.

A "therapeutically effective amount" of a compound or a pharmaceutical composition refers to an amount effective to prevent, inhibit, treat, or lessen the symptoms of a particular disorder or disease. The treatment of a disease or disorder herein may refer to curing, relieving, and/or preventing the disease or disorder, the symptom(s) of it, or the predisposition towards it.

As used herein, the term "therapeutic agent" refers to a chemical compound or biological molecule including, without limitation, nucleic acids, peptides, proteins, and antibodies that can be used to treat a condition, disease, or disorder or reduce the symptoms of the condition, disease, or disorder.

The term "isolated" refers to the separation of a compound from other components present during its production or from its natural environment. "Isolated" is not meant to exclude artificial or synthetic mixtures with other compounds or materials, or the presence of impurities that do not substantially interfere with the fundamental activity, and that may be present, for example, due to incomplete purification, or the addition of stabilizers.

As used herein, a "biological sample" refers to a sample of biological material obtained from a subject, particularly a human subject, including a tissue, a tissue sample, cell(s), and a biological fluid (e.g., blood (e.g., whole blood), serum, plasma, urine, sweat, tears, saliva, mucosal secretions, sputum, CSF).

The following examples are provided to illustrate various embodiments of the present invention. The examples are not intended to limit the invention in any way.

Example 1

A bioinformatics-based strategy was used to identify tracheal colonization factor A (TcfA) as a novel biomarker for *B. pertussis* infection. Epitope-specific polyclonal antibodies (pAbs) that recognize the cell-associated and secreted isoforms of TcfA were developed. Specifically, polyclonal antibodies were generated against amino acids 140-160, 288-304, or 305-323 of TcfA.

The specificity of the anti-TcfA antibodies was tested. Specifically, the anti-TcfA pAbs were incorporated into immunoassays, particularly in ELISA and LFI formats. Cultures of bacterial species potentially found in the nasopharynx (*Bordetella pertussis, Moraxella catarrhalis, Streptococcus pneumoniae, Streptococcus pyogenes, Staphylococcus aureus, Haemophilus influenza,* and *Escherichia coli*) were washed from culture plates with phosphate buffered saline (PBS), normalized to an $OD_{600}$ of 1.0, and lysed in 1% sodium dodecyl sulfate (SDS) in PBS for 1 hour at 65° C. The lysates were then tested by antigen-capture ELISA with anti-TcfA pAbs. As seen in FIG. 1, an antigen-capture ELISA with the anti-TcfA pAbs does not detect (i.e., cross-react) with any of the other tested bacteria. In addition to those shown in FIG. 1, the anti-TcfA pAb-based antigen-capture ELISA did not cross-react with *Enterobacter aerogenes, Enterococcus faecalis, Staphylococcus epidermidis, Streptococcus mutans, Streptococcus mitis,* and *Corynebacterium pseudodiptherium*. Similarly, a strong ability to detect *B. pertussis* lysates while showing no detectable cross-reactivity with the above bacteria was observed with the LFI immunoassay. Notably, when the pAbs are used individually in Western blot with lysates of these bacteria, some of them do react with a very limited number of protein bands in only some of the other bacterial species. However, antigen-capture ELISA and LFI require both the capture and detector antibodies to bind the same target. Therefore, it is unlikely that the same cross-reactive protein would be picked up by both the capture and detector pAb since the cross-reactivity in Western blot was so limited. Consequently, neither the antigen-capture ELISA nor the LFI resulted in the detection of any of the other listed bacterial species.

Despite demonstrating specificity for *B. pertussis*, the anti-TcfA pAb-based immunoassay was still able to recognize multiple strains of *B. pertussis*. Specifically, material from two *B. pertussis* strains—Tohama and 165—were tested. Both the Tohama and 165 strains were detected by all anti-TcfA pAb combinations tested by LFI. This result is likely due to the conserved epitopes of the anti-TcfA antibodies. Indeed, the peptide sequences of all 3 of the targeted TcfA epitopes are conserved in >99% (n=436) of clinical isolates from the U.S. and 8 other countries (van Amersfoorth, et al., J. Clin. Microbiol. (2005) 43(6):2837-43; Packard, et al., J. Med. Microbiol. (2004) 53(Pt 5):355-65; van Loo, et al., J. Clin. Microbiol. (2002) 40(6):1994-2001).

TcfA has a cell-associated and a secreted isoform (Finn, et al., Mol. Microbiol. (1995) 16(4):625-34), and the anti-TcfA pAbs described herein are reactive with both isoforms. As seen in FIG. 2, both isoforms were detectable in a Western blot assay as two bands of the appropriate molecular weight are clearly present in cellular lysates. Notably, only the secreted form is observed in 0.2 m-filtered *B. pertussis* conditioned liquid medium (Stainer-Scholte medium). As with the Western blot analysis, both isoforms were detectable using a LFI assay. The secreted isoform was detected on 0.2 m-filtered *B. pertussis* conditioned liquid medium (Stainer-Scholte medium) and the cell-associated isoform was detected on intact, formaldehyde-inactivated cells. Thus, sample preparation for analysis by LFI does not require cell lysis. However, it was determined that detergent lysis of *B. pertussis* cells increased the sensitivity of the anti-TcfA pAb-based LFI. Lysis in 0.1% SDS in PBS, pH 7.4 at room temperature for as little as 5 minutes provided an enhanced signal compared to unlysed samples, but more signal was seen after 60 minutes of lysis or when the lysis was performed at 65° C. rather than room temperature.

The limit of detection of with one of the anti-TcfA pAbs was tested. Specifically, an LFI was performed with *B. pertussis* lysates prepared by detergent lysis for 60 minutes at 65° C. with 0.1% SDS in PBS. The lowest serial dilution scored as positive by 3 of 3 blinded reviewers contained material from $1.7\times10^5$ colony forming units (CFU) (FIG. 3A). A quantitative limit of detection analysis was also performed. The ESE-Quant lateral flow reader (Qiagen, Germantown, Md.) and LF Studio software were used to quantify the test line intensity of multiple dilutions tested in replicates over three days. Background-adjusted data were fit to a linear curve on a semi-log plot with an $R^2$ value of 0.85 (FIG. 3B). The calculated limit of detection was $1.6\times10^5$ CFU, which fits well with the limit of detection determined by reviewers visually. The limit of detection by antigen-capture ELISA was determined to be $3.3\times10^4$ CFU. Notably, both the LFI and ELISA limits of detection are well below the bacterial burden found in infant nasopharynx washes ($10^7$ to $10^{10}$ CFU/ml) or swabs ($10^6$ CFU) (Eby, et al., Infect. Immun. (2013) 81(5):1390-8; Nakamura, et a., Clin. Microbiol. Infect. (2011) 17(3):365-70; Tenenbaum, et al., Eur. J. Clin. Microbiol. Infect. Dis. (2012) 31(11):3173-82).

Example 2

Although pAbs can be used in commercial LFIs, monoclonal antibodies (mAbs) are preferred for commercialization because of their superior affinity (i.e., better LFI sensitivity), lot-to-lot reproducibility, and their more efficient, reliable, and economic large-scale production. Thus, a library of anti-TcfA mAbs was developed and the mAbs were incorporated into an advanced mAb-based LFI diagnostic to achieve enhanced analytical sensitivity and better commercialization potential.

Generating a library of mAbs against TcfA required an unusually large number of immunization and hybridoma screening strategies. Ultimately, a large library of mAb-secreting hybridomas was generated and the mAbs showed robust reactivity in ELISA with immobilized antigen (recombinant TcfA, endogenous TcfA including formaldehyde-inactivated *B. pertussis* cells and/or TcfA peptides). Thirty-six mAbs were advanced for large-scale hybridoma culture and mAb purification via Protein A affinity chromatography.

The reactivity of the mAbs was measured by indirect ELISA with plates coated with various antigen (FIG. 4). The immobilized antigens were formaldehyde-inactivated *B. pertussis* cells, recombinant TcfA containing a histidine tag, TcfA peptides (amino acids 140-160, 288-304, or 305-323) conjugated to bovine serum albumin (BSA), or control BSA. The reactivity of the mAbs was also tested against clarified, 0.2 μm-filtered supernatant from *B. pertussis* Tohama I cultures grown in Stainer-Scholte medium or Stainer-Scholte uninocculated medium. As seen in FIG. 4, most of the mAb demonstrated a strong but selective reactivity for TcfA.

In order to determine the epitopes recognized by the mAb, purified mAbs were evaluated by indirect ELISA with streptavidin plates loaded with biotinylated peptides. The peptides were 15mers that were offset by 3 amino acids. The minimal overlapping peptide sequence for wells with an $OD_{450}$ greater than 0.75 (and in a series of two or more such adjacent wells) was defined as the minimal linear peptide epitope (Table 1). Notably, mAbs 22B7 and 14D9 reacted with a long series of peptides such that the first peptide in the series did not overlap with the last peptide. For these mAbs, the peptide sequence defined by the entire series of reactive wells is provided. In addition, purified mAbs were evaluated by indirect ELISA with plates coated with the TcfA protein fragments. With the exception of amino acids 40-374, all protein fragments were conjugated to bovine serum albumin.

TABLE 1

Epitopes within TcfA recognized by the mAbs.

| mAb | Minimal linear peptide epitope | Protein fragment reactivity |
|---|---|---|
| 10B1 | aa139-150 PGIGKVGGSAPG | aa140-160 |
| 7E11 | aa139-150 PGIGKVGGSAPG | aa140-160 |
| 7A10 | aa148-159 APGPDTSTGSGP | aa140-160 |
| 9A3 | aa148-159 APGPDTSTGSGP | aa140-160 |
| 7E9 | aa148-159 APGPDTSTGSGP | aa140-160 |
| 3E6 | aa151-156 PDTSTG | aa140-160 |
| 7 A3 | aa151-156 PDTSTG | aa140-160 |
| 15F3 | aa151-159 PDTSTGSGP | aa140-160 |
| 21D6 | aa151-159 PDTSTGSGP | aa140-160 |
| 15A9 | aa151-159 PDTSTGSGP | aa140-160 |
| 14F4 | aa151-159 PDTSTGSGP | aa140-160 |
| 17H2 | aa151-159 PDTSTGSGP | aa140-160 |
| 14G6 | aa151-159 PDTSTGSGP | aa140-160 |
| 15B9 | aa151-159 PDTSTGSGP | aa140-160 |
| 11B5 | aa151-159 PDTSTGSGP | aa140-160 |
| 4A6 | aa151-159 PDTSTGSGP | aa140-160 |
| 13E11 | aa229-240; PADGGQDGPPPP; aa289-300; LPERGDDAGPKP; aa304-312 EGGDEGPQP | aa288-304, aa305-323 |
| 19D10 | aa229-240; PADGGQDGPPPP; aa289-300; LPERGDDAGPKP; aa304-312 EGGDEGPQP | aa288-304, aa305-323 |
| 22B7 | aa286-321 NAQLPERGDDAGPKPPEGEG GDEGPQPPQGGGEQDA | aa288-304, aa305-323 |
| 14D9 | aa289-324 LPERGDDAGPKPPEGEGG DEGPQPPQGGGEQDAPEV | aa288-304, aa305-323 |
| 19F9 | aa289-294 LPERGD | aa288-304 |
| 23F8 | aa292-300 RGDDAGPKP | aa288-304 |
| 14D12 | aa292-300 RGDDAGPKP | aa288-304 |
| 20F4 | aa307-315 DEGPQPPQG | aa305-323 |
| 14A8 | aa310-315 PQPPQG | aa305-323 |
| 14G11 | aa313-321 PQGGGEQDA | aa305-323 |
| 25E3 | aa322-330 PEVPPVAPA | aa40-374 |
| 18B2 | aa337-345 VYDPGTHTL | aa40-374 |

The sequence identifiers for the provided minimal linear peptide epitope are: aa139-150 (SEQ ID NO: 2); aa148-159 (SEQ ID NO: 3); aa151-156 (SEQ ID NO: 4); aa151-159 (SEQ ID NO: 5); aa229-240 (SEQ ID NO: 6); aa289-300 (SEQ ID NO: 7); aa304-312 (SEQ ID NO: 8); aa286-321 (SEQ ID NO: 9); aa289-324 (SEQ ID NO: 10); aa289-294 (SEQ ID NO: 11); aa292-300 (SEQ ID NO: 12); aa307-315 (SEQ ID NO: 13); aa3 10-315 (SEQ ID NO: 14); aa313-321 (SEQ ID NO: 15); aa322-330 (SEQ ID NO: 16); and aa337-345 (SEQ ID NO: 17).

Example 3

Figure 5:
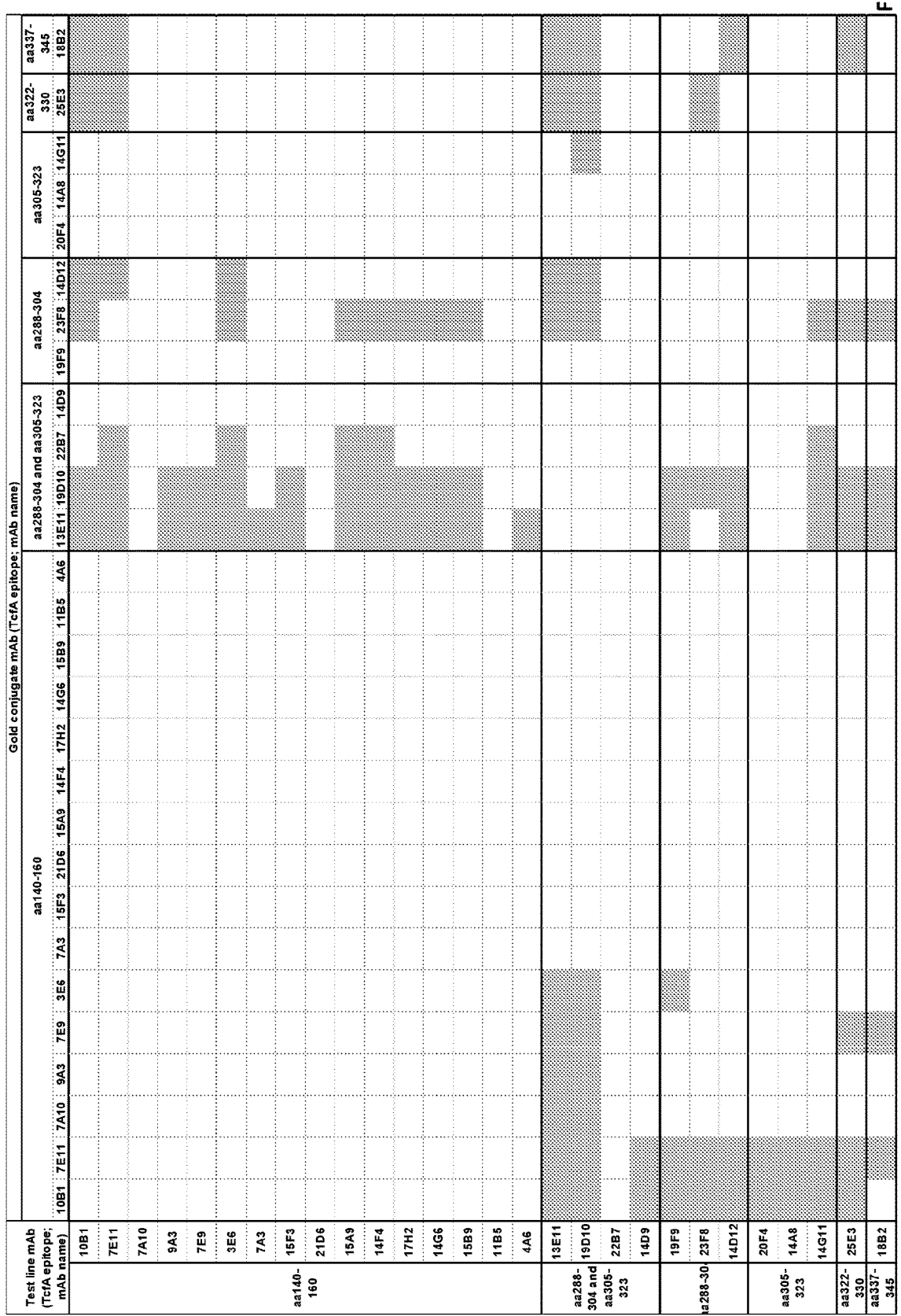
FIG. 5 shows the reactivity of anti-TcfA mAb based LFIs with formaldehyde-inactivated B. pertussis cells in phosphate buffered saline (PBS) at an $OD_{600}$ of 2.0. All LFIs that produced more signal with B. pertussis cells in PBS than with PBS alone (as determined by visual inspection) were quantified with a Qiagen ESEQuant Lateral Flow Reader running the Lateral Flow Studio Software suite. All LFI tests were performed a second time on a second day. Grey boxes indicate successful LFIs, as defined by meeting both of the following metrics: 1) had quantified signal with B. pertussis cells that was greater than twice the signal seen with PBS alone (signal comparisons were done with the averages of the two replicates tested), and 2) had quantified signal with PBS of less than 100 units (average of two replicates). White boxes indicate LFIs whose signal did not meet both of the former metrics.
Figure 7:
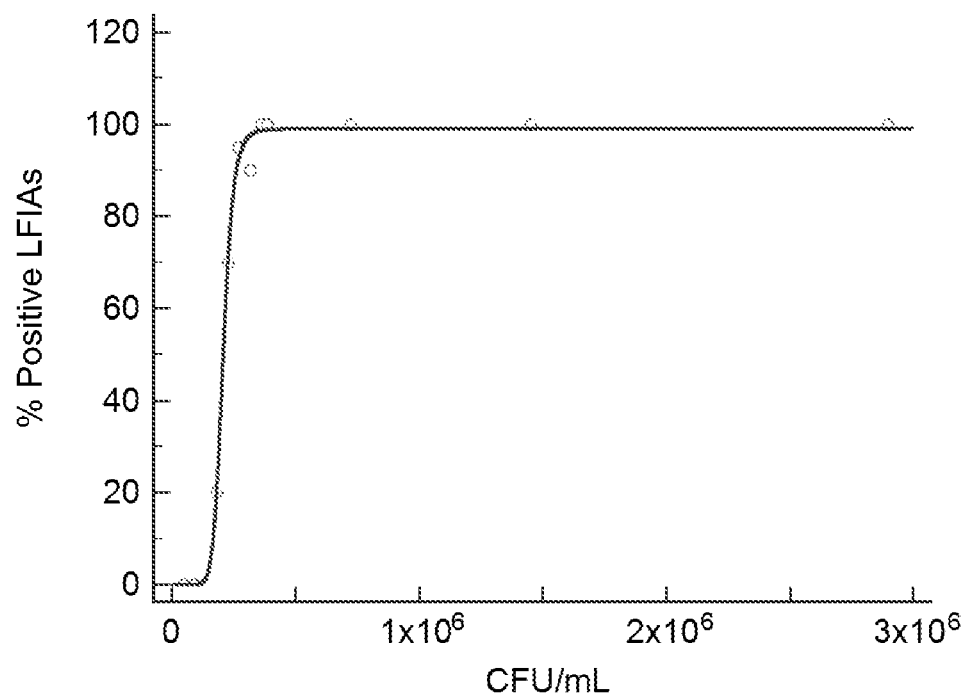
FIG. 7 provides a graph of the analytical sensitivity of the mAB-based LFI for viable B. pertussis (Tohama I) in extraction buffer using monoclonal Abs. The detection limit of the LFI was determined to be $3 \times 10^5$ CFU/mL ($1.8 \times 10^4$ CFU per LFI test). Viable B. pertussis (Tohama I strain) cells were suspended in phosphate buffered saline (PBS) at 11 different $OD_{600}$ concentrations. Cell suspensions were then mixed with extraction buffer for 5 minutes and then analyzed by LFI. Each concentration was evaluated on 20 replicate LFIs. All LFIs were from one lot. Each LFI was interpreted visually by three readers who were blind as to the concentration being tested. LFIs interpreted as positive by 3 of 3 blind readers were categorized as "Positive". Nonlinear regression analysis using a 4-parameter logistic model was used to determine the line of best fit, and the equation for the line was used to calculate the concentration at which 95% of the LFIs would be reported as positive (C95; detection limit).
Figure 8:
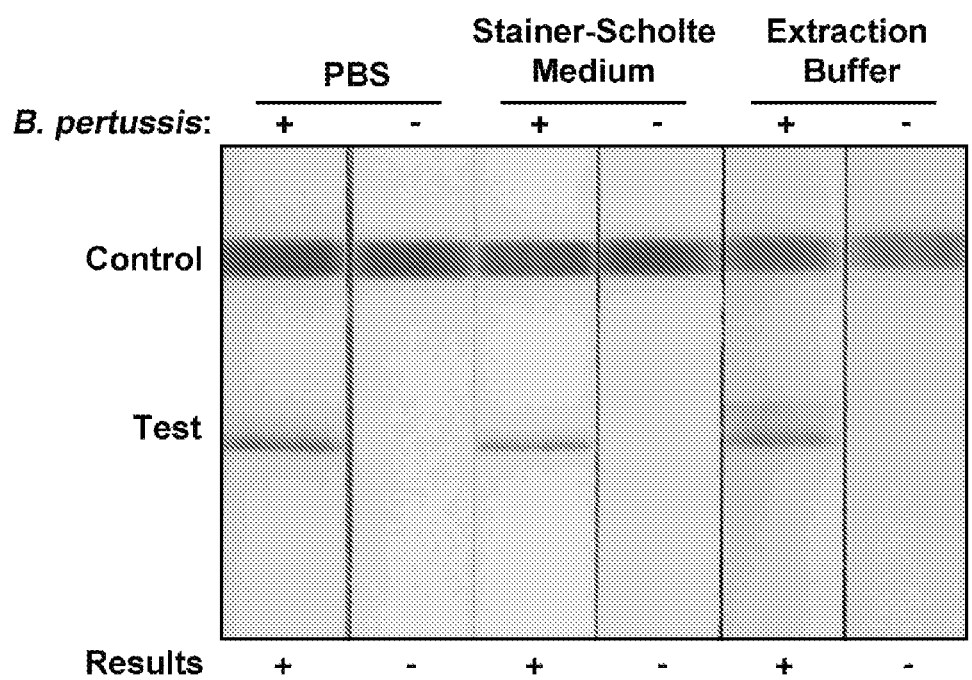
FIG. 8 provides an image of a LFI using monoclonal anti-TcfA antibodies. Lanes 1 and 2: formaldehyde-inactivated B. pertussis cells (Tohama I strain) cells in PBS ($OD_{600}$ of 0.1) vs. PBS alone. Lanes 3 and 4: clarified, 0.2 μm-filtered supernatant from B. pertussis (strain 165) cultures in Stainer-Scholte medium vs. uninoculated Stainer-Scholte medium (both diluted 1:128 in PBS). Lanes 5 and 6: formaldehyde-inactivated B. pertussis cells (Tohama I strain) in PBS ($OD_{600}$ of 0.1) lysed for 5 minutes in extraction buffer vs. extraction buffer alone.
Figure 9:
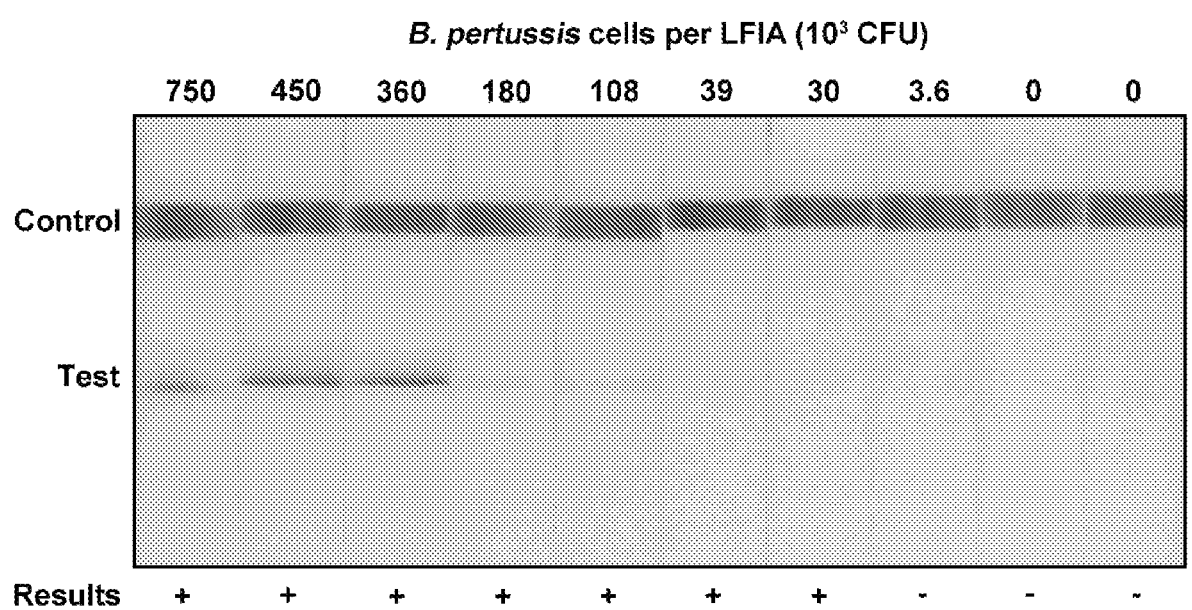
FIG. 9 provides an image of a LFI using monoclonal anti-TcfA antibodies. Nasopharyngeal washes from baboons challenged with B. pertussis and containing the listed CFU per LFI testing volume were incubated with extraction buffer for 5 minutes at room temperature. LFI development time was 15 minutes.
Figure 10:
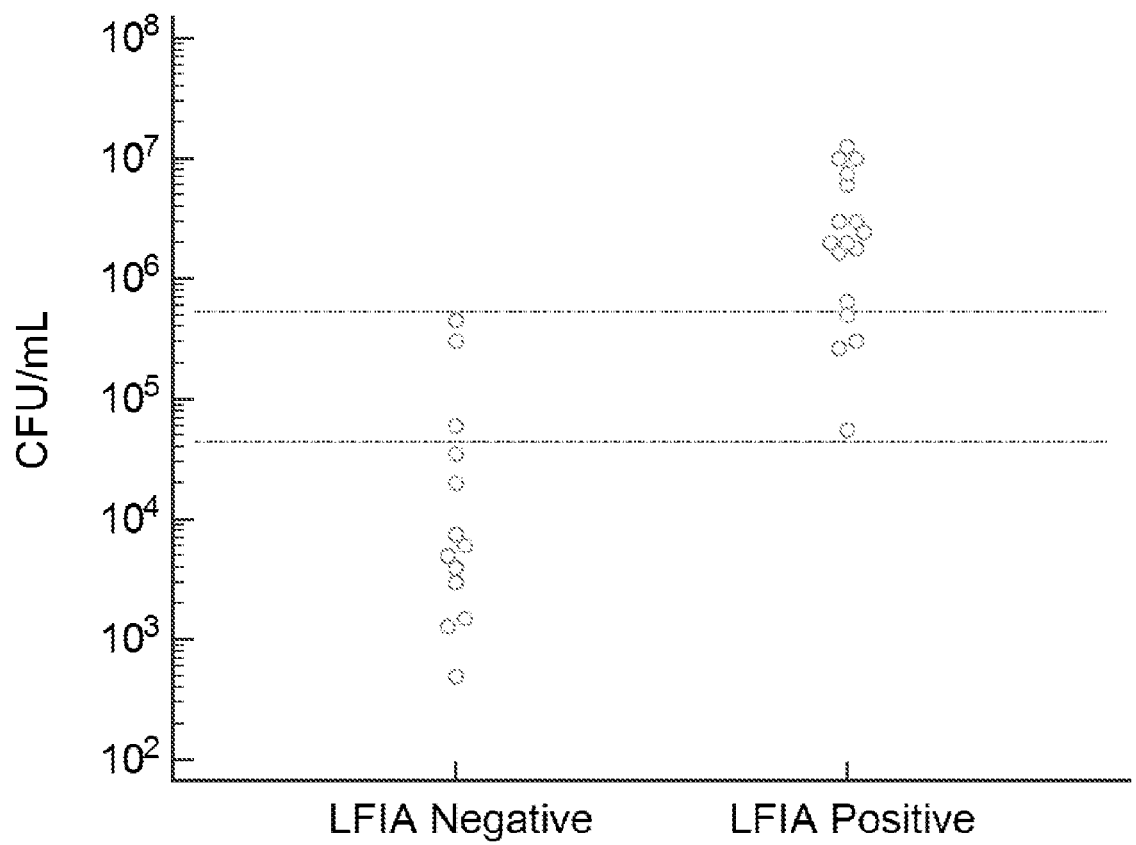
FIG. 10 provides a graph showing the sensitivity of the mAb-based LFI with challenged baboon nasopharyngeal washes containing the indicated CFU. All infected baboon nasopharyngeal washes with $\geq 5 \times 10^5$ CFU/mL were positive by LFI (top horizontal reference line), and all infected baboon nasopharyngeal washes with $\leq 3.5 \times 10^4$ CFU/mL were negative by LFI (bottom horizontal reference line). A total of 30 nasopharyngeal washes from baboons challenged with B. pertussis were analyzed by LFI in duplicate. The LFI produced no false-positives with 11 baboon nasopharyngeal washes (tested in on duplicate LFIs) that had 0 CFU/mL (i.e. the LFI had 100% specificity).

Anti-TcfA mAbs were evaluated for performance as a detector mAb (i.e., gold conjugate) and as a capture mAb (i.e., test line) in an LFI while holding all other LFI components constant (e.g., nitrocellulose, conjugate pad, sample pad, wicking pad, blocking buffers, chase buffer). A significant number of LFI mAb pair permutations were identified that effectively detected formaldehyde-inactivated B. pertussis cells (FIG. 5). Indeed, most of the ELISA-capable anti-TcfA mAbs evaluated by LFI formed at least 1 functional LFI pair (FIGS. 4 and 5). Notably, many anti-TcfA mAbs had comparable performance in ELISA against immobilized antigen (FIG. 4). However, in the LFI, some of the anti-TcfA mAbs worked far better than the others as test line mAbs, other anti-TcfA mAbs worked better as gold conjugate mAbs, and still other anti-TcfA mAbs worked well in both positions (e.g., anti-TcfA mAbs 14D9, 14D12, and 25E3, respectively) (FIG. 5). In a further analysis, the anti-TcfA mAbs were binned by their reactivity (or lack thereof) with the three TcfA peptides that were used to generate the polyclonal antibodies. It was found that anti-TcfA mAbs that target the same epitope failed to form functional mAb pairs for LFI (FIG. 5). However, when the anti-TcfA mAbs targeted different epitopes, functional mAb pairs for LFI were identified.

Several anti-TcfA mAb combinations for LFIs (FIG. 5) were advanced to BSL-2 testing to determine their cross-reactivity with a panel of ten other nasopharyngeal pathogens and to establish a preliminary limit of detection with viable *B. pertussis* cells. These LFIs were selected based on their strong signal with i) formaldehyde-inactivated *B. pertussis* cells (Tohama I strain), ii) detergent lysates of *B. pertussis* cells (Tohama I strain), and iii) conditioned media (not formaldehyde-treated) from a second strain of *B. pertussis* (strain 165) grown as liquid cultures in Stainer-Scholte medium. Three of the LFIs (14D12 test line+7E11 gold conjugate; 25E3 test line+10B1 gold conjugate; 14D9 test line+7E11 gold conjugate) were found to have no detectable cross-reactivity with viable cell suspensions in PBS of *Haemophilus parainfluenzae, Haemophilus influenzae, Moraxella catarrhalis, Streptococcus pneumoniae, Streptococcus pyogenes, Corynebacterium diphtheriae, Staphylococcus epidermidis, Bordetella parapertussis, Bordetella holmesii*, or *Bordetella bronchiseptica*. One LFI had reactivity with *H. influenza* and *B. holmesii*. A different LFI had reactivity with *S. epidermidis*. One LFI (13E11 and 14D12 test line+10B1 gold conjugate) was subjected to additional cross-reactivity testing, in which cross-reactivity was evaluated with 40 other species of bacteria and fungi potentially found in nasopharyngeal specimens (Table 2). This expanded cross-reactivity testing of Table 2 was performed by testing LFIs in triplicate with samples containing $3.33\times10^7$ CFU/mL of the indicated pathogen in extraction buffer.

TABLE 2

Pertussis LFI cross-reactivity testing (14D12 and 13E11 test line + 10B1 gold conjugate).

| Microorganism ($3.33\times10^7$ CFU/mL) | LFI Result |
|---|---|
| *Acinetobacter baumanni* | Negative |
| *Acinetobacter calcoaceticus* | Negative |
| *Acinetocacter Iwoffii* | Negative |
| *Aspergillus fumigatus* | Negative |
| *Bacillus cereus* | Negative |
| *Bacillus subtilis* | Negative |
| *Bacteroides fragilis* | Negative |
| *Bordetella bronchiseptica* (ATCC 19395) | Negative |
| *Bordetella bronchiseptica* (ATCC BAA-588) | Negative |
| *Bordetella holmesii* (F061) | Negative |
| *Bordetella parapertussis* (A747) | Negative |
| *Bordetella parapertussis* (C510) | Negative |
| *Candida albicans* | Negative |
| *Candida glabrata* | Negative |
| *Citrobacter amalonaticus* | Negative |
| *Citrobacter freundii* | Negative |
| *Citrobacter koseri* | Negative |
| *Cornebacterium diphtheria* | Negative |
| *Enterobacter aerogenes* | Negative |
| *Enterobacter cloacae* | Negative |
| *Enterococcus faecalis* (Z346) | Negative |
| *Enterococcus faecium* (Z265) | Negative |
| *Escherichia coli* (O157) | Negative |
| *Haemophilus influenzae* | Negative |
| *Haemophilus parainfluenzae* (ATCC33392) | Negative |
| *Legionella pneumophila* (Philadelphia) | Negative |

TABLE 2-continued Pertussis LFI cross-reactivity testing (14D12 and 13E11 test line + 10B1 gold conjugate).

| Microorganism (3.33 × 10⁷ CFU/mL) | LFI Result |
| --- | --- |
| *Moraxella catarrhalis* | Negative |
| *Morganella morganii* (Z098) | Negative |
| *Mycoplasma pneumonia* (M129) | Negative |
| *Proteus mirabilis* (Z050) | Negative |
| *Proteus vulgaris* (Z129) | Negative |
| *Pseudomonas aeruginosa* | Negative |
| *Staphylococcus epidermidis* | Negative |
| *Stenotrophomonas maltophilia* (Z074) | Negative |
| *Streptococcus agalactiae* (Z019) | Negative |
| *Streptococcus dysgalactiae* | Positive* |
| *Streptococcus mitis* | Negative |
| *Streptococcus mutans* (Z072) | Negative |
| *Streptococcus pneumoniae* | Negative |
| *Streptococcus pyogenes* | Negative |
| *Streptococcus salivarius* (Z127) | Negative |
| *Streptococcus sanguinis* (Z089) | Negative |

Testing for *S. dysgalactiae* was repeated by centrifuging cells to remove traces of growth medium and resuspending cells in extraction buffer at the same CFU/mL concentration; 3 of 3 LFI replicates were negative. *S. dysgalactiae* testing was also repeated by diluting cells. At a concentration of 8.3 × 10⁶ CFU/mL, 3 of 3 LFI replicates were negative.

The preliminary limit of detection for five of the LFIs with viable *B. pertussis* cells was $2 \times 10^5$ to $5 \times 10^5$ CFU. Two of the three LFIs with no detectable cross-reactivity had preliminary limits of detection of $2 \times 10^5$ CFU. These two LFIs are: 1) mAb 14D12 as the test line and mAb 7E11 as the gold conjugate; and 2) mAb 25E3 as the test line and mAb 10B1 as the gold conjugate. The sixth LFI (14D12 and 13E11 test line+10B1 gold conjugate) was subjected to detailed limit of detection testing and was determined to have an analytical sensitivity limit of $3\times10^5$ CFU/mL ($1.8\times10^4$ CFU per LFI test) (FIG. 7). For comparison, the best pAb based LFI (see Example 1) had a final limit of detection of $1.6\times10^5$ CFU. However, achieving that limit of detection with the pAb based LFI required i) heating the *B. pertussis* cells in 0.1% SDS at 65° C. for 1 hour, and ii) incorporating an 80 mm assay run length, which necessitated a longer assay run time (optimal run time was 30 minutes, though strong positives were visible sooner). The instant mAb based LFIs have better limit of detection despite their use of viable *B. pertussis* cells with only a simple 5 minute room temperature incubation in extraction buffer and short development times of 15-20 minutes due to a 60 mm assay run length, of which 25 mm is nitrocellulose. *B. pertussis* is strictly a human pathogen that lacks an animal or environmental reservoir (Mattoo, et al., Clin. Microbiol. Rev., (2005) 18(2):326-82). However, a baboon model has been developed that is the only animal model that accurately reproduces the full disease course seen in human infection (Warfel, et al., Expert Rev. Vaccines (2014) 13(10):1241-52; Merkel, et al., J. Infect. Dis. (2014) 209 Suppl 1:520-3; Warfel, et al., Infect. Immun. (2012) 80(4):1530-6; Warfel, et al., Proc. Natl. Acad. Sci. (2014) 111(2):787-92). This well-established, clinically relevant model of naturally transmitted infection in baboons can be used to provide nasopharynx samples to study the ability of the LFIs to diagnose various disease stages.

Example 4

A library of *B. pertussis* mAbs has been generated. The mAbs bind viable and formaldehyde-inactivated *B. pertussis* cells. In addition to use as diagnostic reagents, these mAbs are valuable as therapeutics, prophylactics, and/or research tools (e.g., for fluorescence microscopy on fresh or fixed tissue sections, etc.).

A mAb-based LFI was optimized for sensitive, specific detection of *B. pertussis*. The LFI comprised 14D12 and 13E11 in the test line and 10B1 as the conjugated antibody. The LFI detected *B. pertussis* antigen in ≤20 minutes with a simple protocol, enabling diagnostic use at the point-of-care.

Human infant nasopharyngeal washes contain $7\times10^7$ to $8\times10^{10}$ CFU/mL (Eby, et al., Infect. Immun. (2013) 81(5): 1390-8; Tenenbaum, et al., Eur. J. Clin. Microbiol. Infect. Dis. (2012) 31(11):3173-82). These CFU/ml values are approximately 200-fold to 260,000-fold greater than the LFI's analytical sensitivity limit (i.e., C95). Indeed, as seen in FIG. 7, the LFI has an estimated analytical sensitivity (C95) of $3\times10^5$ CFU/mL ($1.8\times10^4$ CFU per LFI test) for viable *B. pertussis* (Tohama I) in extraction buffer. Nonlinear regression analysis using a 4-parameter logistic model (MedCalc Software) was used to determine the line of best fit. The equation for the line was used to calculate the concentration at which 95% of LFIs would be positive. Each concentration was evaluated by 20 LFI replicates; all LFIs were from one lot.

The LFI produced strong signal with multiple *B. pertussis* strains and sample types. As an example, FIG. 8 shows formaldehyde-inactivated *B. pertussis* cells (Tohama I strain) cells in PBS ($OD_{600}$ of 0.1) vs. PBS alone; clarified, 0.2 μm-filtered supernatant from Stainer-Scholte *B. pertussis* (strain 165) cultures vs. uninoculated Stainer-Scholte medium (both diluted 1:128 in PBS); and formaldehyde-inactivated *B. pertussis* cells (Tohama I strain) in PBS ($OD_{600}$ of 0.1) lysed for 5 minutes in extraction buffer vs. extraction buffer alone. The LFI has shown reactivity with at least 9 different strains of *B. pertussis* including: Tohama I, 165, D420, H973, H792, H735, E431, A639, and CNCTC Hp 12/63 [623].

Nasopharyngeal washes from baboons infected by natural, airborne transmission have greater than or equal to $5\times10^5$ CFU/mL from approximately Day 15 to Day 33 post-exposure (Warfel, et al., Proc. Natl. Acad. Sci. (2014) 111(2):787-92). The LFI detected antigen from infected baboon nasopharyngeal washes containing as little as $5.5\times10^4$ CFU/mL ($3.3\times10^3$ CFU per LFI test) (FIG. 10). The LFI consistently reported positive results with infected baboon nasopharyngeal washes greater than or equal to $5\times10^5$ CFU/mL ($3\times10^4$ CFU per LFI test) (FIG. 10). No LFI false-positives were observed.

Specifically, as seen in FIGS. 9 and 10, the LFI reacted with nasopharyngeal washes from baboons infected with *B. pertussis* (strain D420). Individual nasopharyngeal washes from baboons challenged with *B. pertussis* and containing the listed CFU per LFI testing volume were incubated with extraction buffer for 5 minutes at room temperature. LFI development time was 15 minutes.

As seen in FIG. 10, all infected baboon nasopharyngeal washes with greater than or equal to $5\times10^5$ CFU/mL were positive by LFI (top horizontal reference line), and all infected baboon nasopharyngeal washes with less than or equal to $3.5\times10^4$ CFU/mL were negative by LFI (bottom horizontal reference line). A total of 30 nasopharyngeal washes from baboons challenged with *B. pertussis* were analyzed by LFI. The LFI produced no false-positives with 11 baboon NP washes that had 0 CFU/mL (i.e. the LFI had 100% specificity).

In addition, the LFI has been tested with human patient samples (nasopharyngeal swabs). The LFI was negative with 2 of 2 patient samples that were diagnosed by RT-PCR as negative for pertussis. The LFI was positive with 1 patient sample that was diagnosed by RT-PCR as being positive for pertussis and with a high bacterial burden. The LFI was negative with 1 patient sample that was diagnosed by RT-PCR as positive for pertussis but with a significantly lower bacterial burden. The 1 positive LFI with the 1 patient who was positive by RT-PCR shows proof of concept for detection of *B. pertussis* in human nasopharyngeal swab specimens.

Together, the baboon and human results indicate that the LFI can detect infection from two different types of nasopharyngeal specimens: nasopharyngeal washes and nasopharyngeal swabs.

The mAb-based LFI for detection of *B. pertussis* antigen allows for early, point-of-care diagnosis of pertussis using minimally-invasive nasopharyngeal specimens. The availability of a rapid and simple test for detection of pertussis will increase early diagnosis, as well as facilitate immediate triage, treatment, and outbreak containment.

Several publications and patent documents are cited in the foregoing specification in order to more fully describe the state of the art to which this invention pertains. The disclosure of each of these citations is incorporated by reference herein.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. An isolated antibody or antigen binding fragment thereof immunologically specific for tracheal colonization factor A (TcfA), wherein said antibody or fragment thereof comprises all six complementarity determining regions from 14D12, 23F8, 18B2, 20F4, 14G11, 13E11, 10B1, 7E11, or 3E6.

2. The antibody or fragment thereof of claim 1, wherein said antibody or fragment thereof comprises
   a) a heavy chain comprising NYAMS (SEQ ID NO: 24), SISSGGSYIYYSDSVKG (SEQ ID NO: 25), and GAHGNFDY (SEQ ID NO: 26) and a light chain comprising RTSETVDYDGDSYMN (SEQ ID NO: 27), GASNVES (SEQ ID NO: 28), and QQNRKLPYT (SEQ ID NO: 29);
   b) a heavy chain comprising DYGMH (SEQ ID NO: 36), YISSGSRTIYYADTVKG (SEQ ID NO: 37), and LGYGYDWYFDV (SEQ ID NO: 38) and a light chain comprising KSSQSLLDSDGRTYLN (SEQ ID NO: 39), LVSKLDS (SEQ ID NO: 40), and WQGTHFPQT (SEQ ID NO: 41);
   c) a heavy chain comprising NYWIG (SEQ ID NO: 48), DIYPGGVYTNYNENFKG (SEQ ID NO: 49), and GGKYGNFFAMDY (SEQ ID NO: 50) and a light chain comprising RSSKSLLYKDGKTYLN (SEQ ID NO: 51), LMSTRAS (SEQ ID NO: 52), and QQLVEYPFT (SEQ ID NO: 53);
   d) a heavy chain comprising NYGMN (SEQ ID NO: 60), WINTYTGEPTYADDFKG (SEQ ID NO: 61), and AATGYFDY (SEQ ID NO: 62) and a light chain comprising KSSQSLLYSSNQKNYLA (SEQ ID NO: 63), WASTRES (SEQ ID NO: 64), and QQYYNEYT (SEQ ID NO: 65);
   e) a heavy chain comprising DYYMS (SEQ ID NO: 72), FIRNKANGYTTEYSASVKG (SEQ ID NO: 73), and YRRDYYGSLNYYTMDY (SEQ ID NO: 74) and a light chain comprising RASENIYSYLA (SEQ ID NO: 75), NAKTLAE (SEQ ID NO: 76), and QNHYGIPLT (SEQ ID NO: 77);
   f) a heavy chain comprising DYGMH (SEQ ID NO: 84), YISSGSSTIYYADTVKG (SEQ ID NO: 85), and PRSGRYFDY (SEQ ID NO: 86) and a light chain comprising KSSQSLLDSNGNTYLH (SEQ ID NO: 87), LVSKLDS (SEQ ID NO: 88), and LQGTHFPYT (SEQ ID NO: 89);
   g) a heavy chain comprising DTYIH (SEQ ID NO: 96), RIDPANGNTIYASKFQG (SEQ ID NO: 97), and MDY (SEQ ID NO: 98) and a light chain comprising KSSQSLLHSNGKTYLN (SEQ ID NO: 99), LVSKLDS (SEQ ID NO: 100), and LQATHFPHT (SEQ ID NO: 101);
   h) a heavy chain comprising DTYIH (SEQ ID NO: 108), RIDPANGNIIYASKFQG (SEQ ID NO: 109), and MDY (SEQ ID NO: 110) and a light chain comprising KSSQSLLHSNGKTYLN (SEQ ID NO: 111), LVSKLDS (SEQ ID NO: 112), and LQATHFPHT (SEQ ID NO: 113); or
   i) a heavy chain comprising DYYMS (SEQ ID NO: 120), FIRNKAKGYTTDYSASVKG (SEQ ID NO: 121), and NYDYSMDY (SEQ ID NO: 122) and a light chain comprising RASDNIHKYLA (SEQ ID NO: 123), NAKTLAD (SEQ ID NO: 124), and QHFWSTPLT (SEQ ID NO: 125).

3. The antibody or fragment thereof of claim 1, wherein said antibody or fragment thereof comprises
   a) a heavy chain comprising: EVMLVESGGALVKPGGSLKLSCAASGITFSNYAMSWIRQTPEKRLEWV ASISSGGSYIYYSDSVKGRFTISRDNARNTLNLQMSSLRSEDTAMYYCVRGAHGNFDYWGQGTTLTVSS (SEQ ID NO: 22) and a light chain comprising: DIVLTQSPASLAVSLGQRATISCRTSETVDYDGDSYMNWYQQKSGQP PKLLISGASNVESGVPARFSGSGSGTDFSLNIHPVEEDDITMYFCQQNRKLPYTFGSGTKLE MK (SEQ ID NO: 23);
   b) a heavy chain comprising: EVQLVESGGGLVKPGGSRKLSCAASGFTFSDYGMHWVRQAPEKGLEWV AYISSGSRTIYYADTVKGRFTISRDNAKNTLFLQMTSLRSEDTAMYYCARLGYGYDWYFDVW GTGTTVTVSS (SEQ ID NO: 34) and a light chain comprising: DVVMTQTPLTLSVTIGQPASISCKSSQSLLDSDGRTYLNWLLQRPGQS PKRLIYLVSKLDSGVPDRFTGSGSGTDFTLKISRVEAEDLGIYYCWQGTHFPQTFGGGTKLE IK (SEQ ID NO: 35);
   c) a heavy chain comprising: QVQLQQSGAELVRPGTSVKMSCKAAGYTFTNYWIGWVKQRPGHGLEWIGDI YPGGVYTNYNENFKGKATLTADTSSSTAHMQLSSLTSEDSAIYYCVRGGKYGNFFAMDYWGQ GTSVTVSS (SEQ ID NO: 46) and a light chain comprising: DIVITQDELSNPVTSGESVSISCRSSKSLLYKDGKTYLNWFLQRPGQ SPQLLIYLMSTRASGVSDRFSGSGSGTDFTLEISRVKAEDVGVYYCQQLVEYPFTFGSGTKL EIK (SEQ ID NO: 47);
   d) a heavy chain comprising: QIQLVQSGPELKKPGETVKISCKASGYTFTNYGMNWVKQAPGKGLKWM GWINTYTGEPTYADDFKGRFAFSLETSATTAYLQINNLKNEDTATYFCARAATGYFDYWGQG TTLTVSS (SEQ ID NO: 58) and a light chain comprising: DIVMSQSPSSLAVSAGEKVTMSCKSSQSLLYSSNQKNYLAWYQQKPG QSPKLLIYWASTRESGVPDRFTGSGSGTDFTLTISSVKAEDLAVYYCQQYYNEYTF( EIK (SEQ ID NO: 59);
   e) a heavy chain comprising: EVKLVESGGGLVQPGGSLSLSCAASGFTFTDYYMSWVRQPPGKALEWL GFIRNKANGYTTEYSASVKGRFTISRDNSQSILYLQMNALRAEDSATYYCARYRRDYYGSLN YYTMD YWGQGTSVTVSS (SEQ ID NO: 70) and a light chain comprising: DIQMTQSPASLSASVGETVTITCRASENIYSYLAWYQQKQGKSPQLL VYNAKTLAE-

GVPSRFSGSGSGTQFSLKINSLQPEDFGSYYCQNHYGIPLTFGAGTKLELK (SEQ ID NO: 71);

f) a heavy chain comprising: EVQLVESGGGLVKPGGSRKLSCAASGFTFSDYGMHWVRQAPEKGLEWV AYISSGSSTIYYADTVKGRFTISRDNAKNTLFLQMTSLRSEDTAMYYCARPRSGRYFDYWGQGTTLTVSS (SEQ ID NO: 82) and a light chain comprising: DVMMTQTPLTLSVTIGQPASISCKSSQSLLDSNGNTYLHWLLQRPGQS PKILIYLVSKLDSGVPDRFSGSGSGTDFTLKISRVEAEDLGVYYCLQGTHFPYTFGGGTKLE IK (SEQ ID NO: 83);

g) a heavy chain comprising: EVQLQQSGAELVKPGASVKLSCTASGFNIKDTYIHWVKQRPEQGLEWI GRIDPANGNTIYASKFQGKAPITAVISSNTAYMQFSSLTSGDTAVYYCTAMDYWGQGTSVTV SS (SEQ ID NO: 94) and a light chain comprising: DVVMTQTPLTLSVTIGQPASISCKSSQSLLHSNGKTYLNWLLQRPGQS PKLLIYLVSKLDSGVPDRFSGSGSGTDFTLKISRVEAEDLGVYYCLQATHFPHTFGSGTKLE IK (SEQ ID NO: 95);

h) a heavy chain comprising: EVQLQQSGAELVKPGASVKLSCTASGFNIKDTYIHWVKQRPEQGLEWI GRIDPANGNIIYASKFQGEATITADTSSNTAYMQLSSLTSGDTAVYYCSAMDYWGQGTSVTV SS (SEQ ID NO: 106) and a light chain comprising: DVVMTQTPLTLSLTIGQPASISCKSSQSLLHSNGKTYLNWLLQRPGQS PKLLIYLVSKLDSGVPDRFSGSGSGTDFTLKISRVEAEDLGVYYCLQATHFPHTFGSGTKLE IK (SEQ ID NO: 107); or i) a heavy chain comprising: EVKLVESGGGLVQPGGSLRLSCATSGFTFTDYYMSWVRQPPGKALEWM GFIRNKAKGYTTDYSASVKGRFTISRDDSQSILYLQMNTLRPEDSATYYCARNYDYSMDYWGQGTSVTVSS (SEQ ID NO: 118) and a light chain comprising: DIQLTQSPASLSASVGETVTITCRASDNIHKYLAWYQQKQGKSPQRL VYNAKTLADGVPSRFNGSGSGTQYSLKINSLQPEDFGIYYCQHFWSTPLTFGAGTKLELK (SEQ ID NO: 119).

4. The antibody or fragment thereof of claim 1 conjugated to at least one detectable agent.

5. The antibody or fragment thereof of claim 4, wherein said detectable agent is a gold nanoparticle.

6. A composition comprising an antibody or fragment thereof of claim 1 and a carrier.

7. A method of detecting *Bordetella pertussis* in a sample, said method comprising contacting the sample with at least one antibody or fragment thereof of claim 1.

8. The method of claim 7, wherein said sample is a biological sample obtained from a subject.

9. The method of claim 8, wherein said biological sample is a nasopharyngeal swab, aspirate, or wash.

10. A methods for inhibiting, treating, and/or preventing pertussis and/or a *B. pertussis* infection in a subject in need thereof, said method comprising administering an antibody or fragment thereof of claim 1 to the subject.

11. An immunoassay comprising at least one antibody or fragment thereof of claim 1.

12. A method of detecting *Bordetella pertussis* in a sample, said method comprising analyzing the sample with an immunoassay of claim 11.

13. A lateral flow immunoassay test strip, wherein said lateral flow immunoassay test strip comprises a test site comprising one or more anti-TcfA antibodies of claim 4 and a conjugation pad comprising one or more anti-TcfA antibodies of claim 1 conjugated to a detectable agent.

14. The immunoassay of claim 13, wherein the conjugated antibody specifically binds amino acids 139-150 or amino acids 151-156 of TcfA.

15. The immunoassay of claim 14, wherein the conjugated antibody specifically binds amino acids 139-150 of TcfA.

16. The immunoassay of claim 13, wherein the test site antibody specifically binds amino acids 289-324 of TcfA.

17. The immunoassay of claim 13, wherein the test site antibody specifically binds amino acids 289-294 of TcfA.

18. The immunoassay of claim 13, wherein the test site antibody specifically binds amino acids 292-300 of TcfA.

19. The immunoassay of claim 13, wherein the test site antibody specifically binds amino acids 322-330 of TcfA.

20. The immunoassay of claim 13, wherein the conjugated antibody specifically binds amino acids 289-324 of TcfA.

21. The immunoassay of claim 20, wherein the test site antibody specifically binds amino acids 139-150 of TcfA.

22. The immunoassay of claim 13, wherein the conjugated antibody specifically binds the same epitope as 10B1 and said test site comprises antibodies which bind the same epitope as 14D12 and antibodies which bind the same epitope as 13E11.

* * * * *

SEQUENCE LISTING

```
<160> NUMBER OF SEQ ID NOS: 125

<210> SEQ ID NO 1
<211> LENGTH: 647
<212> TYPE: PRT
<213> ORGANISM: Bordetella pertussis

<400> SEQUENCE: 1

Met His Ile Tyr Gly Asn Met Asn Arg Ala Thr Pro Cys Arg Gly Ala
1               5                   10                  15

Val Arg Ala Leu Ala Leu Ala Leu Leu Gly Ala Gly Met Trp Thr Leu
            20                  25                  30

Ser Pro Pro Ser Ala Trp Ala Leu Lys Leu Pro Ser Leu Leu Thr Asp
        35                  40                  45

Asp Glu Leu Lys Leu Val Leu Pro Thr Gly Met Ser Leu Glu Asp Phe
    50                  55                  60

Lys Arg Ser Leu Gln Glu Ser Ala Pro Ser Ala Leu Ala Thr Pro Pro
65                  70                  75                  80

Ser Ser Ser Pro Pro Val Ala Lys Pro Gly Pro Gly Ser Val Ala Glu
                85                  90                  95

Ala Pro Ser Gly Ser Gly His Lys Asp Asn Pro Ser Pro Pro Val Val
            100                 105                 110

Gly Val Gly Pro Gly Met Ala Glu Ser Ser Gly Gly His Asn Pro Gly
        115                 120                 125

Val Gly Gly Gly Thr His Glu Asn Gly Leu Pro Gly Ile Gly Lys Val
    130                 135                 140

Gly Gly Ser Ala Pro Gly Pro Asp Thr Ser Thr Gly Ser Gly Pro Asp
145                 150                 155                 160

Ala Gly Met Ala Ser Gly Ala Gly Ser Thr Ser Pro Gly Ala Ser Gly
                165                 170                 175

Gly Ala Gly Lys Asp Ala Met Pro Pro Ser Glu Gly Glu Arg Pro Asp
            180                 185                 190

Ser Gly Met Ser Asp Ser Gly Arg Gly Gly Glu Ser Ser Ala Gly Gly
        195                 200                 205

Leu Asn Pro Asp Gly Ala Gly Lys Pro Pro Arg Glu Glu Gly Glu Pro
    210                 215                 220

Gly Ser Lys Ser Pro Ala Asp Gly Gly Gln Asp Gly Pro Pro Pro
225                 230                 235                 240

Arg Asp Gly Gly Asp Ala Asp Pro Gln Pro Pro Arg Asp Asp Gly Asn
                245                 250                 255
```

```
Gly Glu Gln Gln Pro Pro Lys Gly Gly Asp Glu Gly Gln Arg Pro
            260             265             270

Pro Pro Ala Ala Gly Asn Gly Gly Asn Gly Gly Asn Gly Asn Ala Gln
        275             280             285

Leu Pro Glu Arg Gly Asp Asp Ala Gly Pro Lys Pro Pro Glu Gly Glu
    290             295             300

Gly Gly Asp Glu Gly Pro Gln Pro Pro Gln Gly Gly Glu Gln Asp
305             310             315             320

Ala Pro Glu Val Pro Pro Val Ala Pro Pro Ala Gly Asn Gly
                325             330             335

Val Tyr Asp Pro Gly Thr His Thr Leu Thr Pro Ala Ser Ala Ala
        340             345             350

Val Ser Leu Ala Ser Ser His Gly Val Trp Gln Ala Glu Met Asn
    355             360             365

Ala Leu Ser Lys Arg Met Gly Glu Leu Arg Leu Thr Pro Val Ala Gly
        370             375             380

Gly Val Trp Gly Arg Ala Phe Gly Arg Arg Gln Asp Val Asp Asn Arg
385             390             395             400

Val Ser Arg Glu Phe Arg Gln Thr Ile Ser Gly Phe Glu Leu Gly Ala
            405             410             415

Asp Thr Ala Leu Pro Val Ala Asp Gly Arg Trp His Val Gly Ala Val
        420             425             430

Ala Gly Tyr Thr Asn Gly Arg Ile Lys Phe Asp Arg Gly Thr Gly
            435             440             445

Asp Asp Asp Ser Val His Val Gly Ala Tyr Ala Thr Tyr Ile Glu Asp
450             455             460

Gly Gly Phe Tyr Met Asp Gly Ile Val Arg Val Ser Arg Ile Arg His
465             470             475             480

Ala Phe Lys Val Asp Asp Ala Lys Gly Arg Arg Val Arg Gly Gln Tyr
            485             490             495

Arg Gly Asn Gly Val Gly Ala Ser Leu Glu Leu Gly Lys Arg Phe Thr
            500             505             510

Trp Pro Gly Ala Trp Tyr Val Glu Pro Gln Leu Glu Val Ala Ala Phe
        515             520             525

His Ala Gln Gly Ala Asp Tyr Thr Ala Ser Asn Gly Leu Arg Ile Lys
    530             535             540

Asp Asp Gly Thr Asn Ser Met Leu Gly Arg Leu Gly Leu His Val Gly
545             550             555             560

Arg Gln Phe Asp Leu Gly Asp Gly Arg Val Val Gln Pro Tyr Met Lys
            565             570             575

Leu Ser Trp Val Gln Glu Phe Asp Gly Lys Gly Thr Val Arg Thr Asn
            580             585             590

Asp Ile Arg His Lys Val Arg Leu Asp Gly Gly Arg Thr Glu Leu Ala
        595             600             605

Val Gly Val Ala Ser Gln Leu Gly Lys His Gly Ser Leu Phe Gly Ser
        610             615             620

Tyr Glu Tyr Ala Lys Gly Ser Arg Gln Thr Met Pro Trp Thr Phe His
625             630             635             640

Val Gly Tyr Arg Tyr Ala Trp
            645

<210> SEQ ID NO 2
<211> LENGTH: 12
<212> TYPE: PRT
```

```
<213> ORGANISM: Artificial Sequence
<220> FEATURE:
<223> OTHER INFORMATION: peptide epitope

<400> SEQUENCE: 2

Pro Gly Ile Gly Lys Val Gly Gly Ser Ala Pro Gly
1               5                   10

<210> SEQ ID NO 3
<211> LENGTH: 12
<212> TYPE: PRT
<213> ORGANISM: Artificial Sequence
<220> FEATURE:
<223> OTHER INFORMATION: peptide epitope

<400> SEQUENCE: 3

Ala Pro Gly Pro Asp Thr Ser Thr Gly Ser Gly Pro
1               5                   10

<210> SEQ ID NO 4
<211> LENGTH: 6
<212> TYPE: PRT
<213> ORGANISM: Artificial Sequence
<220> FEATURE:
<223> OTHER INFORMATION: peptide epitope

<400> SEQUENCE: 4

Pro Asp Thr Ser Thr Gly
1               5

<210> SEQ ID NO 5
<211> LENGTH: 9
<212> TYPE: PRT
<213> ORGANISM: Artificial Sequence
<220> FEATURE:
<223> OTHER INFORMATION: peptide epitope

<400> SEQUENCE: 5

Pro Asp Thr Ser Thr Gly Ser Gly Pro
1               5

<210> SEQ ID NO 6
<211> LENGTH: 12
<212> TYPE: PRT
<213> ORGANISM: Artificial Sequence
<220> FEATURE:
<223> OTHER INFORMATION: peptide epitope

<400> SEQUENCE: 6

Pro Ala Asp Gly Gly Gln Asp Gly Pro Pro Pro Pro
1               5                   10

<210> SEQ ID NO 7
<211> LENGTH: 12
<212> TYPE: PRT
<213> ORGANISM: Artificial Sequence
<220> FEATURE:
<223> OTHER INFORMATION: peptide epitope

<400> SEQUENCE: 7

Leu Pro Glu Arg Gly Asp Asp Ala Gly Pro Lys Pro
1               5                   10

<210> SEQ ID NO 8
<211> LENGTH: 9
<212> TYPE: PRT
<213> ORGANISM: Artificial Sequence
```

```
<220> FEATURE:
<223> OTHER INFORMATION: peptide epitope

<400> SEQUENCE: 8

Glu Gly Gly Asp Glu Gly Pro Gln Pro
1               5

<210> SEQ ID NO 9
<211> LENGTH: 36
<212> TYPE: PRT
<213> ORGANISM: Artificial Sequence
<220> FEATURE:
<223> OTHER INFORMATION: peptide epitope

<400> SEQUENCE: 9

Asn Ala Gln Leu Pro Glu Arg Gly Asp Asp Ala Gly Pro Lys Pro Pro
1               5                   10                  15

Glu Gly Glu Gly Gly Asp Glu Gly Pro Gln Pro Pro Gln Gly Gly Gly
            20                  25                  30

Glu Gln Asp Ala
        35

<210> SEQ ID NO 10
<211> LENGTH: 36
<212> TYPE: PRT
<213> ORGANISM: Artificial Sequence
<220> FEATURE:
<223> OTHER INFORMATION: peptide epitope

<400> SEQUENCE: 10

Leu Pro Glu Arg Gly Asp Asp Ala Gly Pro Lys Pro Pro Glu Gly Glu
1               5                   10                  15

Gly Gly Asp Glu Gly Pro Gln Pro Pro Gln Gly Gly Gly Glu Gln Asp
            20                  25                  30

Ala Pro Glu Val
        35

<210> SEQ ID NO 11
<211> LENGTH: 6
<212> TYPE: PRT
<213> ORGANISM: Artificial Sequence
<220> FEATURE:
<223> OTHER INFORMATION: peptide epitope

<400> SEQUENCE: 11

Leu Pro Glu Arg Gly Asp
1               5

<210> SEQ ID NO 12
<211> LENGTH: 9
<212> TYPE: PRT
<213> ORGANISM: Artificial Sequence
<220> FEATURE:
<223> OTHER INFORMATION: peptide epitope

<400> SEQUENCE: 12

Arg Gly Asp Asp Ala Gly Pro Lys Pro
1               5

<210> SEQ ID NO 13
<211> LENGTH: 9
<212> TYPE: PRT
<213> ORGANISM: Artificial Sequence
<220> FEATURE:
<223> OTHER INFORMATION: peptide epitope
```

<400> SEQUENCE: 13

Asp Glu Gly Pro Gln Pro Pro Gln Gly
1               5

<210> SEQ ID NO 14
<211> LENGTH: 6
<212> TYPE: PRT
<213> ORGANISM: Artificial Sequence
<220> FEATURE:
<223> OTHER INFORMATION: peptide epitope

<400> SEQUENCE: 14

Pro Gln Pro Pro Gln Gly
1               5

<210> SEQ ID NO 15
<211> LENGTH: 9
<212> TYPE: PRT
<213> ORGANISM: Artificial Sequence
<220> FEATURE:
<223> OTHER INFORMATION: peptide epitope

<400> SEQUENCE: 15

Pro Gln Gly Gly Gly Glu Gln Asp Ala
1               5

<210> SEQ ID NO 16
<211> LENGTH: 9
<212> TYPE: PRT
<213> ORGANISM: Artificial Sequence
<220> FEATURE:
<223> OTHER INFORMATION: peptide epitope

<400> SEQUENCE: 16

Pro Glu Val Pro Pro Val Ala Pro Ala
1               5

<210> SEQ ID NO 17
<211> LENGTH: 9
<212> TYPE: PRT
<213> ORGANISM: Artificial Sequence
<220> FEATURE:
<223> OTHER INFORMATION: peptide epitope

<400> SEQUENCE: 17

Val Tyr Asp Pro Gly Thr His Thr Leu
1               5

<210> SEQ ID NO 18
<211> LENGTH: 408
<212> TYPE: DNA
<213> ORGANISM: Artificial Sequence
<220> FEATURE:
<223> OTHER INFORMATION: 14D12 heavy chain

<400> SEQUENCE: 18
atgaacttcg ggctcagctt gattttcctt gtccttattt taaaaggtgt ccagtgtgaa     60
gtgatgctgg tggagtctgg gggagcctta gtgaagcctg gagggtccct gaaactctcc    120
tgtgcagcct ctggaataac tttcagtaac tatgccatgt cttggattcg ccagactcca    180
gagaagagac tggagtgggt cgcaagtatt agtagtggtg gtagttatat ctactattca    240
gacagtgtga aggtcgatt caccatttcc agagacaatg ccaggaacac cctgaacctg    300
caaatgagca gtctgaggtc tgaggacacg gccatgtatt actgtgtaag agggggcgcat    360 ggaaattttg actactgggg ccaaggcacc actctcacag tctcctca        408

<210> SEQ ID NO 19
<211> LENGTH: 136
<212> TYPE: PRT
<213> ORGANISM: Artificial Sequence
<220> FEATURE:
<223> OTHER INFORMATION: 14D12 heavy chain

<400> SEQUENCE: 19

Met Asn Phe Gly Leu Ser Leu Ile Phe Leu Val Leu Ile Leu Lys Gly
1               5                   10                  15

Val Gln Cys Glu Val Met Leu Val Glu Ser Gly Gly Ala Leu Val Lys
            20                  25                  30

Pro Gly Gly Ser Leu Lys Leu Ser Cys Ala Ala Ser Gly Ile Thr Phe
        35                  40                  45

Ser Asn Tyr Ala Met Ser Trp Ile Arg Gln Thr Pro Glu Lys Arg Leu
    50                  55                  60

Glu Trp Val Ala Ser Ile Ser Ser Gly Gly Ser Tyr Ile Tyr Tyr Ser
65                  70                  75                  80

Asp Ser Val Lys Gly Arg Phe Thr Ile Ser Arg Asp Asn Ala Arg Asn
                85                  90                  95

Thr Leu Asn Leu Gln Met Ser Ser Leu Arg Ser Glu Asp Thr Ala Met
            100                 105                 110

Tyr Tyr Cys Val Arg Gly Ala His Gly Asn Phe Asp Tyr Trp Gly Gln
        115                 120                 125

Gly Thr Thr Leu Thr Val Ser Ser
    130                 135

<210> SEQ ID NO 20
<211> LENGTH: 393
<212> TYPE: DNA
<213> ORGANISM: Artificial Sequence
<220> FEATURE:
<223> OTHER INFORMATION: 14D12 light chain

<400> SEQUENCE: 20
atggagtcag acacactcct gctatgggtg ctgctgctct gggttccagg ctccactggt        60
gacattgtgc tgacccaatc tccagcttct ttggctgtgt ctctagggca gagagccacc       120
atctcctgca gaaccagtga aactgttgat tatgatggcg atagttatat gaactggtac       180
caacagaaat caggacagcc acccaaactc ctcatatctg gtgcatccaa cgtagagtct       240
ggggtccctg ccaggttcag tggcagtggg tctgggacag acttcagcct caacatccat       300
cctgtggagg aggatgatat tacaatgtat ttctgtcagc aaaataggaa gcttccgtat       360
acgttcggat cggggaccaa gctggaaatg aaa                                   393

<210> SEQ ID NO 21
<211> LENGTH: 131
<212> TYPE: PRT
<213> ORGANISM: Artificial Sequence
<220> FEATURE:
<223> OTHER INFORMATION: 14D12 light chain

<400> SEQUENCE: 21

Met Glu Ser Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

```
Val Ser Leu Gly Gln Arg Ala Thr Ile Ser Cys Arg Thr Ser Glu Thr
        35                  40                  45

Val Asp Tyr Asp Gly Asp Ser Tyr Met Asn Trp Tyr Gln Gln Lys Ser
 50                  55                  60

Gly Gln Pro Pro Lys Leu Leu Ile Ser Gly Ala Ser Asn Val Glu Ser
 65                  70                  75                  80

Gly Val Pro Ala Arg Phe Ser Gly Ser Gly Ser Gly Thr Asp Phe Ser
                85                  90                  95

Leu Asn Ile His Pro Val Glu Asp Asp Ile Thr Met Tyr Phe Cys
                100                 105                 110

Gln Gln Asn Arg Lys Leu Pro Tyr Thr Phe Gly Ser Gly Thr Lys Leu
            115                 120                 125

Glu Met Lys
        130

<210> SEQ ID NO 22
<211> LENGTH: 117
<212> TYPE: PRT
<213> ORGANISM: Artificial Sequence
<220> FEATURE:
<223> OTHER INFORMATION: 14D12 heavy chain

<400> SEQUENCE: 22

Glu Val Met Leu Val Glu Ser Gly Gly Ala Leu Val Lys Pro Gly Gly
 1               5                   10                  15

Ser Leu Lys Leu Ser Cys Ala Ala Ser Gly Ile Thr Phe Ser Asn Tyr
                20                  25                  30

Ala Met Ser Trp Ile Arg Gln Thr Pro Glu Lys Arg Leu Glu Trp Val
            35                  40                  45

Ala Ser Ile Ser Ser Gly Gly Ser Tyr Ile Tyr Tyr Ser Asp Ser Val
        50                  55                  60

Lys Gly Arg Phe Thr Ile Ser Arg Asp Asn Ala Arg Asn Thr Leu Asn
 65                  70                  75                  80

Leu Gln Met Ser Ser Leu Arg Ser Glu Asp Thr Ala Met Tyr Tyr Cys
                85                  90                  95

Val Arg Gly Ala His Gly Asn Phe Asp Tyr Trp Gly Gln Gly Thr Thr
                100                 105                 110

Leu Thr Val Ser Ser
        115

<210> SEQ ID NO 23
<211> LENGTH: 111
<212> TYPE: PRT
<213> ORGANISM: Artificial Sequence
<220> FEATURE:
<223> OTHER INFORMATION: 14D12 light chain

<400> SEQUENCE: 23

Asp Ile Val Leu Thr Gln Ser Pro Ala Ser Leu Ala Val Ser Leu Gly
 1               5                   10                  15

Gln Arg Ala Thr Ile Ser Cys Arg Thr Ser Glu Thr Val Asp Tyr Asp
                20                  25                  30

Gly Asp Ser Tyr Met Asn Trp Tyr Gln Gln Lys Ser Gly Gln Pro Pro
            35                  40                  45

Lys Leu Leu Ile Ser Gly Ala Ser Asn Val Glu Ser Gly Val Pro Ala
        50                  55                  60

Arg Phe Ser Gly Ser Gly Ser Gly Thr Asp Phe Ser Leu Asn Ile His
```

```
                65                  70                  75                  80
Pro Val Glu Glu Asp Asp Ile Thr Met Tyr Phe Cys Gln Gln Asn Arg
                    85                  90                  95
Lys Leu Pro Tyr Thr Phe Gly Ser Gly Thr Lys Leu Glu Met Lys
            100                 105                 110

<210> SEQ ID NO 24
<211> LENGTH: 5
<212> TYPE: PRT
<213> ORGANISM: Artificial Sequence
<220> FEATURE:
<223> OTHER INFORMATION: 14D12 fragment

<400> SEQUENCE: 24

Asn Tyr Ala Met Ser
1               5

<210> SEQ ID NO 25
<211> LENGTH: 17
<212> TYPE: PRT
<213> ORGANISM: Artificial Sequence
<220> FEATURE:
<223> OTHER INFORMATION: 14D12 fragment

<400> SEQUENCE: 25

Ser Ile Ser Ser Gly Gly Ser Tyr Ile Tyr Tyr Ser Asp Ser Val Lys
1               5                   10                  15
Gly

<210> SEQ ID NO 26
<211> LENGTH: 8
<212> TYPE: PRT
<213> ORGANISM: Artificial Sequence
<220> FEATURE:
<223> OTHER INFORMATION: 14D12 fragment

<400> SEQUENCE: 26

Gly Ala His Gly Asn Phe Asp Tyr
1               5

<210> SEQ ID NO 27
<211> LENGTH: 15
<212> TYPE: PRT
<213> ORGANISM: Artificial Sequence
<220> FEATURE:
<223> OTHER INFORMATION: 14D12 fragment

<400> SEQUENCE: 27

Arg Thr Ser Glu Thr Val Asp Tyr Asp Gly Asp Ser Tyr Met Asn
1               5                   10                  15

<210> SEQ ID NO 28
<211> LENGTH: 7
<212> TYPE: PRT
<213> ORGANISM: Artificial Sequence
<220> FEATURE:
<223> OTHER INFORMATION: 14D12 fragment

<400> SEQUENCE: 28

Gly Ala Ser Asn Val Glu Ser
1               5

<210> SEQ ID NO 29
<211> LENGTH: 9
<212> TYPE: PRT
```

```
<213> ORGANISM: Artificial Sequence
<220> FEATURE:
<223> OTHER INFORMATION: 14D12 fragment

<400> SEQUENCE: 29

Gln Gln Asn Arg Lys Leu Pro Tyr Thr
1               5

<210> SEQ ID NO 30
<211> LENGTH: 417
<212> TYPE: DNA
<213> ORGANISM: Artificial Sequence
<220> FEATURE:
<223> OTHER INFORMATION: 23F8 heavy chain

<400> SEQUENCE: 30
atggactcca ggctcaattt agttttcctt gtcctttttt taaaaggtgt ccagtgtgag      60
gtgcagctgg tggagtctgg gggaggctta gtgaagcctg agggtcccg gaaactctcc     120 tgtgcagcct ctggattcac tttcagtgac tatggaatgc actgggttcg tcaggctcca     180
gagaagggac tggagtgggt tgcatacatt agtagtggca gtagaaccat ctactatgca     240
gacacagtga aggccgatt caccatctcc agagacaatg ccaagaacac cctgttcctg      300
caaatgacca gtctaaggtc tgaggacacg gccatgtatt actgtgcaag gctgggctat     360
ggttacgact ggtacttcga tgtctggggc acagggacca cggtcaccgt ctcctca        417

<210> SEQ ID NO 31
<211> LENGTH: 139
<212> TYPE: PRT
<213> ORGANISM: Artificial Sequence
<220> FEATURE:
<223> OTHER INFORMATION: 23F8 heavy chain

<400> SEQUENCE: 31

Met Asp Ser Arg Leu Asn Leu Val Phe Leu Val Leu Phe Leu Lys Gly
1               5                   10                  15

Val Gln Cys Glu Val Gln Leu Val Glu Ser Gly Gly Gly Leu Val Lys
            20                  25                  30

Pro Gly Gly Ser Arg Lys Leu Ser Cys Ala Ala Ser Gly Phe Thr Phe
        35                  40                  45

Ser Asp Tyr Gly Met His Trp Val Arg Gln Ala Pro Glu Lys Gly Leu
    50                  55                  60

Glu Trp Val Ala Tyr Ile Ser Ser Gly Ser Arg Thr Ile Tyr Tyr Ala
65                  70                  75                  80

Asp Thr Val Lys Gly Arg Phe Thr Ile Ser Arg Asp Asn Ala Lys Asn
                85                  90                  95

Thr Leu Phe Leu Gln Met Thr Ser Leu Arg Ser Glu Asp Thr Ala Met
            100                 105                 110

Tyr Tyr Cys Ala Arg Leu Gly Tyr Gly Tyr Asp Trp Tyr Phe Asp Val
        115                 120                 125

Trp Gly Thr Gly Thr Thr Val Thr Val Ser Ser
    130                 135

<210> SEQ ID NO 32
<211> LENGTH: 393
<212> TYPE: DNA
<213> ORGANISM: Artificial Sequence
<220> FEATURE:
<223> OTHER INFORMATION: 23F8 light chain

<400> SEQUENCE: 32
```

```
atgagtcctg cccagttcct gtttctgtta gtgctctgga tgcgggaaac caacggtgat    60
gttgtgatga cccagactcc actcactttg tcggttacca ttggacaacc agcctccatc   120
tcctgcaagt caagtcagag cctcttagat agtgatggaa ggacatattt gaattggttg   180
ttacagaggc caggccagtc tccaaagcgc ctgatctatc tggtgtctaa actggactct   240
ggagtccctg acaggttcac tggcagtgga tcagggacag atttcacact gaaaatcagc   300
agagtggagg ctgaggattt gggaatttat tattgctggc aaggtacaca ttttcctcag   360
acgttcggtg gaggcaccaa gctggaaatc aaa                                393
```

```
<210> SEQ ID NO 33
<211> LENGTH: 131
<212> TYPE: PRT
<213> ORGANISM: Artificial Sequence
<220> FEATURE:
<223> OTHER INFORMATION: 23F8 light chain

<400> SEQUENCE: 33

Met Ser Pro Ala Gln Phe Leu Phe Leu Leu Val Leu Trp Met Arg Glu
1               5                   10                  15

Thr Asn Gly Asp Val Val Met Thr Gln Thr Pro Leu Thr Leu Ser Val
            20                  25                  30

Thr Ile Gly Gln Pro Ala Ser Ile Ser Cys Lys Ser Ser Gln Ser Leu
        35                  40                  45

Leu Asp Ser Asp Gly Arg Thr Tyr Leu Asn Trp Leu Leu Gln Arg Pro
    50                  55                  60

Gly Gln Ser Pro Lys Arg Leu Ile Tyr Leu Val Ser Lys Leu Asp Ser
65                  70                  75                  80

Gly Val Pro Asp Arg Phe Thr Gly Ser Gly Ser Gly Thr Asp Phe Thr
                85                  90                  95

Leu Lys Ile Ser Arg Val Glu Ala Glu Asp Leu Gly Ile Tyr Tyr Cys
            100                 105                 110

Trp Gln Gly Thr His Phe Pro Gln Thr Phe Gly Gly Thr Lys Leu
        115                 120                 125

Glu Ile Lys
    130
```

```
<210> SEQ ID NO 34
<211> LENGTH: 120
<212> TYPE: PRT
<213> ORGANISM: Artificial Sequence
<220> FEATURE:
<223> OTHER INFORMATION: 23F8 heavy chain

<400> SEQUENCE: 34

Glu Val Gln Leu Val Glu Ser Gly Gly Gly Leu Val Lys Pro Gly Gly
1               5                   10                  15

Ser Arg Lys Leu Ser Cys Ala Ala Ser Gly Phe Thr Phe Ser Asp Tyr
            20                  25                  30

Gly Met His Trp Val Arg Gln Ala Pro Glu Lys Gly Leu Glu Trp Val
        35                  40                  45

Ala Tyr Ile Ser Ser Gly Ser Arg Thr Ile Tyr Tyr Ala Asp Thr Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95
```

```
Ala Arg Leu Gly Tyr Gly Tyr Asp Trp Tyr Phe Asp Val Trp Gly Thr
            100                 105                 110

Gly Thr Thr Val Thr Val Ser Ser
        115                 120

<210> SEQ ID NO 35
<211> LENGTH: 112
<212> TYPE: PRT
<213> ORGANISM: Artificial Sequence
<220> FEATURE:
<223> OTHER INFORMATION: 23F8 light chain

<400> SEQUENCE: 35

Asp Val Val Met Thr Gln Thr Pro Leu Thr Leu Ser Val Thr Ile Gly
1               5                   10                  15

Gln Pro Ala Ser Ile Ser Cys Lys Ser Gln Ser Leu Leu Asp Ser
            20                  25                  30

Asp Gly Arg Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Ile Tyr Tyr Cys Trp Gln Gly
                85                  90                  95

Thr His Phe Pro Gln Thr Phe Gly Gly Gly Thr Lys Leu Glu Ile Lys
            100                 105                 110

<210> SEQ ID NO 36
<211> LENGTH: 5
<212> TYPE: PRT
<213> ORGANISM: Artificial Sequence
<220> FEATURE:
<223> OTHER INFORMATION: 23F8 fragment

<400> SEQUENCE: 36

Asp Tyr Gly Met His
1               5

<210> SEQ ID NO 37
<211> LENGTH: 17
<212> TYPE: PRT
<213> ORGANISM: Artificial Sequence
<220> FEATURE:
<223> OTHER INFORMATION: 23F8 fragment

<400> SEQUENCE: 37

Tyr Ile Ser Ser Gly Ser Arg Thr Ile Tyr Tyr Ala Asp Thr Val Lys
1               5                   10                  15

Gly

<210> SEQ ID NO 38
<211> LENGTH: 11
<212> TYPE: PRT
<213> ORGANISM: Artificial Sequence
<220> FEATURE:
<223> OTHER INFORMATION: 23F8 fragment

<400> SEQUENCE: 38

Leu Gly Tyr Gly Tyr Asp Trp Tyr Phe Asp Val
1               5                   10
```

```
<210> SEQ ID NO 39
<211> LENGTH: 16
<212> TYPE: PRT
<213> ORGANISM: Artificial Sequence
<220> FEATURE:
<223> OTHER INFORMATION: 23F8 fragment

<400> SEQUENCE: 39

Lys Ser Ser Gln Ser Leu Leu Asp Ser Asp Gly Arg Thr Tyr Leu Asn
1               5                   10                  15

<210> SEQ ID NO 40
<211> LENGTH: 7
<212> TYPE: PRT
<213> ORGANISM: Artificial Sequence
<220> FEATURE:
<223> OTHER INFORMATION: 23F8 fragment

<400> SEQUENCE: 40

Leu Val Ser Lys Leu Asp Ser
1               5

<210> SEQ ID NO 41
<211> LENGTH: 9
<212> TYPE: PRT
<213> ORGANISM: Artificial Sequence
<220> FEATURE:
<223> OTHER INFORMATION: 23F8 fragment

<400> SEQUENCE: 41

Trp Gln Gly Thr His Phe Pro Gln Thr
1               5

<210> SEQ ID NO 42
<211> LENGTH: 420
<212> TYPE: DNA
<213> ORGANISM: Artificial Sequence
<220> FEATURE:
<223> OTHER INFORMATION: 18B2 heavy chain

<400> SEQUENCE: 42
atggaatgga gcggggtctt tatctttctc ctgtcagtaa ctgcaggtgt ccactcccag      60
gtccagctgc agcagtctgg agctgagctg gtaaggcctg ggacttcagt gaagatgtcc     120
tgcaaggctg ctggatacac cttcactaac tactggatag ttgggtaaa gcagaggcct     180 ggacatggcc ttgagtggat tggagatatt taccctggag gtgtttatac taactacaat     240
gagaacttca gggcaaggc cacactgacg gcagacacat cctccagcac agcccacatg     300
cagctcagca gcctgacatc tgaggactct gccatctatt actgtgtaag aggagggaag     360
tatggtaact ttttcgctat ggactactgg ggtcaaggaa cgtcagtcac cgtctcctca     420

<210> SEQ ID NO 43
<211> LENGTH: 140
<212> TYPE: PRT
<213> ORGANISM: Artificial Sequence
<220> FEATURE:
<223> OTHER INFORMATION: 18B2 heavy chain

<400> SEQUENCE: 43

Met Glu Trp Ser Gly Val Phe Ile Phe Leu Leu Ser Val Thr Ala Gly
1               5                   10                  15

Val His Ser Gln Val Gln Leu Gln Gln Ser Gly Ala Glu Leu Val Arg
            20                  25                  30
```

-continued

```
Pro Gly Thr Ser Val Lys Met Ser Cys Lys Ala Ala Gly Tyr Thr Phe
             35                  40                  45

Thr Asn Tyr Trp Ile Gly Trp Val Lys Gln Arg Pro Gly His Gly Leu
 50                  55                  60

Glu Trp Ile Gly Asp Ile Tyr Pro Gly Gly Val Tyr Thr Asn Tyr Asn
 65                  70                  75                  80

Glu Asn Phe Lys Gly Lys Ala Thr Leu Thr Ala Asp Thr Ser Ser Ser
                 85                  90                  95

Thr Ala His Met Gln Leu Ser Ser Leu Thr Ser Glu Asp Ser Ala Ile
            100                 105                 110

Tyr Tyr Cys Val Arg Gly Gly Lys Tyr Gly Asn Phe Phe Ala Met Asp
        115                 120                 125

Tyr Trp Gly Gln Gly Thr Ser Val Thr Val Ser Ser
130                 135                 140
```

<210> SEQ ID NO 44
<211> LENGTH: 396
<212> TYPE: DNA
<213> ORGANISM: Artificial Sequence
<220> FEATURE:
<223> OTHER INFORMATION: 18B2 light chain

<400> SEQUENCE: 44

```
atgaggtgct ctcttcagtt cctgggggtg cttatgttct ggatctctgg agtcactggg      60
gatattgtga taacccagga tgaactctcc aatcctgtca cttctggaga atcagtttcc     120
atctcctgca ggtctagtaa gagtctccta tataaggatg gaagacata cttgaattgg      180
tttctgcaga gaccaggaca atctcctcag ctcctgatct atttgatgtc acccgtgca      240
tcaggagtct cagaccggtt tagtggcagt gggtcaggaa cagatttcac cctggaaatc     300
agtagagtga aggctgagga tgtgggtgtg tattactgtc aacaacttgt agagtatcca     360
ttcacgttcg gctcggggac aaaattggaa ataaaa                                396
```

<210> SEQ ID NO 45
<211> LENGTH: 132
<212> TYPE: PRT
<213> ORGANISM: Artificial Sequence
<220> FEATURE:
<223> OTHER INFORMATION: 18B2 light chain

<400> SEQUENCE: 45

```
Met Arg Cys Ser Leu Gln Phe Leu Gly Val Leu Met Phe Trp Ile Ser
 1               5                  10                  15

Gly Val Thr Gly Asp Ile Val Ile Thr Gln Asp Glu Leu Ser Asn Pro
                 20                  25                  30

Val Thr Ser Gly Glu Ser Val Ser Ile Ser Cys Arg Ser Ser Lys Ser
             35                  40                  45

Leu Leu Tyr Lys Asp Gly Lys Thr Tyr Leu Asn Trp Phe Leu Gln Arg
 50                  55                  60

Pro Gly Gln Ser Pro Gln Leu Leu Ile Tyr Leu Met Ser Thr Arg Ala
 65                  70                  75                  80

Ser Gly Val Ser Asp Arg Phe Ser Gly Ser Gly Ser Gly Thr Asp Phe
                 85                  90                  95

Thr Leu Glu Ile Ser Arg Val Lys Ala Glu Asp Val Gly Val Tyr Tyr
            100                 105                 110

Cys Gln Gln Leu Val Glu Tyr Pro Phe Thr Phe Gly Ser Gly Thr Lys
        115                 120                 125
```

Leu Glu Ile Lys
    130

<210> SEQ ID NO 46
<211> LENGTH: 121
<212> TYPE: PRT
<213> ORGANISM: Artificial Sequence
<220> FEATURE:
<223> OTHER INFORMATION: 18B2 heavy chain

<400> SEQUENCE: 46

Gln Val Gln Leu Gln Gln Ser Gly Ala Glu Leu Val Arg Pro Gly Thr
1               5                   10                  15

Ser Val Lys Met Ser Cys Lys Ala Ala Gly Tyr Thr Phe Thr Asn Tyr
            20                  25                  30

Trp Ile Gly Trp Val Lys Gln Arg Pro Gly His Gly Leu Glu Trp Ile
        35                  40                  45

Gly Asp Ile Tyr Pro Gly Gly Val Tyr Thr Asn Tyr Asn Glu Asn Phe
    50                  55                  60

Lys Gly Lys Ala Thr Leu Thr Ala Asp Thr Ser Ser Thr Ala His
65                  70                  75                  80

Met Gln Leu Ser Ser Leu Thr Ser Glu Asp Ser Ala Ile Tyr Tyr Cys
                85                  90                  95

Val Arg Gly Gly Lys Tyr Gly Asn Phe Phe Ala Met Asp Tyr Trp Gly
            100                 105                 110

Gln Gly Thr Ser Val Thr Val Ser Ser
        115                 120

<210> SEQ ID NO 47
<211> LENGTH: 112
<212> TYPE: PRT
<213> ORGANISM: Artificial Sequence
<220> FEATURE:
<223> OTHER INFORMATION: 18B2 light chain

<400> SEQUENCE: 47

Asp Ile Val Ile Thr Gln Asp Glu Leu Ser Asn Pro Val Thr Ser Gly
1               5                   10                  15

Glu Ser Val Ser Ile Ser Cys Arg Ser Ser Lys Ser Leu Leu Tyr Lys
            20                  25                  30

Asp Gly Lys Thr Tyr Leu Asn Trp Phe Leu Gln Arg Pro Gly Gln Ser
        35                  40                  45

Pro Gln Leu Leu Ile Tyr Leu Met Ser Thr Arg Ala Ser Gly Val Ser
    50                  55                  60

Asp Arg Phe Ser Gly Ser Gly Ser Gly Thr Asp Phe Thr Leu Glu Ile
65                  70                  75                  80

Ser Arg Val Lys Ala Glu Asp Val Gly Val Tyr Tyr Cys Gln Gln Leu
                85                  90                  95

Val Glu Tyr Pro Phe Thr Phe Gly Ser Gly Thr Lys Leu Glu Ile Lys
            100                 105                 110

<210> SEQ ID NO 48
<211> LENGTH: 5
<212> TYPE: PRT
<213> ORGANISM: Artificial Sequence
<220> FEATURE:
<223> OTHER INFORMATION: 18B2 fragment

<400> SEQUENCE: 48

Asn Tyr Trp Ile Gly

<210> SEQ ID NO 49
<211> LENGTH: 17
<212> TYPE: PRT
<213> ORGANISM: Artificial Sequence
<220> FEATURE:
<223> OTHER INFORMATION: 18B2 fragment

<400> SEQUENCE: 49

Asp Ile Tyr Pro Gly Gly Val Tyr Thr Asn Tyr Asn Glu Asn Phe Lys
1               5                   10                  15
Gly

<210> SEQ ID NO 50
<211> LENGTH: 12
<212> TYPE: PRT
<213> ORGANISM: Artificial Sequence
<220> FEATURE:
<223> OTHER INFORMATION: 18B2 fragment

<400> SEQUENCE: 50

Gly Gly Lys Tyr Gly Asn Phe Phe Ala Met Asp Tyr
1               5                   10

<210> SEQ ID NO 51
<211> LENGTH: 16
<212> TYPE: PRT
<213> ORGANISM: Artificial Sequence
<220> FEATURE:
<223> OTHER INFORMATION: 18B2 fragment

<400> SEQUENCE: 51

Arg Ser Ser Lys Ser Leu Leu Tyr Lys Asp Gly Lys Thr Tyr Leu Asn
1               5                   10                  15

<210> SEQ ID NO 52
<211> LENGTH: 7
<212> TYPE: PRT
<213> ORGANISM: Artificial Sequence
<220> FEATURE:
<223> OTHER INFORMATION: 18B2 fragment

<400> SEQUENCE: 52

Leu Met Ser Thr Arg Ala Ser
1               5

<210> SEQ ID NO 53
<211> LENGTH: 9
<212> TYPE: PRT
<213> ORGANISM: Artificial Sequence
<220> FEATURE:
<223> OTHER INFORMATION: 18B2 fragment

<400> SEQUENCE: 53

Gln Gln Leu Val Glu Tyr Pro Phe Thr
1               5

<210> SEQ ID NO 54
<211> LENGTH: 408
<212> TYPE: DNA
<213> ORGANISM: Artificial Sequence
<220> FEATURE:
<223> OTHER INFORMATION: 20F4 heavy chain

<400> SEQUENCE: 54

```
atggcttggg tgtggacctt gctattcctg atggcagctg cccaaagtgc ccaagcacag      60
atccagttgg tgcagtctgg acctgagctg aagaagcctg agagacagt caagatctcc      120 tgcaaggctt ctgggtatac cttcacaaac tatggaatga actgggtgaa gcaggctcca     180 ggaaaggggtt taaagtggat gggctggata aacacctaca ctggagagcc aacatatgct    240
gatgacttca agggacggtt tgccttctct ttggaaacct ctgccaccac tgcctatttg     300
cagatcaaca acctcaaaaa tgaggacacg gctacatatt tctgtgcaag ggcggctacg     360
gggtactttg actactgggg ccaaggcacc actctcacag tctcctca                  408
```

<210> SEQ ID NO 55
<211> LENGTH: 136
<212> TYPE: PRT
<213> ORGANISM: Artificial Sequence
<220> FEATURE:
<223> OTHER INFORMATION: 20F4 heavy chain

<400> SEQUENCE: 55

```
Met Ala Trp Val Trp Thr Leu Leu Phe Leu Met Ala Ala Gln Ser
1               5                   10                  15

Ala Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Thr Phe
        35                  40                  45

Thr Asn Tyr Gly Met Asn Trp Val Lys Gln Ala Pro Gly Lys Gly Leu
    50                  55                  60

Lys Trp Met Gly Trp Ile Asn Thr Tyr Thr Gly Glu Pro Thr Tyr Ala
65                  70                  75                  80

Asp Asp Phe Lys Gly Arg Phe Ala Phe Ser Leu Glu Thr Ser Ala Thr
                85                  90                  95

Thr Ala Tyr Leu Gln Ile Asn Asn Leu Lys Asn Glu Asp Thr Ala Thr
            100                 105                 110

Tyr Phe Cys Ala Arg Ala Ala Thr Gly Tyr Phe Asp Tyr Trp Gly Gln
        115                 120                 125

Gly Thr Thr Leu Thr Val Ser Ser
    130                 135
```

<210> SEQ ID NO 56
<211> LENGTH: 396
<212> TYPE: DNA
<213> ORGANISM: Artificial Sequence
<220> FEATURE:
<223> OTHER INFORMATION: 20F4 light chain

<400> SEQUENCE: 56

```
atggattcac aggcccaagt tcttatgttg ctgctgctat gggtatctgg tacctgtggg     60
gacattgtga tgtcacagtc tccatcctcc ctggctgtgt cagcaggaga gaaggttact    120
atgagctgca gtccagtca gagccttta tatagtagca tcaaaagaa ctacttggcc      180 tggtaccagc agaaaccagg gcagtctcct aaactgttga tctactgggc atccactagg    240
gaatctgggg tccctgaccg cttcacaggc agtggatcag ggacagattt cactctcacc    300
atcagcagtg tgaaggctga agacctggcc gtttattact gtcagcaata ttataacgag    360
tacacgttcg gagggggac caagctggaa ataaaa                                396
```

<210> SEQ ID NO 57
<211> LENGTH: 132
<212> TYPE: PRT

<213> ORGANISM: Artificial Sequence
<220> FEATURE:
<223> OTHER INFORMATION: 20F4 light chain

<400> SEQUENCE: 57

Met Asp Ser Gln Ala Gln Val Leu Met Leu Leu Leu Trp Val Ser
1               5                   10                  15

Gly Thr Cys Gly Asp Ile Val Met Ser Gln Ser Pro Ser Ser Leu Ala
            20                  25                  30

Val Ser Ala Gly Glu Lys Val Thr Met Ser Cys Lys Ser Ser Gln Ser
        35                  40                  45

Leu Leu Tyr Ser Ser Asn Gln Lys Asn Tyr Leu Ala Trp Tyr Gln Gln
    50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Lys Ala Glu Asp Leu Ala Val Tyr
            100                 105                 110

Tyr Cys Gln Gln Tyr Tyr Asn Glu Tyr Thr Phe Gly Gly Gly Thr Lys
        115                 120                 125

Leu Glu Ile Lys
        130

<210> SEQ ID NO 58
<211> LENGTH: 117
<212> TYPE: PRT
<213> ORGANISM: Artificial Sequence
<220> FEATURE:
<223> OTHER INFORMATION: 20F4 heavy chain

<400> SEQUENCE: 58

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Thr Thr Ala Tyr
65                  70                  75                  80

Leu Gln Ile Asn Asn Leu Lys Asn Glu Asp Thr Ala Thr Tyr Phe Cys
                85                  90                  95

Ala Arg Ala Ala Thr Gly Tyr Phe Asp Tyr Trp Gly Gln Gly Thr Thr
            100                 105                 110

Leu Thr Val Ser Ser
        115

<210> SEQ ID NO 59
<211> LENGTH: 112
<212> TYPE: PRT
<213> ORGANISM: Artificial Sequence
<220> FEATURE:
<223> OTHER INFORMATION: 20F4 light chain

<400> SEQUENCE: 59

Asp Ile Val Met Ser Gln Ser Pro Ser Ser Leu Ala Val Ser Ala Gly
1               5                   10                  15

```
Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Cys Gln Gln
                85                  90                  95

Tyr Tyr Asn Glu Tyr Thr Phe Gly Gly Gly Thr Lys Leu Glu Ile Lys
            100                 105                 110
```

<210> SEQ ID NO 60
<211> LENGTH: 5
<212> TYPE: PRT
<213> ORGANISM: Artificial Sequence
<220> FEATURE:
<223> OTHER INFORMATION: 20F4 fragment

<400> SEQUENCE: 60

Asn Tyr Gly Met Asn
1               5

<210> SEQ ID NO 61
<211> LENGTH: 17
<212> TYPE: PRT
<213> ORGANISM: Artificial Sequence
<220> FEATURE:
<223> OTHER INFORMATION: 20F4 fragment

<400> SEQUENCE: 61

Trp Ile Asn Thr Tyr Thr Gly Glu Pro Thr Tyr Ala Asp Asp Phe Lys
1               5                   10                  15

Gly

<210> SEQ ID NO 62
<211> LENGTH: 8
<212> TYPE: PRT
<213> ORGANISM: Artificial Sequence
<220> FEATURE:
<223> OTHER INFORMATION: 20F4 fragment

<400> SEQUENCE: 62

Ala Ala Thr Gly Tyr Phe Asp Tyr
1               5

<210> SEQ ID NO 63
<211> LENGTH: 17
<212> TYPE: PRT
<213> ORGANISM: Artificial Sequence
<220> FEATURE:
<223> OTHER INFORMATION: 20F4 fragment

<400> SEQUENCE: 63

Lys Ser Ser Gln Ser Leu Leu Tyr Ser Ser Asn Gln Lys Asn Tyr Leu
1               5                   10                  15

Ala

<210> SEQ ID NO 64
<211> LENGTH: 7
<212> TYPE: PRT

<210> SEQ ID NO 64
<211> LENGTH: 6
<212> TYPE: PRT
<213> ORGANISM: Artificial Sequence
<220> FEATURE:
<223> OTHER INFORMATION: 20F4 fragment

<400> SEQUENCE: 64

Trp Ala Ser Thr Arg Glu Ser
1               5

<210> SEQ ID NO 65
<211> LENGTH: 8
<212> TYPE: PRT
<213> ORGANISM: Artificial Sequence
<220> FEATURE:
<223> OTHER INFORMATION: 20F4 fragment

<400> SEQUENCE: 65

Gln Gln Tyr Tyr Asn Glu Tyr Thr
1               5

<210> SEQ ID NO 66
<211> LENGTH: 438
<212> TYPE: DNA
<213> ORGANISM: Artificial Sequence
<220> FEATURE:
<223> OTHER INFORMATION: 14G11 heavy chain

<400> SEQUENCE: 66
atgaagttgt ggctgaactg gattttcctt gtaacacttt taaatggtat ccagtgtgag      60
gtgaagctgg tggagtctgg aggaggcttg gtacagcctg ggggttctct gagtctctcc     120
tgtgcagctt ctggattcac cttcactgat tactacatga gctgggtccg ccagcctcca     180
gggaaggcac ttgagtggtt gggttttatt agaaacaaag ctaatggtta cacaacagag     240
tacagtgcat ctgtgaaggg tcggttcacc atctccagag ataattccca aagcatcctc     300
tatcttcaaa tgaatgccct gagagctgag gacagtgcca cttattactg tgcaagatat     360
aggcgggatt actacggtag tcttaattac tatactatgg actactgggg tcaaggaacc     420
tcagtcaccg tctcctca                                                   438

<210> SEQ ID NO 67
<211> LENGTH: 146
<212> TYPE: PRT
<213> ORGANISM: Artificial Sequence
<220> FEATURE:
<223> OTHER INFORMATION: 14G11 heavy chain

<400> SEQUENCE: 67

Met Lys Leu Trp Leu Asn Trp Ile Phe Leu Val Thr Leu Leu Asn Gly
1               5                   10                  15

Ile Gln Cys Glu Val Lys Leu Val Glu Ser Gly Gly Gly Leu Val Gln
            20                  25                  30

Pro Gly Gly Ser Leu Ser Leu Ser Cys Ala Ala Ser Gly Phe Thr Phe
        35                  40                  45

Thr Asp Tyr Tyr Met Ser Trp Val Arg Gln Pro Pro Gly Lys Ala Leu
    50                  55                  60

Glu Trp Leu Gly Phe Ile Arg Asn Lys Ala Asn Gly Tyr Thr Thr Glu
65                  70                  75                  80

Tyr Ser Ala Ser Val Lys Gly Arg Phe Thr Ile Ser Arg Asp Asn Ser
                85                  90                  95

Gln Ser Ile Leu Tyr Leu Gln Met Asn Ala Leu Arg Ala Glu Asp Ser
            100                 105                 110

Ala Thr Tyr Tyr Cys Ala Arg Tyr Arg Arg Asp Tyr Gly Ser Leu
            115                 120                 125

Asn Tyr Tyr Thr Met Asp Tyr Trp Gly Gln Gly Thr Ser Val Thr Val
130                 135                 140

Ser Ser
145

<210> SEQ ID NO 68
<211> LENGTH: 381
<212> TYPE: DNA
<213> ORGANISM: Artificial Sequence
<220> FEATURE:
<223> OTHER INFORMATION: 14G11 light chain

<400> SEQUENCE: 68

```
atgagtgtgc ccactcaggt cctggggttg ctgctgctgt ggcttacagg tgccagatgt      60
gacatccaga tgactcagtc tccagcctcc ctatctgcat ctgtgggaga aactgtcacc     120
atcacatgtc gagcaagtga aaatatttac agttatttag catggtatca gcagaaacag     180
ggaaaatctc ctcagctcct ggtctataat gcaaaaacct tagcagaagg tgtgccatca     240
aggttcagtg gcagtggatc aggcacacag ttttctctga agatcaacag cctgcagcct     300
gaagattttg ggagttatta ctgtcaaaat cattatggta ttcctctcac gttcggtgct     360
gggaccaagc tggagctgaa a                                                381
```

<210> SEQ ID NO 69
<211> LENGTH: 127
<212> TYPE: PRT
<213> ORGANISM: Artificial Sequence
<220> FEATURE:
<223> OTHER INFORMATION: 14G11 light chain

<400> SEQUENCE: 69

Met Ser Val Pro Thr Gln Val Leu Gly Leu Leu Leu Leu Trp Leu Thr
1               5                   10                  15

Gly Ala Arg Cys Asp Ile Gln Met Thr Gln Ser Pro Ala Ser Leu Ser
                20                  25                  30

Ala Ser Val Gly Glu Thr Val Thr Ile Thr Cys Arg Ala Ser Glu Asn
            35                  40                  45

Ile Tyr Ser Tyr Leu Ala Trp Tyr Gln Gln Lys Gln Gly Lys Ser Pro
        50                  55                  60

Gln Leu Leu Val Tyr Asn Ala Lys Thr Leu Ala Glu Gly Val Pro Ser
65                  70                  75                  80

Arg Phe Ser Gly Ser Gly Ser Gly Thr Gln Phe Ser Leu Lys Ile Asn
                85                  90                  95

Ser Leu Gln Pro Glu Asp Phe Gly Ser Tyr Tyr Cys Gln Asn His Tyr
            100                 105                 110

Gly Ile Pro Leu Thr Phe Gly Ala Gly Thr Lys Leu Glu Leu Lys
        115                 120                 125

<210> SEQ ID NO 70
<211> LENGTH: 127
<212> TYPE: PRT
<213> ORGANISM: Artificial Sequence
<220> FEATURE:
<223> OTHER INFORMATION: 14G11 heavy chain

<400> SEQUENCE: 70

Glu Val Lys Leu Val Glu Ser Gly Gly Gly Leu Val Gln Pro Gly Gly
1               5                   10                  15

```
Ser Leu Ser Leu Ser Cys Ala Ala Ser Gly Phe Thr Phe Thr Asp Tyr
            20                  25                  30

Tyr Met Ser Trp Val Arg Gln Pro Pro Gly Lys Ala Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Gln Ser Ile
65                  70                  75                  80

Leu Tyr Leu Gln Met Asn Ala Leu Arg Ala Glu Asp Ser Ala Thr Tyr
                85                  90                  95

Tyr Cys Ala Arg Tyr Arg Arg Asp Tyr Tyr Gly Ser Leu Asn Tyr Tyr
            100                 105                 110

Thr Met Asp Tyr Trp Gly Gln Gly Thr Ser Val Thr Val Ser Ser
        115                 120                 125
```

<210> SEQ ID NO 71
<211> LENGTH: 107
<212> TYPE: PRT
<213> ORGANISM: Artificial Sequence
<220> FEATURE:
<223> OTHER INFORMATION: 14G11 light chain

<400> SEQUENCE: 71

```
Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln Asn His Tyr Gly Ile Pro Leu
                85                  90                  95

Thr Phe Gly Ala Gly Thr Lys Leu Glu Leu Lys
            100                 105
```

<210> SEQ ID NO 72
<211> LENGTH: 5
<212> TYPE: PRT
<213> ORGANISM: Artificial Sequence
<220> FEATURE:
<223> OTHER INFORMATION: 14G11 fragment

<400> SEQUENCE: 72

```
Asp Tyr Tyr Met Ser
1               5
```

<210> SEQ ID NO 73
<211> LENGTH: 19
<212> TYPE: PRT
<213> ORGANISM: Artificial Sequence
<220> FEATURE:
<223> OTHER INFORMATION: 14G11 fragment

<400> SEQUENCE: 73

```
Phe Ile Arg Asn Lys Ala Asn Gly Tyr Thr Thr Glu Tyr Ser Ala Ser
1               5                   10                  15
```

Val Lys Gly

<210> SEQ ID NO 74
<211> LENGTH: 16
<212> TYPE: PRT
<213> ORGANISM: Artificial Sequence
<220> FEATURE:
<223> OTHER INFORMATION: 14G11 fragment

<400> SEQUENCE: 74

Tyr Arg Arg Asp Tyr Tyr Gly Ser Leu Asn Tyr Tyr Thr Met Asp Tyr
1               5                   10                  15

<210> SEQ ID NO 75
<211> LENGTH: 11
<212> TYPE: PRT
<213> ORGANISM: Artificial Sequence
<220> FEATURE:
<223> OTHER INFORMATION: 14G11 fragment

<400> SEQUENCE: 75

Arg Ala Ser Glu Asn Ile Tyr Ser Tyr Leu Ala
1               5                   10

<210> SEQ ID NO 76
<211> LENGTH: 7
<212> TYPE: PRT
<213> ORGANISM: Artificial Sequence
<220> FEATURE:
<223> OTHER INFORMATION: 14G11 fragment

<400> SEQUENCE: 76

Asn Ala Lys Thr Leu Ala Glu
1               5

<210> SEQ ID NO 77
<211> LENGTH: 9
<212> TYPE: PRT
<213> ORGANISM: Artificial Sequence
<220> FEATURE:
<223> OTHER INFORMATION: 14G11 fragment

<400> SEQUENCE: 77

Gln Asn His Tyr Gly Ile Pro Leu Thr
1               5

<210> SEQ ID NO 78
<211> LENGTH: 411
<212> TYPE: DNA
<213> ORGANISM: Artificial Sequence
<220> FEATURE:
<223> OTHER INFORMATION: 13E11 heavy chain

<400> SEQUENCE: 78
atggactcca ggctcaattt agttttcctt gtccttattt taaaaggtgt ccagtgtgag      60
gtgcagctgg tggagtctgg gggaggctta gtgaagcctg agggtcccg gaaactctcc     120 tgtgcagcct ctggattcac tttcagtgac tatggaatgc actgggttcg tcaggctcca     180
gagaaggggc tggagtgggt tgcatacatt agtagtggca gtagtaccat ctactatgca     240
gacacagtga agggccgatt caccatctcc agagacaatg ccaagaacac cctgttcctg     300
caaatgacga gtctaaggtc tgaggacacg gccatgtatt actgtgcaag gccccgaagt     360
gggaggtact ttgactactg gggccaaggc accactctca cagtctcctc a              411

<210> SEQ ID NO 79
<211> LENGTH: 137
<212> TYPE: PRT
<213> ORGANISM: Artificial Sequence
<220> FEATURE:
<223> OTHER INFORMATION: 13E11 heavy chain

<400> SEQUENCE: 79

Met Asp Ser Arg Leu Asn Leu Val Phe Leu Val Ile Leu Lys Gly
1               5                   10                  15

Val Gln Cys Glu Val Gln Leu Val Glu Ser Gly Gly Gly Leu Val Lys
            20                  25                  30

Pro Gly Gly Ser Arg Lys Leu Ser Cys Ala Ala Ser Gly Phe Thr Phe
        35                  40                  45

Ser Asp Tyr Gly Met His Trp Val Arg Gln Ala Pro Glu Lys Gly Leu
    50                  55                  60

Glu Trp Val Ala Tyr Ile Ser Ser Gly Ser Ser Thr Ile Tyr Tyr Ala
65              70                  75                  80

Asp Thr Val Lys Gly Arg Phe Thr Ile Ser Arg Asp Asn Ala Lys Asn
                85                  90                  95

Thr Leu Phe Leu Gln Met Thr Ser Leu Arg Ser Glu Asp Thr Ala Met
            100                 105                 110

Tyr Tyr Cys Ala Arg Pro Arg Ser Gly Arg Tyr Phe Asp Tyr Trp Gly
        115                 120                 125

Gln Gly Thr Thr Leu Thr Val Ser Ser
        130                 135

<210> SEQ ID NO 80
<211> LENGTH: 393
<212> TYPE: DNA
<213> ORGANISM: Artificial Sequence
<220> FEATURE:
<223> OTHER INFORMATION: 13E11 light chain

<400> SEQUENCE: 80
atgagtcctg cccagttcct gtttctgtta gtgctctgga ttcaggaaac caacggtgat      60
gttatgatga cccagactcc actcactttg tcggttacca ttggacaacc agcttccatc     120
tcttgcaagt caagtcagag cctcttagat agtaacggaa ataccatctc gcattggtta    180
ttacagaggc caggccagtc tccaaagatc ctaatctatc tggtgtctaa actggactct    240
ggagtccctg acaggttcag tggcagtggg tcaggaacag atttcacact gaaaatcagc    300
agagtggagg ctgaggattt gggagtttat tactgcttgc aaggtacaca ttttccgtac    360
acgttcggag gggggaccaa gctggaaata aaa                                  393

<210> SEQ ID NO 81
<211> LENGTH: 131
<212> TYPE: PRT
<213> ORGANISM: Artificial Sequence
<220> FEATURE:
<223> OTHER INFORMATION: 13E11 light chain

<400> SEQUENCE: 81

Met Ser Pro Ala Gln Phe Leu Phe Leu Leu Val Leu Trp Ile Gln Glu
1               5                   10                  15

Thr Asn Gly Asp Val Met Met Thr Gln Thr Pro Leu Thr Leu Ser Val
            20                  25                  30

Thr Ile Gly Gln Pro Ala Ser Ile Ser Cys Lys Ser Ser Gln Ser Leu
        35                  40                  45

```
Leu Asp Ser Asn Gly Asn Thr Tyr Leu His Trp Leu Gln Arg Pro
        50                  55                  60

Gly Gln Ser Pro Lys Ile Leu Ile Tyr Leu Val Ser Lys Leu Asp Ser
 65                  70                  75                  80

Gly Val Pro Asp Arg Phe Ser Gly Ser Gly Ser Gly Thr Asp Phe Thr
                     85                  90                  95

Leu Lys Ile Ser Arg Val Glu Ala Glu Asp Leu Gly Val Tyr Tyr Cys
                100                 105                 110

Leu Gln Gly Thr His Phe Pro Tyr Thr Phe Gly Gly Gly Thr Lys Leu
            115                 120                 125

Glu Ile Lys
        130

<210> SEQ ID NO 82
<211> LENGTH: 118
<212> TYPE: PRT
<213> ORGANISM: Artificial Sequence
<220> FEATURE:
<223> OTHER INFORMATION: 13E11 heavy chain

<400> SEQUENCE: 82

Glu Val Gln Leu Val Glu Ser Gly Gly Gly Leu Val Lys Pro Gly Gly
  1               5                  10                  15

Ser Arg Lys Leu Ser Cys Ala Ala Ser Gly Phe Thr Phe Ser Asp Tyr
                 20                  25                  30

Gly Met His Trp Val Arg Gln Ala Pro Glu Lys Gly Leu Glu Trp Val
             35                  40                  45

Ala Tyr Ile Ser Ser Gly Ser Ser Thr Ile Tyr Tyr Ala Asp Thr Val
 50                  55                  60

Lys Gly Arg Phe Thr Ile Ser Arg Asp Asn Ala Lys Asn Thr Leu Phe
 65                  70                  75                  80

Leu Gln Met Thr Ser Leu Arg Ser Glu Asp Thr Ala Met Tyr Tyr Cys
                 85                  90                  95

Ala Arg Pro Arg Ser Gly Arg Tyr Phe Asp Tyr Trp Gly Gln Gly Thr
                100                 105                 110

Thr Leu Thr Val Ser Ser
            115

<210> SEQ ID NO 83
<211> LENGTH: 112
<212> TYPE: PRT
<213> ORGANISM: Artificial Sequence
<220> FEATURE:
<223> OTHER INFORMATION: 13E11 light chain

<400> SEQUENCE: 83

Asp Val Met Met Thr Gln Thr Pro Leu Thr Leu Ser Val Thr Ile Gly
  1               5                  10                  15

Gln Pro Ala Ser Ile Ser Cys Lys Ser Ser Gln Ser Leu Leu Asp Ser
                 20                  25                  30

Asn Gly Asn Thr Tyr Leu His Trp Leu Leu Gln Arg Pro Gly Gln Ser
             35                  40                  45

Pro Lys Ile Leu Ile Tyr Leu Val Ser Lys Leu Asp Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Leu Gln Gly
                 85                  90                  95
```

```
Thr His Phe Pro Tyr Thr Phe Gly Gly Gly Thr Lys Leu Glu Ile Lys
            100                 105                 110

<210> SEQ ID NO 84
<211> LENGTH: 5
<212> TYPE: PRT
<213> ORGANISM: Artificial Sequence
<220> FEATURE:
<223> OTHER INFORMATION: 13E11 fragment

<400> SEQUENCE: 84

Asp Tyr Gly Met His
1               5

<210> SEQ ID NO 85
<211> LENGTH: 17
<212> TYPE: PRT
<213> ORGANISM: Artificial Sequence
<220> FEATURE:
<223> OTHER INFORMATION: 13E11 fragment

<400> SEQUENCE: 85

Tyr Ile Ser Ser Gly Ser Ser Thr Ile Tyr Tyr Ala Asp Thr Val Lys
1               5                   10                  15
Gly

<210> SEQ ID NO 86
<211> LENGTH: 9
<212> TYPE: PRT
<213> ORGANISM: Artificial Sequence
<220> FEATURE:
<223> OTHER INFORMATION: 13E11 fragment

<400> SEQUENCE: 86

Pro Arg Ser Gly Arg Tyr Phe Asp Tyr
1               5

<210> SEQ ID NO 87
<211> LENGTH: 16
<212> TYPE: PRT
<213> ORGANISM: Artificial Sequence
<220> FEATURE:
<223> OTHER INFORMATION: 13E11 fragment

<400> SEQUENCE: 87

Lys Ser Ser Gln Ser Leu Leu Asp Ser Asn Gly Asn Thr Tyr Leu His
1               5                   10                  15

<210> SEQ ID NO 88
<211> LENGTH: 7
<212> TYPE: PRT
<213> ORGANISM: Artificial Sequence
<220> FEATURE:
<223> OTHER INFORMATION: 13E11 fragment

<400> SEQUENCE: 88

Leu Val Ser Lys Leu Asp Ser
1               5

<210> SEQ ID NO 89
<211> LENGTH: 9
<212> TYPE: PRT
<213> ORGANISM: Artificial Sequence
<220> FEATURE:
<223> OTHER INFORMATION: 13E11 fragment
```

<400> SEQUENCE: 89

Leu Gln Gly Thr His Phe Pro Tyr Thr
1               5

<210> SEQ ID NO 90
<211> LENGTH: 393
<212> TYPE: DNA
<213> ORGANISM: Artificial Sequence
<220> FEATURE:
<223> OTHER INFORMATION: 10B1 heavy chain

<400> SEQUENCE: 90

```
atgaaatgca gctgggttat cttcttcctg atggcagtgg ttacaggggt caattcagag     60
gttcagctgc agcagtctgg ggcagagctt gtgaagccag ggcctcagt caagttgtcc    120
tgcacagctt ctggcttcaa cattaaagac acctatatac actgggtgaa acagaggcct    180
gaacagggcc tggagtggat tggaaggatt gatcctgcga atggtaatac tatatatgcc    240
tcaaagttcc agggcaaggc ccctataaca gcagtcacat catccaacac agcctacatg    300
cagttcagca gcctgacatc tggggacact gccgtctatt actgtactgc tatggactac    360
tggggtcaag gaacctcagt caccgtctcc tca                                 393
```

<210> SEQ ID NO 91
<211> LENGTH: 131
<212> TYPE: PRT
<213> ORGANISM: Artificial Sequence
<220> FEATURE:
<223> OTHER INFORMATION: 10B1 heavy chain

<400> SEQUENCE: 91

Met Lys Cys Ser Trp Val Ile Phe Phe Leu Met Ala Val Val Thr Gly
1               5                   10                  15
Val Asn Ser Glu Val Gln Leu Gln Gln Ser Gly Ala Glu Leu Val Lys
            20                  25                  30
Pro Gly Ala Ser Val Lys Leu Ser Cys Thr Ala Ser Gly Phe Asn Ile
        35                  40                  45
Lys Asp Thr Tyr Ile His Trp Val Lys Gln Arg Pro Glu Gln Gly Leu
    50                  55                  60
Glu Trp Ile Gly Arg Ile Asp Pro Ala Asn Gly Asn Thr Ile Tyr Ala
65                  70                  75                  80
Ser Lys Phe Gln Gly Lys Ala Pro Ile Thr Ala Val Thr Ser Ser Asn
                85                  90                  95
Thr Ala Tyr Met Gln Phe Ser Ser Leu Thr Ser Gly Asp Thr Ala Val
            100                 105                 110
Tyr Tyr Cys Thr Ala Met Asp Tyr Trp Gly Gln Gly Thr Ser Val Thr
        115                 120                 125
Val Ser Ser
    130

<210> SEQ ID NO 92
<211> LENGTH: 393
<212> TYPE: DNA
<213> ORGANISM: Artificial Sequence
<220> FEATURE:
<223> OTHER INFORMATION: 10B1 light chain

<400> SEQUENCE: 92

```
atgagtcctg cccagttcct gtttctgcta gtgctcgcga ttcaggaaac caacggtgat     60
gttgtgatga ctcagacccc actcactttg tcggttacca ttggacaacc agcctccatc    120
```

-continued

```
tcttgcaaat caagtcagag cctcttacat agtaatggaa agacatattt gaattggtta       180
ttacagaggc caggccagtc tccaaagctc ctaatctatc tggtgtctaa actggattct       240
ggagtccctg acaggttcag tggcagtgga tcagggacag atttcacact gaaaatcagc       300
agagtggagg ctgaggattt gggagtttat tactgcttgc aagctacaca ttttcctcat       360
acgttcggat cggggaccaa gctggaaata aaa                                    393
```

<210> SEQ ID NO 93
<211> LENGTH: 131
<212> TYPE: PRT
<213> ORGANISM: Artificial Sequence
<220> FEATURE:
<223> OTHER INFORMATION: 10B1 light chain

<400> SEQUENCE: 93

```
Met Ser Pro Ala Gln Phe Leu Phe Leu Leu Val Leu Ala Ile Gln Glu
1               5                   10                  15

Thr Asn Gly Asp Val Val Met Thr Gln Thr Pro Leu Thr Leu Ser Val
            20                  25                  30

Thr Ile Gly Gln Pro Ala Ser Ile Ser Cys Lys Ser Gln Ser Leu
        35                  40                  45

Leu His Ser Asn Gly Lys Thr Tyr Leu Asn Trp Leu Leu Gln Arg Pro
    50                  55                  60

Gly Gln Ser Pro Lys Leu Leu Ile Tyr Leu Val Ser Lys Leu Asp Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Leu Gln Ala Thr His Phe Pro His Thr Phe Gly Ser Gly Thr Lys Leu
        115                 120                 125

Glu Ile Lys
        130
```

<210> SEQ ID NO 94
<211> LENGTH: 112
<212> TYPE: PRT
<213> ORGANISM: Artificial Sequence
<220> FEATURE:
<223> OTHER INFORMATION: 10B1 heavy chain

<400> SEQUENCE: 94

```
Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Ile His Trp Val Lys Gln Arg Pro Glu Gln Gly Leu Glu Trp Ile
        35                  40                  45

Gly Arg Ile Asp Pro Ala Asn Gly Asn Thr Ile Tyr Ala Ser Lys Phe
    50                  55                  60

Gln Gly Lys Ala Pro Ile Thr Ala Val Thr Ser Ser Asn Thr Ala Tyr
65                  70                  75                  80

Met Gln Phe Ser Ser Leu Thr Ser Gly Asp Thr Ala Val Tyr Tyr Cys
                85                  90                  95

Thr Ala Met Asp Tyr Trp Gly Gln Gly Thr Ser Val Thr Val Ser Ser
            100                 105                 110
```

<210> SEQ ID NO 95
<211> LENGTH: 112
<212> TYPE: PRT
<213> ORGANISM: Artificial Sequence
<220> FEATURE:
<223> OTHER INFORMATION: 10B1 light chain

<400> SEQUENCE: 95

```
Asp Val Val Met Thr Gln Thr Pro Leu Thr Leu Ser Val Thr Ile Gly
1               5                   10                  15

Gln Pro Ala Ser Ile Ser Cys Lys Ser Gln Ser Leu Leu His Ser
            20                  25                  30

Asn Gly Lys Thr Tyr Leu Asn Trp Leu Leu Gln Arg Pro Gly Gln Ser
            35                  40                  45

Pro Lys Leu Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Leu Gln Ala
                85                  90                  95

Thr His Phe Pro His Thr Phe Gly Ser Gly Thr Lys Leu Glu Ile Lys
            100                 105                 110
```

<210> SEQ ID NO 96
<211> LENGTH: 5
<212> TYPE: PRT
<213> ORGANISM: Artificial Sequence
<220> FEATURE:
<223> OTHER INFORMATION: 10B1 fragment

<400> SEQUENCE: 96

```
Asp Thr Tyr Ile His
1               5
```

<210> SEQ ID NO 97
<211> LENGTH: 17
<212> TYPE: PRT
<213> ORGANISM: Artificial Sequence
<220> FEATURE:
<223> OTHER INFORMATION: 10B1 fragment

<400> SEQUENCE: 97

```
Arg Ile Asp Pro Ala Asn Gly Asn Thr Ile Tyr Ala Ser Lys Phe Gln
1               5                   10                  15

Gly
```

<210> SEQ ID NO 98
<211> LENGTH: 3
<212> TYPE: PRT
<213> ORGANISM: Artificial Sequence
<220> FEATURE:
<223> OTHER INFORMATION: 10B1 fragment

<400> SEQUENCE: 98

```
Met Asp Tyr
1
```

<210> SEQ ID NO 99
<211> LENGTH: 16
<212> TYPE: PRT
<213> ORGANISM: Artificial Sequence
<220> FEATURE:
<223> OTHER INFORMATION: 10B1 fragment

<400> SEQUENCE: 99

Lys Ser Ser Gln Ser Leu Leu His Ser Asn Gly Lys Thr Tyr Leu Asn
1               5                   10                  15

<210> SEQ ID NO 100
<211> LENGTH: 7
<212> TYPE: PRT
<213> ORGANISM: Artificial Sequence
<220> FEATURE:
<223> OTHER INFORMATION: 10B1 fragment

<400> SEQUENCE: 100

Leu Val Ser Lys Leu Asp Ser
1               5

<210> SEQ ID NO 101
<211> LENGTH: 9
<212> TYPE: PRT
<213> ORGANISM: Artificial Sequence
<220> FEATURE:
<223> OTHER INFORMATION: 10B1 fragment

<400> SEQUENCE: 101

Leu Gln Ala Thr His Phe Pro His Thr
1               5

<210> SEQ ID NO 102
<211> LENGTH: 393
<212> TYPE: DNA
<213> ORGANISM: Artificial Sequence
<220> FEATURE:
<223> OTHER INFORMATION: 7E11 heavy chain

<400> SEQUENCE: 102
atgaaatgca gctgggttat cttcttcctg atggcagtgg ttacaggggt caattcagag      60
gttcagctgc agcagtctgg ggcagagctt gtgaagccag gggcctcagt caagttgtcc     120
tgcacagctt ctggcttcaa cattaaagac acctatatac actgggtgaa gcagaggcct     180
gaacagggcc tggagtggat tggaaggatt gatcctgcga atggtaatat tatatatgcc     240
tcaaagttcc agggcgaggc cactataaca gcagacacat catccaacac agcctacatg     300
cagctcagca gcctgacatc tgggacactg ccgtctatt actgtagcgc tatggactac     360
tggggtcaag gaacctcagt caccgtctcc tca                                  393

<210> SEQ ID NO 103
<211> LENGTH: 131
<212> TYPE: PRT
<213> ORGANISM: Artificial Sequence
<220> FEATURE:
<223> OTHER INFORMATION: 7E11 heavy chain

<400> SEQUENCE: 103

Met Lys Cys Ser Trp Val Ile Phe Phe Leu Met Ala Val Val Thr Gly
1               5                   10                  15

Val Asn Ser Glu Val Gln Leu Gln Gln Ser Gly Ala Glu Leu Val Lys
            20                  25                  30

Pro Gly Ala Ser Val Lys Leu Ser Cys Thr Ala Ser Gly Phe Asn Ile
        35                  40                  45

Lys Asp Thr Tyr Ile His Trp Val Lys Gln Arg Pro Glu Gln Gly Leu
    50                  55                  60

Glu Trp Ile Gly Arg Ile Asp Pro Ala Asn Gly Asn Ile Ile Tyr Ala 65                  70                  75                  80
Ser Lys Phe Gln Gly Glu Ala Thr Ile Thr Ala Asp Thr Ser Ser Asn
                    85                  90                  95

Thr Ala Tyr Met Gln Leu Ser Ser Leu Thr Ser Gly Asp Thr Ala Val
                100                 105                 110

Tyr Tyr Cys Ser Ala Met Asp Tyr Trp Gly Gln Gly Thr Ser Val Thr
            115                 120                 125

Val Ser Ser
    130

<210> SEQ ID NO 104
<211> LENGTH: 393
<212> TYPE: DNA
<213> ORGANISM: Artificial Sequence
<220> FEATURE:
<223> OTHER INFORMATION: 7E11 light chain

<400> SEQUENCE: 104
atgagtcctg cccagttcct gtttctgcta gtgctctcga ttcaggaaac caacggtgat      60
gttgtgatga ctcagacccc actcactttg tcgcttacca ttggacaacc agcctccatc     120
tcttgcaaat caagtcagag cctcttacat agtaatggaa agacatattt gaattggtta    180
ttacagaggc caggccagtc tcctaagctc ctcatctatc tggtgtctaa actggattct    240
ggagtccctg acaggttcag tggcagtgga tcagggacag atttcacact gaaaatcagc    300
agagtggagg ctgaggattt gggagtttat tactgcttgc aagctacaca ttttcctcat    360
acgttcggat cggggaccaa gctggaaata aaa                                 393

<210> SEQ ID NO 105
<211> LENGTH: 131
<212> TYPE: PRT
<213> ORGANISM: Artificial Sequence
<220> FEATURE:
<223> OTHER INFORMATION: 7E11 light chain

<400> SEQUENCE: 105

Met Ser Pro Ala Gln Phe Leu Phe Leu Leu Val Leu Ser Ile Gln Glu
1               5                   10                  15

Thr Asn Gly Asp Val Val Met Thr Gln Thr Pro Leu Thr Leu Ser Leu
            20                  25                  30

Thr Ile Gly Gln Pro Ala Ser Ile Ser Cys Lys Ser Ser Gln Ser Leu
        35                  40                  45

Leu His Ser Asn Gly Lys Thr Tyr Leu Asn Trp Leu Leu Gln Arg Pro
    50                  55                  60

Gly Gln Ser Pro Lys Leu Leu Ile Tyr Leu Val Ser Lys Leu Asp Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Leu Gln Ala Thr His Phe Pro His Thr Phe Gly Ser Gly Thr Lys Leu
        115                 120                 125

Glu Ile Lys
    130

<210> SEQ ID NO 106
<211> LENGTH: 112
<212> TYPE: PRT

```
<213> ORGANISM: Artificial Sequence
<220> FEATURE:
<223> OTHER INFORMATION: 7E11 heavy chain

<400> SEQUENCE: 106

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Ile His Trp Val Lys Gln Arg Pro Glu Gln Gly Leu Glu Trp Ile
        35                  40                  45

Gly Arg Ile Asp Pro Ala Asn Gly Asn Ile Ile Tyr Ala Ser Lys Phe
    50                  55                  60

Gln Gly Glu Ala Thr Ile Thr Ala Asp Thr Ser Ser Asn Thr Ala Tyr
65                  70                  75                  80

Met Gln Leu Ser Ser Leu Thr Ser Gly Asp Thr Ala Val Tyr Tyr Cys
                85                  90                  95

Ser Ala Met Asp Tyr Trp Gly Gln Gly Thr Ser Val Thr Val Ser Ser
            100                 105                 110

<210> SEQ ID NO 107
<211> LENGTH: 112
<212> TYPE: PRT
<213> ORGANISM: Artificial Sequence
<220> FEATURE:
<223> OTHER INFORMATION: 7E11 light chain

<400> SEQUENCE: 107

Asp Val Val Met Thr Gln Thr Pro Leu Thr Leu Ser Leu Thr Ile Gly
1               5                   10                  15

Gln Pro Ala Ser Ile Ser Cys Lys Ser Ser Gln Ser Leu Leu His Ser
            20                  25                  30

Asn Gly Lys Thr Tyr Leu Asn Trp Leu Leu Gln Arg Pro Gly Gln Ser
        35                  40                  45

Pro Lys Leu Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Leu Gln Ala
                85                  90                  95

Thr His Phe Pro His Thr Phe Gly Ser Gly Thr Lys Leu Glu Ile Lys
            100                 105                 110

<210> SEQ ID NO 108
<211> LENGTH: 5
<212> TYPE: PRT
<213> ORGANISM: Artificial Sequence
<220> FEATURE:
<223> OTHER INFORMATION: 7E11 fragment

<400> SEQUENCE: 108

Asp Thr Tyr Ile His
1               5

<210> SEQ ID NO 109
<211> LENGTH: 17
<212> TYPE: PRT
<213> ORGANISM: Artificial Sequence
<220> FEATURE:
<223> OTHER INFORMATION: 7E11 fragment
```

<400> SEQUENCE: 109

Arg Ile Asp Pro Ala Asn Gly Asn Ile Ile Tyr Ala Ser Lys Phe Gln
1               5                   10                  15
Gly

<210> SEQ ID NO 110
<211> LENGTH: 3
<212> TYPE: PRT
<213> ORGANISM: Artificial Sequence
<220> FEATURE:
<223> OTHER INFORMATION: 7E11 fragment

<400> SEQUENCE: 110

Met Asp Tyr
1

<210> SEQ ID NO 111
<211> LENGTH: 16
<212> TYPE: PRT
<213> ORGANISM: Artificial Sequence
<220> FEATURE:
<223> OTHER INFORMATION: 7E11 fragment

<400> SEQUENCE: 111

Lys Ser Ser Gln Ser Leu Leu His Ser Asn Gly Lys Thr Tyr Leu Asn
1               5                   10                  15

<210> SEQ ID NO 112
<211> LENGTH: 7
<212> TYPE: PRT
<213> ORGANISM: Artificial Sequence
<220> FEATURE:
<223> OTHER INFORMATION: 7E11 fragment

<400> SEQUENCE: 112

Leu Val Ser Lys Leu Asp Ser
1               5

<210> SEQ ID NO 113
<211> LENGTH: 9
<212> TYPE: PRT
<213> ORGANISM: Artificial Sequence
<220> FEATURE:
<223> OTHER INFORMATION: 7E11 fragment

<400> SEQUENCE: 113

Leu Gln Ala Thr His Phe Pro His Thr
1               5

<210> SEQ ID NO 114
<211> LENGTH: 414
<212> TYPE: DNA
<213> ORGANISM: Artificial Sequence
<220> FEATURE:
<223> OTHER INFORMATION: 3E6 heavy chain

<400> SEQUENCE: 114
atgaagttgt ggctgaactg gatttcctt gtaacactt taaatggtat ccagtgtgag      60
gtgaagctgg tggagtctgg aggaggcttg gtacagcctg ggggttctct gagactctcc    120
tgtgcaactt ctgggttcac cttcactgat tactacatga gctgggtccg ccagcctcca    180
ggaaaggcac ttgagtggat gggttttatt agaaacaaag ctaaaggtta cacaacagat    240
tacagtgcgt ctgtgaaggg tcggttcacc atctccagag atgattccca aagcatcctc    300
tatcttcaaa tgaacaccct gagacctgag gacagtgcca cttattactg tgcaagaaac    360
tatgactatt ctatggacta ctggggtcaa ggaacctcag tcaccgtctc ctca    414

<210> SEQ ID NO 115
<211> LENGTH: 138
<212> TYPE: PRT
<213> ORGANISM: Artificial Sequence
<220> FEATURE:
<223> OTHER INFORMATION: 3E6 heavy chain

<400> SEQUENCE: 115

Met Lys Leu Trp Leu Asn Trp Ile Phe Leu Val Thr Leu Leu Asn Gly
1               5                   10                  15

Ile Gln Cys Glu Val Lys Leu Val Glu Ser Gly Gly Gly Leu Val Gln
            20                  25                  30

Pro Gly Gly Ser Leu Arg Leu Ser Cys Ala Thr Ser Gly Phe Thr Phe
        35                  40                  45

Thr Asp Tyr Tyr Met Ser Trp Val Arg Gln Pro Pro Gly Lys Ala Leu
    50                  55                  60

Glu Trp Met Gly Phe Ile Arg Asn Lys Ala Lys Gly Tyr Thr Thr Asp
65                  70                  75                  80

Tyr Ser Ala Ser Val Lys Gly Arg Phe Thr Ile Ser Arg Asp Asp Ser
                85                  90                  95

Gln Ser Ile Leu Tyr Leu Gln Met Asn Thr Leu Arg Pro Glu Asp Ser
            100                 105                 110

Ala Thr Tyr Tyr Cys Ala Arg Asn Tyr Asp Tyr Ser Met Asp Tyr Trp
        115                 120                 125

Gly Gln Gly Thr Ser Val Thr Val Ser Ser
    130                 135

<210> SEQ ID NO 116
<211> LENGTH: 381
<212> TYPE: DNA
<213> ORGANISM: Artificial Sequence
<220> FEATURE:
<223> OTHER INFORMATION: 3E6 light chain

<400> SEQUENCE: 116
atgagtgtgc tcactcaggt cctggcgttg ctgctgctgt ggcttacagg tgccagatgt    60
gacatccagc tgactcagtc tccagcctcc tatctgcat ctgtgggaga aactgtcacc    120
atcacttgtc gagcaagtga ataattcac aaatatttag catggtatca gcagaaacag    180
ggaaagtctc ctcagcgcct ggtctataat gcaaaaacct tagcagatgg tgtgccatca    240
aggttcaatg gcagtggatc aggaacacaa tattctctca agatcaatag cctgcagcct    300
gaagattttg ggattatta ctgtcaacat ttttggagta ctccgctcac gttcggtgct    360
gggaccaagc tggagctgaa a    381

<210> SEQ ID NO 117
<211> LENGTH: 127
<212> TYPE: PRT
<213> ORGANISM: Artificial Sequence
<220> FEATURE:
<223> OTHER INFORMATION: 3E6 light chain

<400> SEQUENCE: 117

Met Ser Val Leu Thr Gln Val Leu Ala Leu Leu Leu Leu Trp Leu Thr
1               5                   10                  15

Gly Ala Arg Cys Asp Ile Gln Leu Thr Gln Ser Pro Ala Ser Leu Ser

```
                    20                  25                  30
Ala Ser Val Gly Glu Thr Val Thr Ile Thr Cys Arg Ala Ser Asp Asn
                35                  40                  45

Ile His Lys Tyr Leu Ala Trp Tyr Gln Gln Lys Gln Gly Lys Ser Pro
            50                  55                  60

Gln Arg Leu Val Tyr Asn Ala Lys Thr Leu Ala Asp Gly Val Pro Ser
65                  70                  75                  80

Arg Phe Asn Gly Ser Gly Ser Gly Thr Gln Tyr Ser Leu Lys Ile Asn
                85                  90                  95

Ser Leu Gln Pro Glu Asp Phe Gly Ile Tyr Tyr Cys Gln His Phe Trp
            100                 105                 110

Ser Thr Pro Leu Thr Phe Gly Ala Gly Thr Lys Leu Glu Leu Lys
            115                 120                 125

<210> SEQ ID NO 118
<211> LENGTH: 119
<212> TYPE: PRT
<213> ORGANISM: Artificial Sequence
<220> FEATURE:
<223> OTHER INFORMATION: 3E6 heavy chain

<400> SEQUENCE: 118

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
                20                  25                  30

Tyr Met Ser Trp Val Arg Gln Pro Pro Gly Lys Ala Leu Glu Trp Met
            35                  40                  45

Gly Phe Ile Arg Asn Lys Ala Lys Gly Tyr Thr Thr Asp Tyr Ser Ala
        50                  55                  60

Ser Val Lys Gly Arg Phe Thr Ile Ser Arg Asp Asp Ser Gln Ser Ile
65                  70                  75                  80

Leu Tyr Leu Gln Met Asn Thr Leu Arg Pro Glu Asp Ser Ala Thr Tyr
                85                  90                  95

Tyr Cys Ala Arg Asn Tyr Asp Tyr Ser Met Asp Tyr Trp Gly Gln Gly
            100                 105                 110

Thr Ser Val Thr Val Ser Ser
        115

<210> SEQ ID NO 119
<211> LENGTH: 107
<212> TYPE: PRT
<213> ORGANISM: Artificial Sequence
<220> FEATURE:
<223> OTHER INFORMATION: 3E6 light chain

<400> SEQUENCE: 119

Asp Ile Gln Leu Thr Gln Ser Pro Ala Ser Leu Ser Ala Ser Val Gly
1               5                   10                  15

Glu Thr Val Thr Ile Thr Cys Arg Ala Ser Asp Asn Ile His Lys Tyr
                20                  25                  30

Leu Ala Trp Tyr Gln Gln Lys Gln Gly Lys Ser Pro Gln Arg Leu Val
            35                  40                  45

Tyr Asn Ala Lys Thr Leu Ala Asp Gly Val Pro Ser Arg Phe Asn Gly
        50                  55                  60

Ser Gly Ser Gly Thr Gln Tyr Ser Leu Lys Ile Asn Ser Leu Gln Pro
65                  70                  75                  80
```

Glu Asp Phe Gly Ile Tyr Tyr Cys Gln His Phe Trp Ser Thr Pro Leu
            85                  90                  95

Thr Phe Gly Ala Gly Thr Lys Leu Glu Leu Lys
            100                 105

<210> SEQ ID NO 120
<211> LENGTH: 5
<212> TYPE: PRT
<213> ORGANISM: Artificial Sequence
<220> FEATURE:
<223> OTHER INFORMATION: 3E6 fragment

<400> SEQUENCE: 120

Asp Tyr Tyr Met Ser
1               5

<210> SEQ ID NO 121
<211> LENGTH: 19
<212> TYPE: PRT
<213> ORGANISM: Artificial Sequence
<220> FEATURE:
<223> OTHER INFORMATION: 3E6 fragment

<400> SEQUENCE: 121

Phe Ile Arg Asn Lys Ala Lys Gly Tyr Thr Thr Asp Tyr Ser Ala Ser
1               5                   10                  15

Val Lys Gly

<210> SEQ ID NO 122
<211> LENGTH: 8
<212> TYPE: PRT
<213> ORGANISM: Artificial Sequence
<220> FEATURE:
<223> OTHER INFORMATION: 3E6 fragment

<400> SEQUENCE: 122

Asn Tyr Asp Tyr Ser Met Asp Tyr
1               5

<210> SEQ ID NO 123
<211> LENGTH: 11
<212> TYPE: PRT
<213> ORGANISM: Artificial Sequence
<220> FEATURE:
<223> OTHER INFORMATION: 3E6 fragment

<400> SEQUENCE: 123

Arg Ala Ser Asp Asn Ile His Lys Tyr Leu Ala
1               5                   10

<210> SEQ ID NO 124
<211> LENGTH: 7
<212> TYPE: PRT
<213> ORGANISM: Artificial Sequence
<220> FEATURE:
<223> OTHER INFORMATION: 3E6 fragment

<400> SEQUENCE: 124

Asn Ala Lys Thr Leu Ala Asp
1               5

<210> SEQ ID NO 125
<211> LENGTH: 9
<212> TYPE: PRT
<213> ORGANISM: Artificial Sequence
<220> FEATURE:

<223> OTHER INFORMATION: 3E6 fragment

<400> SEQUENCE: 125

Gln His Phe Trp Ser Thr Pro Leu Thr
1               5